United States Patent
Ye et al.

US006806072B2

(10) Patent No.: US 6,806,072 B2
(45) Date of Patent: Oct. 19, 2004

(54) ISOLATED HUMAN KINASE PROTEINS, NUCLEIC ACID MOLECULES ENCODING HUMAN KINASE PROTEINS, AND USES THEREOF

(75) Inventors: Jane Ye, Boyds, MD (US); Chunhua Yan, Boyds, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 10/345,198

(22) Filed: Jan. 16, 2003

(65) Prior Publication Data

US 2003/0129704 A1 Jul. 10, 2003

Related U.S. Application Data

(62) Division of application No. 09/801,191, filed on Mar. 8, 2001, now Pat. No. 6,537,788.

(51) Int. Cl.[7] .......................... C12N 9/12; C12N 15/00; C07H 21/04; C07K 1/00

(52) U.S. Cl. .................. 435/194; 435/440; 530/350; 536/23.2

(58) Field of Search .................. 435/194, 440; 536/23.2; 530/350

(56) References Cited

PUBLICATIONS

Results of BLAST search of SEQ ID No.:2 against Derwent (FastAlert and GeneSeqP) and NCBI (pataa) protein patent databases on Jul. 22, 2003.

Primary Examiner—P. Achutamurthy
Assistant Examiner—Yong Pak
(74) Attorney, Agent, or Firm—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

24 Claims, 29 Drawing Sheets

```
   1 GTGGTCTGTG CGGTGTCTCC CAAACCACTA CCTGGCTGCC CCCGTACCAG
  51 CTGCTGGGAA AGACTACTTC CTCCGAGTTG TGCCGGCCTC CGCGTTCTCC
 101 TCACCTCCCC TCTCCTCCGG ACCTCCGCCC CCTCGCGGAG AGGCCTTGCC
 151 GCTTTAAGAG CCGGGCTAGC GATTGACAAG CAATAAACGC TGAGCGCCCG
 201 GCTGCGCTGG AGCCGCCCGG AGCTAGGGGC TTCCCGCGGC GCAGGAGAGA
 251 CGTTTCAGAG CCCTTGCCTC CTTCACCATG CCGGTTGCCG CCACCAACTC
 301 TGAAACTGCC ATGCAGCAAG TCCTGGACAA CTTGGGATCC CTCCCCAGTG
 351 CCACGGGGGC TGCAGAGCTG GACCTGATCT TCCTTCGACG CATTATGGAA
 401 AGTCCCATAG TAAGATCCCT GGCCAAGGCC CATGAGAGGC TGGAGGAGAC
 451 GAAGCTGGAG GCCGTGAGAG ACAACAACCT GGAGCTGGTG CAGGAGATCC
 501 TGCGGGACCT GGCGCAGCTG GCTGAGCAGA GCAGCACAGC CGCCGAGCTG
 551 GCCCACATCC TCCAGGAGCC CCACTTCCAG TCCCTCCTGG AGACGCACGA
 601 CTCTGTGGCC TCAAAGACCT ATGAGACACC ACCCCCCAGC CCTGGCCTGG
 651 ACCCTACGTT CAGCAACCAG CCTGTACCTC CCGATGCTGT GCGCATGGTG
 701 GGCATCCGCA AGACAGCCGG AGAACATCTG GGTGTAACGT TCCGCGTGGA
 751 GGGCGGCGAG CTGGTGATCG CGCCATTCT GCATGGGGGC ATGGTGGCTC
 801 AGCAAGGCCT GCTGCATGTG GGTGACATCA TCAAGGAGGT GAACGGGCAG
 851 CCAGTGGGCA GTGACCCCCG CGCACTGCAG GAGCTCCTGC GCAATGCCAG
 901 TGGCAGTGTC ATCCTCAAGA TCCTGCCCAG CTACCAGGAG CCCCATCTGC
 951 CCCGCCAGGT ATTTGTGAAA TGTCACTTTG ACTATGACCC GGCCCGAGAC
1001 AGCCTCATCC CCTGCAAGGA AGCAGGCCTG CGCTTCAACG CCGGGGACTT
1051 GCTCCAGATC GTAAACCAGG ATGATGCCAA CTGGTGGCAG GCATGCCATG
1101 TCGAAGGGGG CAGTGCTGGG CTCATTCCCA GCCAGTGCT GGAGGAGAAG
1151 CGGAAAGCAT TTGTCAAGAG GGACCTGGAG CTGACACCAA ACTCAGGGAC
1201 CCTATGCGGC AGCCTTTCAG GAAAGAAAAA GAAGCGAATG ATGTATTTGA
1251 CCACCAAGAA TGCAGAGTTT GACCGTCATG AGCTGCTCAT TTATGAGGAG
1301 GTGGCCCGCA TGCCCCCGTT CCGCCGGAAA ACCCTGGTAC TGATTGGGGC
1351 TCAGGGCGTG GGACGGCGCA GCCTGAAGAA CAAGCTCATC ATGTGGGATC
1401 CAGATCGCTA TGGCACCACG GTGCCCTACA CCTCCCGGCG GCCGAAAGAC
1451 TCAGAGCGGG AAGGTCAGGG TTACAGCTTT GTGTCCCGTG GGGAGATGGA
1501 GGCTGACGTC CGTGCTGGGC GCTACCTGGA GCATGGCGAA TACGAGGGCA
1551 ACCTGTATGG CACACGTATT GACTCCATCC GGGGCGTGGT CGCTGCTGGG
1601 AAGGTGTGCG TGCTGGATGT CAACCCCCAG GCGGTGAAGG TGCTACGAAC
1651 GGCCGAGTTT GTCCCTTACG TGGTGTTCAT CGAGGCCCCA GACTTCGAGA
1701 CCCTGCGGGC CATGAACAGG GCTGCGCTGG AGAGTGGAAT ATCCACCAAG
1751 CAGCTCACGG AGGCGGACCT GAGACGGACA GTGGAGGAGA GCAGCCGCAT
1801 CCAGCGGGGC TACGGGCACT ACTTTGACCT CTGCCGGTC AATAGCAACC
1851 TGGAGAGGAC CTTCCGCGAG CTCCAGACAG CCATGGAGAA GCTACGACA
1901 GAGCCCCAGT GGGTGCCTGT CAGCTGGGTG TACTGAGCCT GTTCACCTGG
1951 TCCTTGGCTC ACTCTGTGTT GAAACCCAGA ACCTGAATCC ATCCCCCTCC
2001 TGACCTGTGA CCCCCTGCCA CAATCCTTAG CCCCCATATC TGGCTGTCCT
2051 TGGGTAACAG CTCCCAGCAG GCCCTAAGTC TGGCTTCAGC ACAGAGGCGT
2101 GCACTGCCAG GGAGGTGGGC ATTCATGGGG TACCTTGTGC CCAGGTGCTG
2151 CCCACTCCTG ATGCCCATTG GTCACCAGAT ATCTCTGAGG GCCAAGCTAT
2201 GCCCAGGAAT GTGTCAGAGT CACCTCCATA ATGGTCAGTA CAGAGAAGAG
2251 AAAAGCTGCT TTGGGACCAC ATGGTCAGTA GGCACACTGC CCCCTGCCAC
2301 CCCTCCCCAG TCACCAGTTC TCCTCTGGAC TGGCCACACC CACCCCATTC
2351 CTGGACTCCT CCCACCTCTC ACCCCTGTGT CGGAGGAACA GGCCTTGGGC
2401 TGTTTCCGTG TGACCAGGGG AATGTGTGGC CCGCTGGCAG CCAGGCAGGC
2451 CCGGGTGGTG GTGCCAGCCT GGTGCCATCT TGAAGGCTGG AGGAGTCAGA
2501 GTGAGAGCCA GTGGCCACAG CTGCAGAGCA CTGCAGCTCC CAGCTCCTTT
2551 GGAAAGGGAC AGGGTCGCAG GGCAGATGCT GCTCGGTCCT TCCCTCATCC
2601 ACAGCTTCTC ACTGCCGAAG TTTCTCCAGA TTTCTCCAAT GTGTCCTGAC
2651 AGGTCAGCCC TGCTCCCCAC AGGGCCAGGC TGGCAGGGGC CAGTGGGCTC
2701 AGCCCAGGTA GGGGCAGGAT GGAGGGCTGA GCCCTGTGAC AACCTGCTGT
2751 TACCAACTGA AGAGCCCCAA GCTCTCCATG GCCCACAGCA GGCACAGGTC
2801 TGAGCTCTAT GTCCTTGACC TTGGTCCATT TGGTTTTCTG TCTAGCCAGG
2851 TCCAGGTAGC CCACTTGCAT CAGGGCTGCT GGGTTGGAGG GGCTAAGGAG
2901 GAGTGCAGAG GGGACCTTGG GAGCCTGGGC TTGAAGGACA GTTGCCCTCC
2951 AGGAGGTTCC TCACACACAA CTCCAGAGGC GCCATTTACA CTGTAGTCTG
3001 TACAACCTGT GGTTCCACGT GCATGTTCGG CACCTGTCTG TGCCTCTGGC
3051 ACCAGGTTGT GTGTGTGTGC GTGTGCACGT GCGTGTGTGT GTGTGTGTGT
3101 CAGGTTTAGT TTGGGGAGGA AGCAAAGGGT TTTGTTTTGG AGGTCACTCT
3151 TTGGGGCCCC TTTCTGGGGG TTCCCCATCA GCCCTCATTT CTTATAATAC
3201 CCTGATCCCA GACTCCAAAG CCCTGGTCCT TTCCTGATGT CTCCTCCCTT
3251 GTCTTATTGT CCCCCTACCC TAAATGCCCC CCTGCCATAA CTTGGGGAGG
3301 GCAGTTTTGT AAAATAGGAG ACTCCCTTTA AGAAGAATG CTGTCCTAGA
3351 TGTACTTGGG CATCTCATCC TTCATTATTC TCTGCATTCC TTCCGGGGGG
```

FIGURE 1A

```
3401 AGCCTGTCCT CAGAGGGGAC AACCTGTGAC ACCCTGAGTC CAAACCCTTG
3451 TGCCTCCCAG TTCTTCCAAG TGTCTAACTA GTCTTCGCTG CAGCGTCAGC
3501 CAAAGCTGGC CCCTGAACCA CTGTGTGCCC ATTTCCTAGG GAAGGGGAAG
3551 GAGAATAAAC AGAATATTTA TTACAAAAAA AAAAAAAAAA AAAAAAAAAA
3601 AAAA
```

(SEQ ID NO:1)
FEATURES:
5'UTR:       1 - 277
Start Codon: 278
Stop Codon:  1934
3'UTR:       1937

Homologous proteins
Top 10 BLAST Hits:

|  | Score | E |
|---|---|---|
| CRA\|335001098694355 /altid=gi\|11525886 /def=ref\|XP_008355.1\| pa... | 1097 | 0.0 |
| CRA\|18000005000011 /altid=gi\|4885493 /def=ref\|NP_005365.1\| palm... | 1096 | 0.0 |
| CRA\|18000005249889 /altid=gi\|7710062 /def=ref\|NP_057904.1\| memb... | 1089 | 0.0 |
| CRA\|335001098694646 /altid=gi\|11526446 /def=ref\|XP_004940.1\| MA... | 793 | 0.0 |
| CRA\|108000000500753 /altid=gi\|7549225 /def=gb\|AAF63790.1\|AF1990... | 789 | 0.0 |
| CRA\|154000124061078 /altid=gi\|12053179 /def=emb\|CAB66770.1\| (AL... | 789 | 0.0 |
| CRA\|18000005250630 /altid=gi\|9910474 /def=ref\|NP_064323.1\| memb... | 788 | 0.0 |
| CRA\|66000019402875 /altid=gi\|7706403 /def=ref\|NP_057531.1\| MAGU... | 786 | 0.0 |
| CRA\|108000000500754 /altid=gi\|7549227 /def=gb\|AAF63791.1\|AF1990... | 781 | 0.0 |
| CRA\|18000005171733 /altid=gi\|3687905 /def=gb\|AAC78484.1\| (AF087... | 454 | e-126 | dbEST:

|  | Score | E |
|---|---|---|
| gi\|12892050 /dataset=dbest /taxon=960... | 1495 | 0.0 |
| gi\|11003636 /dataset=dbest /taxon=96... | 1326 | 0.0 |
| gi\|11253154 /dataset=dbest /taxon=96... | 1217 | 0.0 |
| gi\|11099050 /dataset=dbest /taxon=960... | 906 | 0.0 |
| gi\|12599059 /dataset=dbest /taxon=96... | 852 | 0.0 |
| gi\|6936232 /dataset=dbest /taxon=960... | 809 | 0.0 |
| gi\|8425317 /dataset=dbest /taxon=960... | 620 | e-175 |
| gi\|830774 /dataset=dbest /taxon=9606 /... | 519 | e-145 |
| gi\|11285113 /dataset=dbest /taxon=96... | 391 | e-106 |
| gi\|1527533 /dataset=dbest /taxon=9606 ... | 264 | 7e-68 |

EXPRESSION INFORMATION FOR MODULATORY USE:
gi|12892050   Placenta
gi|11003636   Thyroid gland
gi|11253154   Muscle rhabdomyosarcoma
gi|11099050   Muscle rhabdomyosarcoma
gi|12599059   Adrenal gland
gi|6936232    Muscle rhabdomyosarcoma
gi|8425317    Infant brainBreast
gi|830774     Brain glioblastomanfant brain
gi|11285113   Brain glioblastoma
gi|1527533    Retina Tissue Expression:
Human hippocampus

FIGURE 1B

```
  1 MPVAATNSET AMQQVLDNLG SLPSATGAAE LDLIFLRGIM ESPIVRSLAK
 51 AHERLEETKL EAVRDNNLEL VQEILRDLAQ LAEQSSTAAE LAHILQEPHF
101 QSLLETHDSV ASKTYETPPP SPGLDPTFSN QPVPPDAVRM VGIRKTAGEH
151 LGVTFRVEGG ELVIARILHG GMVAQQGLLH VGDIIKEVNG QPVGSDPRAL
201 QELLRNASGS VILKILPSYQ EPHLPRQVFV KCHFDYDPAR DSLIPCKEAG
251 LRFNAGDLLQ IVNQDDANWW QACHVEGGSA GLIPSQLLEE KRKAFVKRDL
301 ELTPNSGTLC GSLSGKKKKR MMYLTTKNAE FDRHELLIYE EVARMPPFRR
351 KTLVLIGAQG VGRRSLKNKL IMWDPDRYGT TVPYTSRRPK DSEREGQGYS
401 FVSRGEMEAD VRAGRYLEHG EYEGNLYGTR IDSIRGVVAA GKVCVLDVNP
451 QAVKVLRTAE FVPYVVFIEA PDFETLRAMN RAALESGIST KQLTEADLRR
501 TVEESSRIQR GYGHYFDLCL VNSNLERTFR ELQTAMEKLR TEPQWVPVSW
551 VY
(SEQ ID NO:2)
```

FEATURES:
Functional domains and key regions:
-----------------------------------------------------------------

[1] PDOC00001 PS00001 ASN_GLYCOSYLATION
N-glycosylation site 206-209 NASG
-----------------------------------------------------------------

[2] PDOC00004 PS00004 CAMP_PHOSPHO_SITE
cAMP- and cGMP-dependent protein kinase phosphorylation site 349-352 RRKT
-----------------------------------------------------------------

[3] PDOC00005 PS00005 PKC_PHOSPHO_SITE
Protein kinase C phosphorylation site

Number of matches: 12
        1    154-156 TFR
        2    528-530 TFR
        3    314-316 SGK
        4    325-327 TTK
        5    365-367 SLK
        6    385-387 TSR
        7    386-388 SRR
        8    392-394 SER
        9    433-435 SIR
       10    475-477 TLR
       11    489-491 STK
       12    505-507 SSR
-----------------------------------------------------------------

[4] PDOC00006 PS00006 CK2_PHOSPHO_SITE
Casein kinase II phosphorylation site

Number of matches: 14
        1      6-9   TNSE
        2     58-61  TKLE
        3     87-90  TAAE
        4    102-105 SLLE
        5    146-149 TAGE
        6    218-221 SYQE
        7    392-395 SERE
        8    403-406 SRGE
        9    429-432 TRID
       10    494-497 TEAD
       11    501-504 TVEE
       12    523-526 SNLE
       13    528-531 TFRE
       14    534-537 TAME
-----------------------------------------------------------------

[5] PDOC00007 PS00007 TYR_PHOSPHO_SITE
Tyrosine kinase phosphorylation site

Number of matches: 2

FIGURE 2A

```
      1    415-422  RYLEHGEY
      2    457-464  RTAEFVPY
------------------------------------------------------
[6] PDOC00008 PS00008 MYRISTYL
N-myristoylation site Number of matches: 13
      1     20-25   GSLPSA
      2    123-128  GLDPTF
      3    142-147  GIRKTA
      4    170-175  GGMVAQ
      5    190-195  GQPVGS
      6    250-255  GLRFNA
      7    277-282  GGSAGL
      8    281-286  GLIPSQ
      9    307-312  GTLCGS
     10    311-316  GSLSGK
     11    396-401  GQGYSF
     12    424-429  GNLYGT
     13    436-441  GVVAAG
------------------------------------------------------
[7] PDOC00009 PS00009 AMIDATION
Amidation site Number of matches: 2
      1    314-317  SGKK
      2    361-364  VGRR
------------------------------------------------------
[8] PDOC00029 PS00029 LEUCINE_ZIPPER
Leucine zipper pattern 518-539  LCLVNSNLERTFRELQTAMEKL
------------------------------------------------------
[9] PDOC00670 PS00856 GUANYLATE_KINASE_1
Guanylate kinase signature 385-402  TSRRPKDSEREGQGYSFV
```

FIGURE 2B

BLAST Alignment to Top Hit:
Alignment to top blast hit:

```
>CRA|335001098694355 /altid=gi|11525886 /def=ref|XP_008355.1|
        palmitoylated membrane protein 2 [Homo sapiens] /org=Homo
        sapiens /taxon=9606 /dataset=nraa /length=576
        Length = 576

Score = 1097 bits (2806), Expect = 0.0
 Identities = 552/576 (95%), Positives = 552/576 (95%), Gaps = 24/576 (4%)
 Frame = +2

Query: 278    MPVAATNSETAMQQVLDNLGSLPSATGAAELDLIFLRGIMESPIVRSLAK---------- 427
              MPVAATNSETAMQQVLDNLGSLPSATGAAELDLIFLRGIMESPIVRSLAK
Sbjct: 1      MPVAATNSETAMQQVLDNLGSLPSATGAAELDLIFLRGIMESPIVRSLAKVIMVLWFMQQ 60

Query: 428    --------------AHERLEETKLEAVRDNNLELVQEILRDLAQLAEQSSTAAELAHILQ 565
                            AHERLEETKLEAVRDNNLELVQEILRDLAQLAEQSSTAAELAHILQ
Sbjct: 61     NVFVPMKYMLKYFGAHERLEETKLEAVRDNNLELVQEILRDLAQLAEQSSTAAELAHILQ 120

Query: 566    EPHFQSLLETHDSVASKTYETPPPSPGLDPTFSNQPVPPDAVRMVGIRKTAGEHLGVTFR 745
              EPHFQSLLETHDSVASKTYETPPPSPGLDPTFSNQPVPPDAVRMVGIRKTAGEHLGVTFR
Sbjct: 121    EPHFQSLLETHDSVASKTYETPPPSPGLDPTFSNQPVPPDAVRMVGIRKTAGEHLGVTFR 180

Query: 746    VEGGELVIARILHGGMVAQQGLLHVGDIIKEVNGQPVGSDPRALQELLRNASGSVILKIL 925
              VEGGELVIARILHGGMVAQQGLLHVGDIIKEVNGQPVGSDPRALQELLRNASGSVILKIL
Sbjct: 181    VEGGELVIARILHGGMVAQQGLLHVGDIIKEVNGQPVGSDPRALQELLRNASGSVILKIL 240

Query: 926    PSYQEPHLPRQVFVKCHFDYDPARDSLIPCKEAGLRFNAGDLLQIVNQDDANWWQACHVE 1105
              PSYQEPHLPRQVFVKCHFDYDPARDSLIPCKEAGLRFNAGDLLQIVNQDDANWWQACHVE
Sbjct: 241    PSYQEPHLPRQVFVKCHFDYDPARDSLIPCKEAGLRFNAGDLLQIVNQDDANWWQACHVE 300

Query: 1106   GGSAGLIPSQLLEEKRKAFVKRDLELTPNSGTLCGSLSGKKKKRMMYLTTKNAEFDRHEL 1285
              GGSAGLIPSQLLEEKRKAFVKRDLELTPNSGTLCGSLSGKKKKRMMYLTTKNAEFDRHEL
Sbjct: 301    GGSAGLIPSQLLEEKRKAFVKRDLELTPNSGTLCGSLSGKKKKRMMYLTTKNAEFDRHEL 360

Query: 1286   LIYEEVARMPPFRRKTLVLIGAQGVGRRSLKNKLIMWDPDRYGTTVPYTSRRPKDSEREG 1465
              LIYEEVARMPPFRRKTLVLIGAQGVGRRSLKNKLIMWDPDRYGTTVPYTSRRPKDSEREG
Sbjct: 361    LIYEEVARMPPFRRKTLVLIGAQGVGRRSLKNKLIMWDPDRYGTTVPYTSRRPKDSEREG 420

Query: 1466   QGYSFVSRGEMEADVRAGRYLEHGEYEGNLYGTRIDSIRGVVAAGKVCVLDVNPQAVKVL 1645
              QGYSFVSRGEMEADVRAGRYLEHGEYEGNLYGTRIDSIRGVVAAGKVCVLDVNPQAVKVL
Sbjct: 421    QGYSFVSRGEMEADVRAGRYLEHGEYEGNLYGTRIDSIRGVVAAGKVCVLDVNPQAVKVL 480

Query: 1646   RTAEFVPYVVFIEAPDFETLRAMNRAALESGISTKQLTEADLRRTVEESSRIQRGYGHYF 1825
              RTAEFVPYVVFIEAPDFETLRAMNRAALESGISTKQLTEADLRRTVEESSRIQRGYGHYF
Sbjct: 481    RTAEFVPYVVFIEAPDFETLRAMNRAALESGISTKQLTEADLRRTVEESSRIQRGYGHYF 540

Query: 1826   DLCLVNSNLERTFRELQTAMEKLRTEPQWVPVSWVY 1933
              DLCLVNSNLERTFRELQTAMEKLRTEPQWVPVSWVY
Sbjct: 541    DLCLVNSNLERTFRELQTAMEKLRTEPQWVPVSWVY 576 (SEQ ID NO:4)

>CRA|18000005000011 /altid=gi|4885493 /def=ref|NP_005365.1|
        palmitoylated membrane protein 2; MAGUK p55 subfamily
        member 2; discs large, homolog 2 [Homo sapiens] /org=Homo
        sapiens /taxon=9606 /dataset=nraa /length=576
        Length = 576

Score = 1096 bits (2803), Expect = 0.0
 Identities = 551/576 (95%), Positives = 552/576 (95%), Gaps = 24/576 (4%)
 Frame = +2

Query: 278    MPVAATNSETAMQQVLDNLGSLPSATGAAELDLIFLRGIMESPIVRSLAK---------- 427
              MPVAATNSETAMQQVLDNLGSLPSATGAAELDLIFLRGIMESPIVRSLAK
Sbjct: 1      MPVAATNSETAMQQVLDNLGSLPSATGAAELDLIFLRGIMESPIVRSLAKVIMVLWFMQQ 60
```

FIGURE 2C

```
Query:  428  ------------AHERLEETKLEAVRDNNLELVQEILRDLAQLAEQSSTAAELAHILQ  565
             AHERLEETKLEAVRDNNLELVQEILRDLAQLAEQSSTAAELAHILQ
Sbjct:   61  NVFVPMKYMLKYFGAHERLEETKLEAVRDNNLELVQEILRDLAQLAEQSSTAAELAHILQ  120

Query:  566  EPHFQSLLETHDSVASKTYETPPPSPGLDPTFSNQPVPPDAVRMVGIRKTAGEHLGVTFR  745
             EPHFQSLLETHDSVASKTYETPPPSPGLDPTFSNQPVPPDAVRMVGIRKTAGEHLGVTFR
Sbjct:  121  EPHFQSLLETHDSVASKTYETPPPSPGLDPTFSNQPVPPDAVRMVGIRKTAGEHLGVTFR  180

Query:  746  VEGGELVIARILHGGMVAQQGLLHVGDIIKEVNGQPVGSDPRALQELLRNASGSVILKIL  925
             VEGGELVIARILHGGMVAQQGLLHVGDIIKEVNGQPVGSDPRALQELLRNASGSVILKIL
Sbjct:  181  VEGGELVIARILHGGMVAQQGLLHVGDITKEVNGQPVGSDPRALQELLRNASGSVILKIL  240

Query:  926  PSYQEPHLPRQVFVKCHFDYDPARDSLIPCKEAGLRFNAGDLLQIVNQDDANWWQACHVE  1105
             P+YQEPHLPRQVFVKCHFDYDPARDSLIPCKEAGLRFNAGDLLQIVNQDDANWWQACHVE
Sbjct:  241  PNYQEPHLPRQVFVKCHFDYDPARDSLIPCKEAGLRFNAGDLLQIVNQDDANWWQACHVE  300

Query: 1106  GGSAGLIPSQLLEEKRKAFVKRDLELTPNSGTLCGSLSGKKKKRMMYLTTKNAEFDRHEL  1285
             GGSAGLIPSQLLEEKRKAFVKRDLELTPNSGTLCGSLSGKKKKRMMYLTTKNAEFDRHEL
Sbjct:  301  GGSAGLIPSQLLEEKRKAFVKRDLELTPNSGTLCGSLSGKKKKRMMYLTTKNAEFDRHEL  360

Query: 1286  LIYEEVARMPPFRRKTLVLIGAQGVGRRSLKNKLIMWDPDRYGTTVPYTSRRPKDSEREG  1465
             LIYEEVARMPPFRRKTLVLIGAQGVGRRSLKNKLIMWDPDRYGTTVPYTSRRPKDSEREG
Sbjct:  361  LIYEEVARMPPFRRKTLVLIGAQGVGRRSLKNKLIMWDPDRYGTTVPYTSRRPKDSEREG  420

Query: 1466  QGYSFVSRGEMEADVRAGRYLEHGEYEGNLYGTRIDSIRGVVAAGKVCVLDVNPQAVKVL  1645
             QGYSFVSRGEMEADVRAGRYLEHGEYEGNLYGTRIDSIRGVVAAGKVCVLDVNPQAVKVL
Sbjct:  421  QGYSFVSRGEMEADVRAGRYLEHGEYEGNLYGTRIDSIRGVVAAGKVCVLDVNPQAVKVL  480

Query: 1646  RTAEFVPYVVFIEAPDFETLRAMNRAALESGISTKQLTEADLRRTVEESSRIQRGYGHYF  1825
             RTAEFVPYVVFIEAPDFETLRAMNRAALESGISTKQLTEADLRRTVEESSRIQRGYGHYF
Sbjct:  481  RTAEFVPYVVFIEAPDFETLRAMNRAALESGISTKQLTEADLRRTVEESSRIQRGYGHYF  540

Query: 1826  DLCLVNSNLERTFRELQTAMEKLRTEPQWVPVSWVY  1933
             DLCLVNSNLERTFRELQTAMEKLRTEPQWVPVSWVY
Sbjct:  541  DLCLVNSNLERTFRELQTAMEKLRTEPQWVPVSWVY  576  (SEQ ID NO: 5)

>CRA|18000005249889 /altid=gi|7710062 /def=ref|NP_057904.1| membrane
        protein, palmitoylated 2 (MAGUK p55 subfamily member 2);
        p55 subfamily member of MAGUK family [Mus musculus]
        /org=Mus musculus /taxon=10090 /dataset=nraa /length=552
        Length = 552

Score = 1089 bits (2785), Expect = 0.0
 Identities = 539/552 (97%), Positives = 548/552 (98%)
 Frame = +2

Query:  278  MPVAATNSETAMQQVLDNLGSLPSATGAAELDLIFLRGIMESPIVRSLAKAHERLEETKL  457
             MPVAATNSE+AMQQVLDNLGSLP+ATGAAELDLIFLRGIMESPIVRSLAKAHERLEETKL
Sbjct:    1  MPVAATNSESAMQQVLDNLGSLPNATGAAELDLIFLRGIMESPIVRSLAKAHERLEETKL  60

Query:  458  EAVRDNNLELVQEILRDLAQLAEQSSTAAELAHILQEPHFQSLLETHDSVASKTYETPPP  637
             EAVRDNNLELVQEILRDLA+LAEQSSTAAELA ILQEPHFQSLLETHDSVASKTYETPPP
Sbjct:   61  EAVRDNNLELVQEILRDLAELAEQSSTAAELARILQEPHFQSLLETHDSVASKTYETPPP  120

Query:  638  SPGLDPTFSNQPVPPDAVRMVGIRKTAGEHLGVTFRVEGGELVIARILHGGMVAQQGLLH  817
             SPGLDPTFSNQPVPPDAVRMVGIRKTAGEHLGVTFRVEGGELVIARILHGGMVAQQGLLH
Sbjct:  121  SPGLDPTFSNQPVPPDAVRMVGIRKTAGEHLGVTFRVEGGELVIARILHGGMVAQQGLLH  180

Query:  818  VGDIIKEVNGQPVGSDPRALQELLRNASGSVILKILPSYQEPHLPRQVFVKCHFDYDPAR  997
             VGDIIKEVNGQPVGSDPRALQELLR+ASGSVILKILPSYQEPHLPRQVFVKCHFDYDPAR
Sbjct:  181  VGDIIKEVNGQPVGSDPRALQELLRSASGSVILKILPSYQEPHLPRQVFVKCHFDYDPAR  240

Query:  998  DSLIPCKEAGLRFNAGDLLQIVNQDDANWWQACHVEGGSAGLIPSQLLEEKRKAFVKRDL  1177
             DSL PCKEAGLRFNAGDLLQIVNQDDANWWQACHVEGGSAGLIPSQLLEEKRKAFVKRDL
Sbjct:  241  DSLSPCKEAGLRFNAGDLLQIVNQDDANWWQACHVEGGSAGLIPSQLLEEKRKAFVKRDL  300

Query: 1178  ELTPNSGTLCGSLSGKKKKRMMYLTTKNAEFDRHELLIYEEVARMPPFRRKTLVLIGAQG  1357
```

FIGURE 2D

```
                ELTP SGTLCGSLSGKKKKRMMYLTTKNAEFDRHELLIYEEVARMPPFRRKTLVLIGAQG
Sbjct: 301      ELTPTSGTLCGSLSGKKKKRMMYLTTKNAEFDRHELLIYEEVARMPPFRRKTLVLIGAQG 360

Query: 1358     VGRRSLKNKLIMWDPDRYGTTVPYTSRRPKDSEREGQGYSFVSRGEMEADVRAGRYLEHG 1537
                VGRRSLKNKLI+WDPDRYGTTVPYTSRRPKDSEREGQGYSFVSRGEMEAD+RAGRYLEHG
Sbjct: 361      VGRRSLKNKLILWDPDRYGTTVPYTSRRPKDSEREGQGYSFVSRGEMEADIRAGRYLEHG 420

Query: 1538     EYEGNLYGTRIDSIRGVVAAGKVCVLDVNPQAVKVLRTAEFVPYVVFIEAPDFETLRAMN 1717
                EYEGNLYGTRIDSIRGVVA+GKVCVLDVNPQAVKVLRTAEFVPYVVFIEAPD+ETLRAMN
Sbjct: 421      EYEGNLYGTRIDSIRGVVASGKVCVLDVNPQAVKVLRTAEFVPYVVFIEAPDYETLRAMN 480

Query: 1718     RAALESGISTKQLTEADLRRTVEESSRIQRGYGHYFDLCLVNSNLERTFRELQTAMEKLR 1897
                RAALESG+STKQLTEADLRRTVEESSRIQRGYGHYFDL LVNSNLERTFRELQTAMEKLR
Sbjct: 481      RAALESGVSTKQLTEADLRRTVEESSRIQRGYGHYFDLSLVNSNLERTFRELQTAMEKLR 540

Query: 1898     TEPQWVPVSWVY 1933
                TEPQWVPVSWVY
Sbjct: 541      TEPQWVPVSWVY 552 (SEQ ID NO: 6)

>CRA|335001098694646 /altid=gi|11526446 /def=ref|XP_004940.1| MAGUK
         protein p55T; Protein Associated with Lins 2 [Homo
         sapiens] /org=Homo sapiens /taxon=9606 /dataset=nraa
         /length=603
         Length = 603

Score =  793 bits (2025), Expect = 0.0
 Identities = 387/580 (66%), Positives = 477/580 (81%), Gaps = 2/580 (0%)
 Frame = +2

Query: 200      GCAGAARS*GLPAAQERRFRALASFTMPVAATNSETAMQQVLDNLGSLPSATGAAELDLI 379
                GC+ A + G   Q RR    +   +    A     AMQQVL+NL LPS+TGA E+DLI
Sbjct: 30       GCSAAPVAEG---EQRRGATGSGGSGGAEAABVRAAMQQVLENLTELPSSTGAEEIDLI 86

Query: 380      FLRGIMESPIVRSLAKAHERLEETKLEAVRDNNLELVQEILRDLAQLAEQSSTAAELAHI 559
                FL+GIME+PIV+SLAKAHERLE++KLEAV DNNLELV EIL D+  L      AEL  I
Sbjct: 87       FLKGIMENPIVKSLAKAHERLEDSKLEAVSDNNLELVNEILEDITPLINVDENVAELVGI 146

Query: 560      LQEPHFQSLLETHDSVASKTYETPPPSPGLD-PTFSNQPVPPDAVRMVGIRKTAGEHLGV 736
                L+EPHFQSLLE HD VASK Y++PP SP ++   +NQ +P DA+R++GI K AGE LGV
Sbjct: 147      LKEPHFQSLLEAHDIVASKCYDSPPSSPEMNNSSINNQLLPVDAIRILGIHKRAGEPLGV 206

Query: 737      TFRVEGGELVIARILHGGMVAQQGLLHVGDIIKEVNGQPVGSDPRALQELLRNASGSVIL 916
                TFRVE   +LVIARILHGGM+ +QGLLHVGDIIKEVNG  VG++P+ LQELL+N SGSV L
Sbjct: 207      TFRVENNDLVIARILHGGMIDRQGLLHVGDIIKEVNGHEVGNNPKELQELLKNISGSVTL 266

Query: 917      KILPSYQEPHLPRQVFVKCHFDYDPARDSLIPCKEAGLRFNAGDLLQIVNQDDANWWQAC 1096
                KILPSY++    P+QVFVKCHFDY+P  D+LIPCKEAGL+F+  G++LQIVN++D NWWQA
Sbjct: 267      KILPSYRDTITPQQVFVKCHFDYNPYNDNLIPCKEAGLKFSKGEILQIVNREDPNWWQAS 326

Query: 1097     HV-EGGSAGLIPSQLLEEKRKAFVKRDLELTPNSGTLCGSLSGKKKKRMMYLTTKNAEFD 1273
                HV EGGSAGLIPSQ LEEKRKAFV+RD +   NSG CG++S KKKK+MMYLTT+NAEFD
Sbjct: 327      HVKEGGSAGLIPSQFLEEKRKAFVRRDWD---NSGPFCGTISSKKKKKMMYLTTRNAEFD 383

Query: 1274     RHELLIYEEVARMPPFRRKTLVLIGAQGVGRRSLKNKLIMWDPDRYGTTVPYTSRRPKDS 1453
                RHE+ IYEEVA+MPPF+RKTLVLIGAQGVGRRSLKN+ I+ +P R+GTTVP+TSR+P++
Sbjct: 384      RHEIQIYEEVAKMPPFQRKTLVLIGAQGVGRRSLKNRFIVLNPTRFGTTVPFTSRKPRED 443

Query: 1454     EREGQGYSFVSRGEMEADVRAGRYLEHGEYEGNLYGTRIDSIRGVVAAGKVCVLDVNPQA 1633
                E++GQ Y FVSR EMEAD++AG+YLEHGEYEGNLYGT+IDSI  VV  G+ C+LDVNPQA
Sbjct: 444      EKDGQAYKFVSRSEMEADIKAGKYLEHGEYEGNLYGTKIDSILEVVQTGRTCILDVNPQA 503

Query: 1634     VKVLRTAEFVPYVVFIEAPDFETLRAMNRAALESGISTKQLTEADLRRTVEESSRIQRGY 1813
                +KVLRT+EF+PYVVFI AP+ ETLRAM++A +++GI+TK LT++DL++TV+ES+RIQR Y
Sbjct: 504      LKVLRTSEFMPYVVFIAAPELETLRAMHKAVVDAGITTKLLTDSDLKKTVDESARIQRAY 563

Query: 1814     GHYFDLCLVNSNLERTFRELQTAMEKLRTEPQWVPVSWVY 1933
                HYFDL ++N NL++  F +LQTA+EKLR EPQWVP+SWVY
```

FIGURE 2E

Sbjct: 564   NHYFDLIIINDNLDKAFEKLQTAIEKLRMEPQWVPISWVY 603 (SEQ ID NO: 7)

>CRA|108000000500753 /altid=gi|7549225 /def=gb|AAF63790.1|AF199009_1
    (AF199009) PALS2-alpha splice variant [Mus musculus]
    /org=Mus musculus /taxon=10090 /dataset=nraa /length=539
        Length = 539

Score =  789 bits (2015), Expect = 0.0
  Identities = 378/542 (69%), Positives = 461/542 (84%), Gaps = 1/542 (0%)
  Frame = +2

Query: 311   MQQVLDNLGSLPSATGAAELDLIFLRGIMESPIVRSLAKAHERLEETKLEAVRDNNLELV 490
             MQQVL+NL  LPS+TGA E+DLIFL+GIME+PIV+SLAKAHERLE++KLEAV DNNLELV
Sbjct: 1     MQQVLENLTELPSSTGAEEIDLIFLKGIMENPIVKSLAKAHERLEDSKLEAVSDNNLELV 60

Query: 491   QEILRDLAQLAEQSSTAAELAHILQEPHFQSLLETHDSVASKTYETPPPSPGLDPTFSNQ 670
             +EIL D+ L     ABL  IL+EPHFQSLLE HD VASK Y++PP SP ++      N
Sbjct: 61    NEILEDITPLISVDENVAELVGILKEPHFQSLLEAHDIVASKCYDSPPSSPEMNIPSLNN 120

Query: 671   PVPPDAVRMVGIRKTAGEHLGVTFRVEGGELVIARILHGGMVAQQGLLHVGDIIKEVNGQ 850
             +P DA+R++GI K AGE LGVTFRVE  +LVIARILHGGM+ +QGLLHVGDIIKEVNG
Sbjct: 121   QLPVDAIRILGIHKKAGEPLGVTFRVENNDLVIARILHGGMIDRQGLLHVGDIIKEVNGH 180

Query: 851   PVGSDPRALQELLRNASGSVILKILPSYQEPHLPRQVFVKCHFDYDPARDSLIPCKEAGL 1030
             VG++P+ LQELL+N SGSV LKILPSY++    P+QVFVKCHFDY+P D+LIPCKEAGL
Sbjct: 181   EVGNNPKELQELLKNISGSVTLKILPSYRDTITPQQVFVKCHFDYNPFNDNLIPCKEAGL 240

Query: 1031  RFNAGDLLQIVNQDDANWWQACHV-EGGSAGLIPSQLLEEKRKAFVKRDLELTPNSGTLC 1207
             +F+ G++LQIVN++D NWWQA HV EGGSAGLIPSQ LEEKRKAFV+RD +  NSG  C
Sbjct: 241   KFSKGEILQIVNREDPNWWQASHVKEGGSAGLIPSQFLEEKRKAFVRRDWD---NSGPFC 297

Query: 1208  GSLSGKKKKRMMYLTTKNAEFDRHELLIYEEVARMPPFRRKTLVLIGAQGVGRRSLKNKL 1387
             G++S KKKK+MMYLTT+NAEFDRHE+ IYEEVA+MPPF+RKTLVLIGAQGVGRRSLKN+
Sbjct: 298   GTISNKKKKKMMYLTTRNAEFDRHEIQIYEEVAKMPPFQRKTLVLIGAQGVGRRSLKNRF 357

Query: 1388  IMWDPDRYGTTVPYTSRRPKDSEREGQGYSFVSRGEMEADVRAGRYLBIIGEYEGNLYGTR 1567
             I+  +P R+GTTVP+TSR+P++  E++GQ Y FVSR EMEAD++AG+YLEHGEYEGNLYGT+
Sbjct: 358   IVLNPARFGTTVPFTSRKPREDEKDGQAYKFVSRSEMEADIKAGKYLEHGEYEGNLYGTK 417

Query: 1568  IDSIRGVVAAGKVCVLDVNPQAVKVLRTAEFVPYVVFIEAPDFETLRAMNRAALESGIST 1747
             IDSI   VV  G+ C+LDVNPQA+KVLRT+EF+PYVVFI AP+ ETLRAM++A ++GI+T
Sbjct: 418   IDSILEVVQTGRTCILDVNPQALKVLRTSEFMPYVVFIAAPELETLRAMHKAVVDAGITT 477

Query: 1748  KQLTEADLRRTVEESSRIQRGYGHYFDLCLVNSNLERTFRELQTAMEKLRTEPQWVPVSW 1927
             K LT++DL++TV+ES+RIQR Y HYFDL +VN NL++ F +LQTA+EKLR EPQWVP+SW
Sbjct: 478   KLLTDSDLKKTVDESARIQRAYNHYFDLIIVNDNLDKAFEKLQTAIEKLRMEPQWVPISW 537

Query: 1928  VY 1933
             VY
Sbjct: 538   VY 539 (SEQ ID NO: 8)

Hmmer search results (Pfam):
HMM results:

Scores for sequence family classification (score includes all domains):
Model       Description                                    Score    E-value   N
--------    -----------                                    -----    -------   ---
CE00021     CE00021 MAGUK_subfamily_c                      1386.0         0   1
CE00022     CE00022 MAGUK_subfamily_d                       426.0   1.2e-125  3
PF00625     Guanylate kinase                                118.0    1.8e-31  1
PF00595     PDZ domain (Also known as DHR or GLGF)           30.0    4.3e-07  1
PF00018     SH3 domain                                       26.0    1.6e-05  1
PF01706     FliG C-terminal domain                            4.7          7  1
CE00027     CE00027 SAP_synapse_associated_protein         -460.5     0.0017  1
CE00020     CE00020 MAGUK_subfamily_a                      -492.1        6.8  1

FIGURE 2F

Parsed for domains:

| Model | Domain | seq-f | seq-t | | hmm-f | hmm-t | | score | E-value |
|---|---|---|---|---|---|---|---|---|---|
| CE00022 | 1/3 | 8 | 111 | .. | 358 | 483 | .. | 12.7 | 0.0012 |
| PF01706 | 1/1 | 193 | 216 | .. | 26 | 49 | .. | 4.7 | 7 |
| PF00595 | 1/1 | 139 | 218 | .. | 1 | 83 | [] | 30.0 | 4.3e-07 |
| PF00018 | 1/1 | 251 | 291 | .. | 17 | 57 | .] | 26.0 | 1.6e-05 |
| CE00022 | 2/3 | 138 | 471 | .. | 555 | 933 | .. | 334.6 | 1.1e-98 |
| PF00625 | 1/1 | 386 | 476 | .. | 1 | 94 | [. | 118.0 | 1.8e-31 |
| CE00020 | 1/1 | 1 | 552 | [] | 1 | 1019 | [] | -492.1 | 6.8 |
| CE00027 | 1/1 | 2 | 552 | .] | 1 | 890 | [] | -460.5 | 0.0017 |
| CE00021 | 1/1 | 1 | 552 | [] | 1 | 695 | [] | 1386.0 | 0 |
| CE00022 | 3/3 | 498 | 552 | .] | 945 | 999 | .] | 73.1 | 1.8e-21 |

FIGURE 2G

```
   1 CCCCCGGGCC AGCTCCTATC CCAAGACCTC CGCCTTCTTT TCGTCCTGAC
  51 ACGGCACTTA GGACCCTATT CACTGGGTTT AAACTCCACA GGCCCCTTTC
 101 ACCCAGGCCC GTTCCCTCCC TGTCCACCCG CCCCCGCCTC TGGGCCTCT
 151 TTCTGGGGTG CTGGTTGGGA GAACCAAGCC CCGCTGCCCA TTGACACTGG
 201 TCCCCGCCCC TGCGGTAGGG GCTCCAAAGT GGCTTCAGGC ACCAAGGTGG
 251 TGAGCTGTGA GGGGCCCCGG TATCTGCGCG GCCTCCCCGG GGGCTGTGCG
 301 GGTTGGGGGG ACTTAGAAGC CCGGCATTAC GTAAGAACCG TGCTGTTAGC
 351 GCTTCCGGGG GTTGGGGAGC GAGACAGAGG TTGCGCTGGG TCCCGGTGGC
 401 CCCCTGGTCC CCCTAGGCAG CTAACACCAC AATCTTCCCT GGGAGGGGGT
 451 CCGCAGAAGG GCGCGCGCTG CTTCTCCCGC TTCCCAAGCT GTAGCGGGGC
 501 GGGTCGGGAG CCAGGGTTAG GGTCTGGAGA CTTGGGAGGG GACCGGTGCC
 551 AGAAGCGAAG AGCTAGGGTT AGAAAGTTAG GTCAATTAAG GGGGGGGCGG
 601 TGCGGATAAA GACGGGGTGG GGGTTGGCCG GGGCAGTCAT TTAGTGACCT
 651 CATCCCTGGT CTCCGGCGGG CGCGCACGTA GAGAGCCTTC TTTGATGGCT
 701 CACAACACGC CCCCCTCCCC CAGGTCCTAG CGCCCAGGGT GTTAGGGCTG
 751 GGTCCGTTGG GGCAGGGGTG ATCTGATGGT CCAAGCATGC ACGTCCGCCT
 801 GGCCTTTCGA CCCCATCCTC TGGCCCTCAG TTCTGTCCAG ACCTCCCCGC
 851 GACCTCTCGC TCTCCAAAGC GCCTTTGTCA GACCTTTCTT CTCCGCACCT
 901 CTTTGTATGT GTATGGATGG AGGGATGGGT GGGAGGTTGG AAGAAACCTC
 951 TCCCTTTCAC TGCTGGTCCG CTCGCCTGCG GACACTATGG CTGATGTGGA
1001 TATCTCGGAG GCAGAGCTGA GAGGGCATCT GGGCCCAGGC TTTTGGAAGC
1051 CGAGGTGCAG GTTCCCAGAT GTCTGGGTGC AGGACCTTGG CACGGAGCCA
1101 GGCTAGCTTG CCTGGCACTG CCGTTCTCCT GTGGACACAG CCAGGCCCCG
1151 CCCTCTCAGA GGCTTGGACG GGCGTGGGGG AGCAAAGCCA GCCGATGCTC
1201 TGGGAACCGA CTCCCCGGGA GAAACCCAG GCAGGCTGGG CAAGACTTCC
1251 GAGCGCAGGG ATTTCATACA GGATCCTCCC TGCCTTTTCC CGCCGTGCAC
1301 GCTCTAGGGA AGGAGGACTT CTGGAGTCCC TTCTCTGACC CTGTGAGGGA
1351 GAGCAGCGCC AGCCAGGAGA AGGCTCCAGG TCATCAAGGC CTGGGAGGGG
1401 GAGGGAAGGG ATCCCTCCTC CCTGCTCTCT AGGAGTAGAG ATTGGCACCA
1451 GGGGCACGGG CCAGCACAGT GGATCCTGGG CATTTCTTCC AGCCTGGGTG
1501 TAGCCTGAAT AGGGGTGCCC TTCCTCTCCC TGAAAGCACC TTTATTCCAT
1551 GTCCTCAGCG GCAGAGCTGG GAGGAAAGGG AACCATCCCC CTCACTTTTG
1601 TAATTTCTGT CACCTGAGCT CAGGTGACCA GCTCAGGCCT GAGAAGGGAA
1651 TGGGAGCAGA GAGGGTTTTA TTGAAATCAG GTACTAGTCC TCTGGGAAGA
1701 ATCCTCTTTT GGGGGGAGGT GGAGTTGCCG TGGTTCCCCC ACCCCCAGGA
1751 CTCAGCAGGC ATTCAGTCCT AAAGTGGGCA CTGCCAGATG CTTCCCCCCA
1801 CTCCCCACCC CTGCTGTGAG CCACTGCCTC CTGTTGTCAT GGCAACTGGG
1851 AATTAGGGTT TTATCCAGCA GCACATGCCC AGGAAGGCAA AGGGAAGAAG
1901 GGTGGGGGGT AACCCCCTGC CCTCTCCTGG GAGAACGAGG GAGCCACTCC
1951 TAGCCTGGGG AGGCCCTGGA ATGGAAACTG GGGCTGTAGA CTCCATGCTT
2001 GGTTCTGCCC AGAGCACTTG GTCTCCTTGT GCCAGTCTG AGCTAAGAAA
2051 GGGAGAGAGG AGAGAGAGCC AGCCAGAGGG GCCGTGGAGA GGTAGATATC
2101 ACTCTGTCAG CCCCCCAGAT AAATGTGGAA CATCGGCGCT TGGTAGGCC
2151 TAGGTTCCAG AAGCAAATAA AATCAATGTG GTTCTGACTC TCAGGGAACC
2201 TGCGCTAG GAGTACTCAT GTTTTCTACT TTGGCTCAAA TTCTGGACTC
2251 TTTTATTATT TTTTAAATGA CTTTTTTTTT TTTAAGACAG GTTCTTGCTC
2301 TGTTGCCCAG GCTGGAGTGC AGTGGCGCAA TCATGGCTTA CCGTAGCCTC
2351 GACCTCCTGG GCTCAAGAGA TCCCCCTGCC TCAGCCCCAC AAGTAGCTGG
2401 GATCATAGGC ATGCACCACC ACACCTGGAT AATTTTTAAT TTTTTTGTAG
2451 AGATGGGGGT CTCGCCATGT TGCCCAGGTG GCTCTCAAAC TCCTGGGCTC
2501 AGGTGATTCT CCTGCCTCAG CCTCCTAAAG TGCTGGGATT ATAGGCGTGA
2551 GCCACCTTGC TCAGCCAAAT TATAGTCTTA CCCTCTAAAA ATTCTACTTG
2601 TTTCCTCTTC AAAAAACAAA CAAACAAAAA ATACAACAGG AAGAAACACT
2651 TTATTTATAT ACTTATTTTT GAGTCATAAA ACCTGGATTT TCATTTTAGC
2701 TCTCCTTATT AGCTTTGTGA ACTTGGGCAA ATCAGTTAAC CTCCCTTATC
2751 CTCCCTGGTC TCCTCCTCCT CAGAGAAATA GGCGAGTAAT ACCTGCTCTT
2801 CCTGCTTCCC AGGACCGTTG GAATCATTGT TGTTCTCCAA CCCCCACTTT
2851 CTGGGCAGCA CCTTCTCCCC TACCTTTCTG GCTCGTCCTG AAGGGGAGGC
2901 TCTTCCTATT CCCTTCCCCA TTGCTTTGCC CTTGTATCTG CTCATCCTCC
2951 TCTCTCCCCT CTCCAGGAGA GACGTTTCAG AGCCCTTGCC TCCTTCACCA
3001 TGCCGGTTGC CGCCACCAAC TCTGAAACTG GTAAGAAGGG GGTGAGGATG
3051 TTAGCTTATT TCAGTGGTTC AGAGGGTGCC AGGCGAGGAC TTAGGGGTGG
3101 GCACTTGCAC AGCTCCAGAT AAGAACCAAC TGGCTCCACT GCTGTCCACC
3151 CTACCACTCA GCCATTCCTT CTGGCAGCTG CTGTGGCCAT CTCCTCTGTG
3201 TGGGTTCCTG TGCTGGAACG GAGAAGAGAA AGAATAAGAC CCATACCTGC
3251 TCCAGTGTAG GGCTGGAGCA CAACTCACCT CCGTGGAGGG CAGGGGATGC
3301 ATGCTCCAGA GGTGACCCGT ACTATTGCTG GAGGGCAGTG GCATAGGACC
3351 AGGCCTTCAG GAGGTGGCCC CGGAGCTGGG CCTTGGAGAA TGGCTTGGGG
3401 GTGGAGGGAT TACAGCAGCA CAGCCTGGGG CTGAGAAGTC CATAATCGCT
3451 GCCCACTAGG CCAGCATGTG CCAGAGGTGG ACAGGGGGTA CTGGGGACCA
3501 GGAAGCTGTG AGTGAAGGAA CAAGAATACC AGGTTAGGAT ACCTGGACGT
3551 GGCTCTGTAG GAGGCATTAG GACAAGGGAG TGGGCCACTC AGACAAACTA
3601 GCAAAGCCTC AGTGGCAAAC TGCTTAACCT CTTGGAGCTC GCATTTCTTC
3651 TTCTGTAAAG AGGCTGCTGT GAGACGCAAA GGCTGTAATG GGAGAGCACA
3701 TTACTTTTAG GAATAGTCAT AATTATTATG CTGCTGTTGC TGCCGCTGCC
3751 ACCAAGTTGT TGTTGTTGTT TTTGAGACAA GTTCTGGCTC TTTAGCCTAG
3801 GCTGGAGTGC AGTGGCGCAA GCTTGGCTCA CTGCAACCTC TGCCTACCAG
3851 CCTCAAGTCA TTCTCCCACC TCAGCCTCCC AAGTAGCTGG GACTACAGGT
3901 GTGCACCACC ATGCCCAGCT AATTTTTTGTA TTTTTTCGTAA AGACAAAAAT
```

FIGURE 3A

```
3951 GTTGCCCATG CTGGTCTCAA ACTCCTGAGC TCAAGTACTC CACCCGCCTC
4001 GACCTCCCAA ACTACTGGGA TTACAGGTGT GAACCACTGT GCCTGGCCTG
4051 AGTTGTTATT TTGGCATTAA CCCTGTGTCC TTGAAACAGT CACCTCCTTT
4101 TGAAGACCTG AGATTTCCCT AAGATGAGAT GATGGGACAA GATCAGTGTT
4151 CTTAACTTTT TTCTTTTTCT TTTTTTTTCT TTGAGATGGA GTCTCCCTCT
4201 GTTGCCCAGG CTGGAGGGCA GTGGTGGGAT CTCGGCTCAC TGCAACCTTC
4251 ACCTCCCAGG TTCAAGTGAT TCTCCTGCCT CAGCCTCCCA AGTAGCTGGG
4301 ATTACAGGCA CCTGCTATCA TGCCCAGCTA ATTTTTGTAT TTTTGTAGAG
4351 ACTGGGTTTC ACCATGTTGG CCAGGCTGTC CTGACCTCAG GTGATCCACC
4401 TGCCTTGGCC TCCCAAAGTG CTGGGATTAC AGGCATGAGC CACCACACCT
4451 GGCCTGTTCT TAATTTTATT GGTCCTGAGT CACTTAGAAT CTGGTGACAG
4501 CAGTGAGCCC TCATCGTAGA CATATACATC CATGCACAAA AGGTATATTC
4551 TACTCTAGGG GATCATGGAT TCCCGTAGTG CACGCAGGAC CCCAGAAGGT
4601 TAAGTTCCCT GTGCTAGAGG CCCTCTGAGG CCCGGGCAGC TGGGAACTGC
4651 TATGGTTCTG CTCTGAGTTG TCTGAACTTC CCCCTGCCTG GATGCCTCCC
4701 TCCCATGCAG CTCCTTCCCT TGCTCTAGGC CCCACTACTG CCTCTGCCAG
4751 AGGTTCCAGG GCTGCCACTT TGGGTAGAAT GATTCCTCTG TGCCTCCTCT
4801 CCGAGAAAGT GAAGGGAGTG AGCCAGGGCC TAAACTGTGG TACACTTGTC
4851 CAGGAAAGGC CTCTTCTCCT TGCAGTGGAG GGATGGCACC AATGTCCCCA
4901 GCTTCTGCAG CATCAGAGGG CTCAGTCCCC CATCTCCTGT CCAGCCTGCT
4951 GGGCTCCCTG GGGTCTCCCT GCCTCTTTCA GCCTGCCTAG GCCCCACTGT
5001 AAGCTGCTTA GGCATTAATT AAACCCACCC CTGAGCCTGT GCTTAATGGC
5051 CTCTCCAGCC GGGACTGCCC AGTAAACCCA CCAATAGTGC CTGACTGGGG
5101 CGTAGGAGGA GGAGCAAGCC CAGCAATTTG GCTTCGTTGT TGCAGACCAC
5151 TTGATGGGGG CGTGGTGGGG GAGGATGGGG GACAGGGAGT GGAGACTTGG
5201 GGTGTGGCGG TGGGTTCTGC TTCCTCAAAG GACTCCTGGG GCTCCTGCTC
5251 CCCTTCATGT TGTTCGAGGG GCTGCTCCTG GCTTCTCATA TTCAAAGGAA
5301 GAAGTACAAA GTGTTTTTCT TCCTTCAGGC AGCCTCTGTC CTATCCTGAG
5351 CTACATTAGC TCCCAGCTTC AAAAATCTAA TGGTGGATTC TGCCCCTTAT
5401 TATCTGGTGG TCATTATACT TCCCACAGGA TAGAGAGACA GCTGTGTCCC
5451 TGCCTCTGAG TTCAGGCTCC CCTTCCCTCC TCCTCCCCTG GGAGATCCCT
5501 GCCTTGGACT CTGCAAAGGG CAAAGCTTTT AAGATCCTTT TTCCGCCCTT
5551 CCCCATGGGT CAGTATGGTT GAAGGGAGGG AAAGGGTATG GGTGTATTCC
5601 TCTTGCAGGG AGACCCCATA TCTACTTTGG GTAGAGTCAG GGGCCCTTTT
5651 CCTGAGACTT GGGAGATAAA TGGACAGTGG CACTGGGCTG AGAACTTAGA
5701 GATCCTGAAC CTGGCATCTC CTGACCTGCA GCCTTGCTCC CTCTTCCCCT
5751 GTCACCAGAT TCCCTCCCTT TTTTGGATCA AGGCTGGGAT ATGTGGCTGC
5801 TTTCAGGTGG AGCTGTCCCT TTAAATCTCT CCTCCATCCC TGGGTTACTG
5851 TCCTGGTGTG TAATTCTACT GTCATGGCAA CCAGGGGTGC AATGCGACCT
5901 GGTGCCACTC CTCAGGGAAT GTCTGAGTGG AGGCTGCAGT ACCCTGATGG
5951 TGGCCTCTTG GGCACAAGAT CTCAGAGGAA TGGGGTCACC GGAGCGGAGC
6001 TGAGTCCTTC CCTTCTGCCC ACACTTTTCC CTGTGTGCAA ATGTGCCCTC
6051 ATTTTTCCTT TCTGGGGAAC TGAGTTCCAA GTATGCCTGA CTTGCTTCCT
6101 GGGCATCATC CCCTTCATTA AGAGGAAGAA CTCATGGGAG ATGGGGGAGG
6151 GGAAGAAGCT GCTGTGAGGC GAGGGGTAAG CAGGGCTGGG GCACCATCCC
6201 TACCCACAGC GATGCCACCT CCCCCACGTA CCCTGCCTCC CAGTGGCTGA
6251 CCAAGGGTGG GTAGGGGGAG GCGTCTGAGG CTTGAGGTAT TTGCCCCATG
6301 CCCAAGTGAG GCTGCCTCCC GGTGGGAGGC TGAGTCGTTC TTGGGGACTT
6351 CCTTAGACTG AGGGACTATT GTAAAGGAAA CAGGGCCTGG AGAGGGGACT
6401 GAGAGCAGAG GTCAGAGGGC ATAGGGAGGA GGTGGCATGG GGTGTATTAG
6451 AGGAGGGGCT TCTAGAAAAG AGGGTACAGG GACAAGATGG GCCAAGACTT
6501 TTCTCCCTCG GGTCTCCTGA AGCTGGCTGT GAGGGGAGGG TCTCGGAGTA
6551 CCGCGCCAGT CTTGAAGGGG CAGCATGCCT ACCCCCTCCT CAAAACTTCC
6601 TGTTAGCCGC CTCCTCCCCA TCCCCACCGA CACTGACATG CTGGGGATCG
6651 GGCAATCTGT GGGACTAGGG CTCCCTCCCA CCACTCTTCT CCCACCCGGG
6701 TTACCGCCTG CTCTGCACCG CGCAGCGCCA GTCAGGGCTT TAGCCAATCA
6751 GCAAGGCGGT CACGGCGGCT GAGCCTTCCC ATTGGCTGGT TCCTCAGAGG
6801 GCGCTCCTCG ACTCCCGCCT TCCCCAGCCC GGCCAGGCTT TGGCTGGGGA
6851 GGCGGTAGAC GGCGGCGTGT AGGACGCTCC GGGAGTCCCC GGGTCTGGGG
6901 GCCGCCATGG CAGGCAGCCC AGGCAGCGGG GTCTCCTTGG AGGGTATATC
6951 CCTGGAGTCT TCTGAGGAAG CGGAGCTCCA GAGGGAAGGT AGGGAAGGGC
7001 GGGCCAGATG GGGGCGGGGC AGCTGGCCCC TTAGCCTACC TTCCTCCAGC
7051 AGAGTCGGGG CATCTGGGGA GGGTGGCCTG GGAGAGGTCA TCTGAGGGCA
7101 CCTTCAGGAG AGCTGTCCTG GGCAGAGGGC ACCAACTCCC TTGGCTCAGT
7151 CCTCCCCTAG ATAACGGAGG GAATCTGGCA TACCCTGGCA GGAAGGGAAG
7201 GGTCCCTGCC CTGGCCTCTT TCAGAGCCCA CTGAGGGCCT CGCAGGTCTC
7251 TGACCAATGC CAAGCCCCGG CCTGGGCAAG AGGGGTCTGA AGGGCAAGCT
7301 TGCACTTTTT TTTCTGGAGA AGGCAGGGAG CAGGAGGGAG AAGGAGATGG
7351 GAGTCCAGGA GTCCCTGAAC CATCTCTGCC AGCTCCAGTT CCAGTGCCCC
7401 CTCCTCCCCA CTCCTGTTCC TTCCTGGAGG AGGGGGGCAC TGACAAGAGC
7451 ATTGAGAGGC GCCAGGGGTG CATCCTCCGC CGTCCTCCGT GGCTTGGGTA
7501 CTGTTATGCA GATGTAGGCA TGGGCGGCAT GGTGGCAGGA TAATGATACC
7551 CTTCGCCCAT CTCTGCCCCC AGCTGGGCAC ATTCTGCTTC TCGCTTCCTT
7601 TCCCCGGAAC TTGCCACAGC CTGGAACTCC CACCTCTGTC AGTGAGTGAA
7651 GGCAGCCCTC ACCTCAGGTC TCGGGGCAT TGTTGCGGCC CAGCTGCAGG
7701 TGTTATCGTG TCCTCCATTA TGTCCCATTT CGGGCTGAGA GTTTGCTTAT
7751 CCCTGTGATG ACTTGGTGTG ACCTCAGCCT TTGGGTCACA CCAAGGCCTC
7801 CAGTGCCTGT TTCCCTAGCT CCTGCCAGCG TTCCAGGCCT CAGCTTTGAC
7851 TTCCTATCAT CCATGTTAAT TTCTCAGTGA TTATAGATCA TTGTCACTCA
```

FIGURE 3 B

```
 7901 GAGCTGAAGG CCTGTAAACA TCATCTAGCC CAATCCATCC ATTTTACAGG
 7951 CAGGAAAGAC TGAGGCCAGT GAGGGACAGT GACTTGTACA ATGTCACACT
 8001 GAATTAGTGG TGCTTAGACT GGAGGCTGCA GGCCCTGGCT CCTGTGTGGC
 8051 TGCCTGCTTG ACTCTGGGCC TGTACTCACG GACTTGCTCC GAGTACTGTC
 8101 TGTCTCATCC TTGAGCCTGC CAGGTACAGG TGGCTGAGCC CTGGGCTTCA
 8151 GCCCATCTAG AGGTTGAGTG AGGAGCTTGT GGTTTTCTTT TCTTTTTCTT
 8201 TTTTTTTTTT TTGAGACGGA GTCTTGCTTC TGTCGCCCAG GATGGAGGGC
 8251 AATGGCAGGA TCTCAGCTTA CTGCAACCTC CGCCTCCTGG GTTCAAGCGA
 8301 TTTTCCTGCC TCAGCCTCCC GGTAGCTGGG ATTACAGGCG CCTGCCACTA
 8351 CGCCCAGCTA ATTTTTTGTA TTTTTAGTAG AGACAGGGTT TCCCTGTGTT
 8401 GGCCAGGCTG GTCTTGAACT CTTGACCTCA GGCAATCCAC CCGCTTCGGC
 8451 CTCCCAAAGT GCTGGGATTA CAGGCGTGAG CCACCGCGCC CGGCCAGAGA
 8501 CAGTCTTGCT CTGCCACCCA GGCTGGAGTG CAGTGGCGTG ATCTCAGCTC
 8551 ACTGCAATCT CTGCCTCACA GGTTCAAGCA GTTCTCCTGC CTCAGCCTCC
 8601 TGAGTAGCTA GAATTACAGA CCTACACCAC TATGCCTGGC TAATTTTGGT
 8651 ATTTTTAGTA GAGATGGGGT TTTGCCTTGT TGCCCAGGCT GGTCTTGAAC
 8701 TCCTGGCCTC AAGTGATCCA CCCAACAGCT TGTGGTTTTC TGGTGCAGGG
 8751 CAGGATCTGC AACCTGACAC CTGCTTCCCT TTCTCCCTTC TCTCCACCTC
 8801 AGAGTCTCTT CCAGCTGCCT GGAGCCTCCC ACCTGCTCAG GCTGGCATTA
 8851 CCTAGGGTGG AGAGAACAGG CCAAGGAAAC TGTCCCCTTC CTCCAGGATC
 8901 CCTGTCCCAG GCATTCAAGG GCCTGGGGTG CCTGTGCTGG GCAGGGAGGG
 8951 GAATGTTGCT GGGGAGGGGA ATGTTGCCGG GGAGGGGCTG CCTTCTGTGG
 9001 GACATGGGGG TGGGGAAGTG GCAAGTATTG TGGTGTGTTT TGGTCTTCTG
 9051 TACCCAGCTG GTACCTGTGT ATCTCACTGC CCGTACCTTC CCCCAGCCAT
 9101 GCAGCAAGTC CTGGACAACT TGGGATCCCT CCCCAGTGCC ACGGGGGCTG
 9151 CAGAGCTGGA CCTGATCTTC CTTCGAGGCA TTATGGAAAG TCCCATAGTA
 9201 AGATCCCTGG CCAAGGTACA GTGCTCCAGG GAGGTGGGCA CAAGGGCACT
 9251 GTGCTTGGGG AGGCACAGTA GGGGATGGGG TATTAGCTAC AGAGGGCTTT
 9301 GGGAATGGGA CATGTGGCAC AAGAGGCCCC CCTGAAGGGG ATTGTAGAAG
 9351 AAAATCATGC CCAGGTGATG ACCTGAGTGG CTGCAGGTAG AGGGGGCTGC
 9401 CCCCACACCT GTCTGGTGAG TGCGTGGGTG GATGTTTGTT GACTGCCAGC
 9451 TTGTGGAGTG TGTGATTGGT GCGGGTAGC ATGCACATGT TGGAGAATCT
 9501 CTAGAATTCA TCTTGCCTGT CCTTCTGCCT TTGGGCGTTT TGTGTGTATG
 9551 TCTTTCTAAG GTCACCTGCC ATGTATCAGG TTGGGGAGAG ATTCACTAAA
 9601 AGAGAAAATT ATAGGACAAT TTGGTAATGA CAGTGATAGA GGTGGATACA
 9651 CTATGCATTT TGGGAGCATA AAGGACAGGT GTCTAACCCA GCCTGGGGTG
 9701 GGTGAGGAGG GCTTCCTGGA GGAAGGACCA CTTGAGCTGA GTGGAAGAAT
 9751 GAGGAAGAGG GGGAGGGCAT TCTGGGCCAC AGAAGAGCTT GAGCAGAAGC
 9801 ACAGAGGTAA GAAAGAGTCA GGAGTGTGCA GGGGATTGGA AGGGCTGGTG
 9851 TGAGGCTGAG CCTCAAGTGT AAGACAATGC GAGCTGTGCA AAGGTTGGCA
 9901 GGTCTGGAGG GCACTGGGGG CTGTATGTGG GTGCTTGGGC ATCCTTCTGT
 9951 ATCAGGGAGG CTTTATGGTT TTTTTTGTTT TGTTTTGTTT TGAGAAGGAG
10001 TTTTGCTCTT GTTGCCCAGG CTGGAGTGCA ATGGCGTGAT CTTGGCTCAC
10051 TGCAACCTCC ACCTCCTGAG TTCAAGTGAT TCTTCTGCCT CAGTCTCCCG
10101 AGTAGCTGGG ATTACAGGCA TGTGCCACCA CGCCCAGCTA ATTTTGTAGT
10151 TTTAGTAGAG ATGGGGTTTC TCCATGTTGG TCAGGCTGGT CTCCAATTCC
10201 TGACCTCAGG TGATCTGCCT GCCTCAGCCT TCCAAAGTGC TGGGATTACA
10251 GGCATGAGCC ACTGTGCCTG GCAGGCTTTA CATTATTTAA GCAGGGATAT
10301 GATGCCAAAA TGTGGGTGTT TTGGCAGCCA TGTGGAGGAC TGTTGGGGGG
10351 TTATATCTGA AGTTGGAGAG GCCAGTTAGT GGCTCTTCAG TGGATTGAGT
10401 ATAAGATGCT GAGAGCCTGA AATGGAGCTG TGGTCCCAGA CCTTAGGGTA
10451 AACTGGTGGA ACTTGGTGTT TGGCAGTAAG GGCTAGGGTA CAGTAAGGCA
10501 CCTGGGATCC TGCCCCAGGG AGTGTGGAAG GATGCCCCCT CTCCTGAGGG
10551 GGGGAGGTGG GGATGGTGCC CATGGCTGCG TTGGAGGCAA GGCTGGGAGC
10601 TGTGGGAAAT CAGACCTAAT TGCTCAGATT TCTTGGTGAA GGTGGAGCAG
10651 TCCTCTCCTG GGAATTAGGG ATCAGAGATG GAGCAGGAAG ATTCAGAAGG
10701 GAAGGTTTGA CTGGTCACTG AAAGGGAGAA GGAATTAAAT GGATGGGGAC
10751 CTCGACTGTC CATGTCAGGT GCCCGATTTC CCAGGGTGGG GGTGACTCCA
10801 TCCAGAGAGG AAGAGAAAGG AGCGGGGGCT TTGGTCCAGG CACGTGCTG
10851 GCCTGGGGCT GTGGAAGTCG GATGCAGGGA ATTGTGAAGG GAGCTGGTGA
10901 GAGAGGCTCA GAGAAAAGAG GCCCAGGCTG GAAAGAGGCA GAACAGGGAG
10951 AAAATGGAGG TGAAGGCTCG GTGGCTCTCT GAGGTCACAG AGTATTTGAG
11001 GGGTGATGGT AGGGATATAG ATGAAGAGA AAAAGACCAA GGTCAGAGGA
11051 AGGGAGGTAG AGGTGAAAG TTTTCCAAGG AGGACAGTTC TAGGGATGCC
11101 ATGATAATGT AGGGTGGGGC TGCAGTGGAC AGGTAGGTCA TCAGTGTTGA
11151 AGACACCCAG AAATGGAAGG CTCAGGAGTG GGATGGGCTT GTCCACACAC
11201 CTATTGGCAT GTAGGGCTAT GGCAGGCGTC AGGGTGGGGA GAAGACTGAG
11251 GCAGTCCCCA GGGTTTTCAG TGCATGGTGG TGGAGGTGAC CAGGAAGTCG
11301 GCAATGACAG CAAGGGTAGG GAGAAAGAAG GTACAGCCAG GTGGTGGGTT
11351 TTCTGTAGAG CGGGGACTCT GTCACAGGCT GGCTATGGCT GGCCCTGGCA
11401 TGGGATGTGG AGGACCACGT CCCACTGGAG TGGGGATTGC TGCTGCAGGG
11451 GACACCATGT CCTTGGGTTG TAGCCTATTC ACATTATCTG TGGAATGGTT
11501 GAAGACTTGG GAAGATTGTT AACAGCGAAA GATGAAAAGT TGCAGAGGTT
11551 TAATAGTGGG AAGTTCTGGG GAAGAGAAAA CTGAGCAGAT TGGAGGAGAT
11601 TGGAGAAAGG CAGGGTGCTT TTCATTCAGC AATCGAAGAT CCTACTCATT
11651 TACTAAAGAT AAAGACAAGA AGCTGGGAGT AGGGGCATGC ACCTGTAGTC
11701 CCAGCTACTC TGGAGGCTGA GGTGAGAGCA TTGCTTGAGG CCAAGAAGCT
11751 CAAGTGCAGT TCATGTAACA TAGTGAGAGC TCGTCTTCAA TAAATAAGTA
11801 AATAAATAAT AACAATTATA CACATTTCAA ACATAGAGAC TTCCATGAAG
```

FIGURE 3 C

```
11851 GCAGGAATGT TTGTCTTTTT GATTCACTGC AGTATCCCCA GAGCCTACAA
11901 AATGCCTGAC ACATAGTAGG TGCTCACTGA ATATTTGTTG AATGAATAAA
11951 TACAAAAGAG CATAAAAAAA TAACAAACTC CTGAGTACCC ATCTCCAAAA
12001 TGTTAATAAT GTTTGTTTTG ACTCTTGCCA TTTCTTCTTA AGAAATAAAA
12051 AGTATGAGGC ACACGGCACG GTGTGGCTTA CAGCTTTAGT CCCAGCACTT
12101 TGGGAGACCA AGGTGGGTGG ATCATTTGAG CTCAGGATTT CAAGACCAGC
12151 CTGATCAACA TGGTGAAATC CTGTCTCTAT AAAAAAATAG AATTAGCTAA
12201 GCATGGTGGC ATTCACCTGT AGTCCCAACT ACTCAAGAGG CTGAGGCAGG
12251 AGAGTTGCTT GAGCTGGGTA GGTCGAGGCT ACAATGAGCC ATGATCATGC
12301 CACTACAGTC CAGCCTGGGT GACCGAGTGA GACACTGTCT CAAAAAAAAA
12351 AATAAATAAA TAAATAAAAA GTTTGGCACA GTTAATGCCT CTCCCCTTCC
12401 TCATTTTCAC TGCATTCCCT TCCCACAGGT AACCACTGCC TAGAGATTGA
12451 TGTCATTTCA TTGAATGTTG GCTTATCTTG CCTACATATG TGTTTAGCTG
12501 TAAACAATAT ACCTTTGTGG GATTTTTTTT TAGACAGGGT CTTATTCCAT
12551 CTCCCAGGTT GGAGTACAGT GGAACAATTA TAGCTCACTG CAGCCTGGAA
12601 CTCCTGGGCT CAAATGATCC TCCTGCCCTC CTGCCTTAGC CTCCTGAGTA
12651 ACTGGGGCTA CAAATATGTA CCACCATGCC TGGCTAATCT TTAAATTTTT
12701 TTGTAGAGGC AGGGTCTTGC TACATTGTCC AGGCTAGTCT CAAACTCCTG
12751 GCCTCAAGTA ATCCTCTCAG CCTCCCAAAG CACTGGGATT ATAGGCATGA
12801 GCCACCATGA CTGGCTCTAC CTTTGTTATG TGTGCTTTTT TTTTTTTTTT
12851 TTTTTTCCTC TGGAGTCTCA CTCTGTTGCC CAGGCTAGAG TGCAGTGGCG
12901 CATTTCGGCT CACTGCAACC TCCACCTCCC AAGTTGAAGC GATTCTTCTG
12951 CCTCAGCTCC CCGAGTAGCT GGGACTACAG GCATGCACCA CCATGCCCGG
13001 CTAATTTTTG TGTGTGTGTG TGTGTGTATA TATATATATA TATATATATA
13051 TATTTTGAGA TGGAATCTCA CTCTGTCACT GGGCTGGAGT GCAGTGGCAC
13101 AATCTCAGCT CACTGCAACC TCCGCCTCCT GGGTTCAAGC GATTCTCCTG
13151 CCTTAGCCTC CCAAGTAGCT AGGACTACAG GCATGCGCTA CCATGCCCAG
13201 CTAATTTTTG TATTTTTAGT AGAGATGGGG TTTCACCATG TTGGCCAGGA
13251 TGGTCTCGAT CTCTTGACCT CGCAATCCGC CTGCCTTGGC CTCCCAAAGT
13301 GATGGGATTA TAGGTGTGAG CCACCGCACC TGGCCATTTT TGTATTTTTT
13351 TTTTTTTTTT TAGTAGAGAC AGGGTTTCAC CATATTGGCC AGGCTGGTCT
13401 TGAACTCCTG ACCTCATGAT TCGCCTGCCT CAGCCTCCCA AAGTGCTGGG
13451 ATTACAGGCG TGAGCCACCA TGCCTGGCCA TTACGTGTGC TTTTAAATTT
13501 TATATAAATG AAATGATAGT GTAAGGTGCT TCTGTTTTTG AGATTTCTAT
13551 TTCATACAAG TAGTACAGCT ATCGACCTAA GTAGATATAT AGATAGAGAT
13601 AGGGAGATTC ATTTGAACTG CGGTGTGGTG TTCTGATACA GCAGTCCCCA
13651 ACCTTTTTGG CACCAGGGAC CAGTTTTGTG GAAGACAATT TTTCCACGGA
13701 TCAGGGTGAG GGGGGTGGTT TTGGTATGCA ACTGTTCCAC TCAGATCATC
13751 AGGCATTTGT TAGACTTCTC ATAAGGAGCA CACAACCTAG ATCCCTGGCA
13801 CGTGCAGTTC ACGGTAGGGT TGGTGCCCCT GTGAGAATCT AATGCCACCA
13851 CTGATCTGAC AGGAGGTGGA GCTCAGGCAG TAATGCTTGC TCACCTCCTG
13901 CTGTTCACCT ACTTCCTAAC AGGCCACGGA TCACTACTGG TCCATGGCTT
13951 GGGGGTTGGG GACCCCTGTT CTAATATATG AATAGAGCTG TTTGTTTATT
14001 GGTTCCCTTC CTGAGAGATG TGTATGTCAC TGCTGATTTT GCTGTCTTAA
14051 AAACAGTGCT GCAGTGAACA TCCTCATATC CATCTGCTTC TGCATGCATA
14101 TGAGGGTTTC TCTAGAATGG ACACTTGGCA ATGAAATTGA TGAATATGTG
14151 CAGTTTTGAA CCTCAACATC TGTAACTTTC CAAAATTGAT TTCAGAGTTG
14201 GGTTTATGAG TGCTCCACAG CTCTGGGTAC TTTAGCTATT GTCTCCACAG
14251 TGAGACAGTG AGACTCTGCT TTGTGATGGC AGAGTCTCAG AATGAGACAG
14301 CCCTCTTGCC AATACCCTTC AAAGCAGGGT CCCCCTTGAT AGCATTCCTC
14351 TCTGGTCCAG TCCACTCGAC AGTCCACTCG ACAGCTCTCT AATGATGGGT
14401 TTGCTGGCTG GCTGGCTATG TCATTCACTC ATTTGTCCAT CCATCCATCC
14451 ATCCATCCAT CCATCCATCC ATCCATCAAA TACCTATTTT GCACTCGCCA
14501 CATACCAGGC ACAGTGCTGG GGTTATGGCA GTGAACTGCC AGATAGTTTG
14551 TTTTCCTGAT GAAGCCCAAG TCTGTCTTCC TTTCACTGGA CACCACAATG
14601 CCCCAGTCCT GGGACCTCAC AGTAACCTTC AATTGAAAAT GAACCAATGT
14651 GCTGTGTCAC ATTGTAAGTA AACTCCCTTC TCTGGAAACG TTTTTGGCGA
14701 GAAGCTGGTC AGGATTTTTT CCAAGAAATT CCTGGTATGG TTCCGGATTT
14751 GTAGAGCACA ATAGAAGAGA GTATGGACGT TTCTTCCCCT CTGAGACCCC
14801 CAGTATGAGG CTAATGGGCT AAGGCAATCC AGTAACTTCT TTCTCCCTGT
14851 GGTTGTGAAA CAAACAGGAA GTGAATCTCC ATAAAGGAGC CTACCTGAGC
14901 CCACTGGAAA AAAAAAAGCC ATTCATTTCT TCTGTCCTTG TATGGGTGAG
14951 CCTTTGCAAT GTAAATTTGC CACTCCTCTC ATCAAAGACA GTGTCTCTCA
15001 GAGCTCCCTG CATTGGACAA TGGGACCTAC TTCCTCCTTC TCACCAATTT
15051 TAATCATTAT GTGTACACAG ACAAATTTCT AACCTAATAG ACAAAGCACT
15101 GTGATCAAAG ATCCAGCTGC AAAAACTTCG TGAAGTGGCC CAGAAACCCA
15151 CAGGAATGAA ATCAGATTGG AGCCACATGT GGTAGCTGTT GGCCTCCCTC
15201 CCTTACGCTG TGGAGCTGGG CTTGACTCTG TCTGGGGATG TGGCAGACAG
15251 TGTAGGAGGG GCCAGGCTGG GTAGATCTGG GACCAGGGAG GGACAGGGCC
15301 TGAGGATACA AACCCAGAGG GTTAAAGGCC CTAAGGGAAG TCAAGTCTGG
15351 CAGAGAGATC AGAAGTCCAG GCGGTTGGCC GCACACAGCA AGTGGCGGCC
15401 CTGGCAGGTG GCTGGCATCT GGGACGGCTG ACATGGATCC AGTAGCAGGT
15451 GTTCCAGCTA CAGACAAGGC CAAGGTGAGG AATCCAAGGC AGGGGACATT
15501 CAGAAATTCA GAAAAATTGT TACTAATGGG GACAGCTGAG AGGCATGTGA
15551 AGGCTGTTGT GAACTAATTC ACATGAGATG AAGAAGAAAG AACACAGGGC
15601 TTGGAGTCAG AAGATTCCAC TGACCAGCTT TGTGAGTTTG GTATATCTGT
15651 CAACCTCTCT GAACTTCAGT TATTTCTTAT GGAGGAATTT TTAAAAAATT
15701 AATATTTCTT TATGTATTTA TTTTAAAAGA AAGGTGAGGT CTCACCGTGT
15751 TGCCCAGGCT GGTCTTGAAC TCCTGAGCTC AAGTGATCCT CCCACCCTGG
```

FIGURE 3 D

```
15801 CTTCCTAAAG TGCTAGGATT ACAGGTGTGA GCCACCATGC CCAGCCCAGT
15851 TATTTCTTTT GAGAAGTGGG GAGAATGATA CCTATCCCTC AGAGTCGTGG
15901 TGGGGCTAGG TGGAGGTTAT GGAAGTGTAA GTTTTTTTTT TTTTTGAGAC
15951 GGAGTCTTGC TTTGTTGCCC AGGCTGGAGT GTAATGGTGC AATCTCGGCT
16001 CACTGCAACC TCTGCCTCCC AGGTTCAAGC GATTCTCCTG CCTCAGCCTC
16051 CCGAGTAGCT GGGATTACAG GCCCACCATC CCCGGCTAAT TTGTGTATTT
16101 TTAGTAGAGA TGGGGTTTCA CCATGTTGGC CAGGCTGGCC TTGAACTCCT
16151 GACCTCAGGT GATCCACCCA CCTCGGCCTC CTCCCAAAGT GCAGGAATTA
16201 CAGGCATGAG CCACCCCGGC CAGAAGTGAT TTTTGAATCA GGAAGAGTTG
16251 TTATAATCTT AGCTTCAGAC TAGAGTTCAC AGGGAGGCCT CTTGTTCTGT
16301 GGGGAGGCTA GGGTGGAAGA CCTGGGAAAG CAAGACAGGG CCCTAGAAGA
16351 ATAAAGGTCT AGGGAGGTCA CTAAGATAGG GGCTCTGACA AGGGGACATG
16401 ACAAGCAGAG GGTGTAGTGG TGAGGCCAGT GTATCAGTTC ACTTTTGCTG
16451 TGTAACAAAC CATCGTGCTG TGTCGTGGCT TAAAACAACT GTGATTTAAT
16501 TCCCCTGATT TTGTGGGTTG GTTGGGTGGT TCTTCTGGCC TGGGCTTGCT
16551 TAGCTGGGGC TGGGATGGCCT CACTCACATG TCTGGTGTCT
16601 TAGCTGGGAA AACTGCAATG TCTGGGATGG CCAGACCCCC TTTCCATGTG
16651 GTCTCTCATC CTCTAGGAGG GTCTCTCATC CTCAGCCACC TTCACATGGT
16701 AGTCTCACAA GCAAGGAAGG ACAAGCCTCC AGTCACAAGC ACTTTCTAAG
16751 CCTCTGCTCA CATTTGATAA TGGCCCATTG GCTAAAGCAA GTCACATCTG
16801 TCAAACCCAG ATTAAAGAGT TCCTTTACTT TCTGACACAC TACTCTCTGG
16851 GACATCTTTT AATTTAACTA TTTAATTATG AACCAGGGCT TCAAATAGGA
16901 ATTCCCTGTC TTTTGCCATG ATCGGGGGGT TGGAGTGGAG GGCAGAGGGA
16951 AAACTTTTCA GTGAAATGAC TGTGTAGTGT TTGCATTTGC AGCCTGCTAC
17001 AGCTCTGGAT TGGGAGCAAA CAGAACAGAG TGCAGGCTGG TGCCACTATA
17051 AACTAGCTGT GTCTCCCACT TAAGCTTCTG GTCTACCATG AGCTTGAGCC
17101 CCTGCTTTGC TGAGGATAAT TTTCAGAGCA GAATGAAATG AATGGCTACC
17151 ACAGAAATTC AAATCACTCT TCTAGTTCTG GGCCATGTGT CACTTAACAT
17201 GAAAAAGAAG AATAAGTCTT AGCAAAATAA TAGTGAGTAA AAAAGTAGTA
17251 AGGGAAATAA TTGTTCACTT AATGTTAAGT GAAAAAAAAT CAGACCCCAG
17301 GGATGGATAA AATCATGATT CCCCCCTTTT TTTATGTCAT AGAAAATACG
17351 GCCGGGTGCG GTGGCTCACG CCTGTAATCC CAGCACTTTG GGAGGCCGAG
17401 GTGGGTGGAT CACCAGTTCA GGAGATCGAG ACCATCCTGG CTAACATGGT
17451 GAAACCCCGT CTCTACTAAA ATTACAAAAA ATTAGCCAGG CGTGGTGGTG
17501 CATGCCTGTA GTCCCAGCTA CTCGGGAGGC TGAGGCAGGA GAATGGTGTG
17551 AACCCGGGAG ACGGAGGTTG CAGTGAGCCG AGATTGCGCC ACTGCACTCC
17601 AGCCTGGGCA ACAGAGTGAG ACTCTGTCTC AAAAAAAAAA AAAAAAAAAA
17651 AAAACGCATT TGGACAGACA CAATTCCCTT TTTATTAACT ATATTCATTT
17701 CAGAATTTCA GAAGTATGTA GAATACATAC AGACACATTA CAACTCTTTA
17751 ACTGGGAAGC CAGGGAATGA CAAACACACT AAATCAAGAT GGTGCTTTCA
17801 GCTGGGCATG GTGGCTCATG CCTGTAATCC CAGCACTTTG GGAGGCTGAG
17851 CCGGGCGGAT CACCTGAGGT CTGGAGTTCA AGGCCAGCCT CACCAACATG
17901 GAGAAACCCC GTCTCTACTA AAAATACAAA ATTAGCCGGG TGTGTTGGTG
17951 CATGCTGTAA TCCCAGCTAC TCGAGAGGCT AAGGCAGGAG AATCACTTGA
18001 ACCCGGGAGG TGTAGGTTGC AGTGAGCCGA GATTGTGCCA TTGCACTCCA
18051 GGCTGGGCGA TAGAGCGAGA CTCTGTCTCA AAAAAAAAAA AAAAAAAAAA
18101 GATGGTGATT TCTGCAAGTG GGAAGGGTGA GTGGGGCATG TGGTTAGATG
18151 TAGGATATTG ACAAGAGCTT TGTTTTTTAG TTTGGGTGGT GGGTTCTCTT
18201 AGATCCTTGT TATATCATTT AAAAAATCTA ATTTAGGCCA GGTGTGGTGG
18251 CTCACGCCTG TAATTCCAGC ACTTTGGGAG GCCGAGGCAG GCAGATCACC
18301 TGAGCTCAGG AGTTTGTGAC TAGCCTGGGC AACATGGTGA AACCTCATCT
18351 CAACTGAAAT ATAAAAAATT AGCCAGGGT GGTGGCGCGT GCCTGTAGTC
18401 CCAGCTGTTC GGGAGGTTGA AGCACAAGAA TTTTTGAGCC CAGGAAGTGG
18451 AGGTTGCAGT GAGCCAAGAT TGTGCCACTG CACTCCAATT TGGGCTACAG
18501 AGTGAGACTC CGTCTAAAAA AAAAAAAAAT TATTTGTTCA GCCTACTGAA
18551 TTGTTGGTTT TGTATTTGAA TGAATGTTTT CCTCTGGGCT
18601 ATGAGGTTGA GCTTGGAGAG CTGTGCTTTC ATATCTGTGG GTATAAAACG
18651 TCCAGGGGTG GCCACAGGAG GAGGAATGGA TTAGCCCATG GTGGGAATGT
18701 CATTAAGTCA AAGATAGGAG GTAAGCAGCT TAGGAGGCAC CCTGGCTTCC
18751 CCCTTGATCA CACACGTCTC CTCGGTGACA TTGTCCTCCA TCCGTGGACC
18801 AGATAGTGCT AAAGTCAAAA TGAGTGACTT CTCTAATGCT CACATCAGGA
18851 CACCTGTGCC AGAGCTGGCT CCTGTTAACC CAAAAGAGCC ATGCAAGGGT
18901 TGCCATGGTG AGATTGTTGC TGCCTGAGTG CCATTGTTTA TTCTTGACAC
18951 TCAGTTATTT GGGCTTTGAT TCCAACATTG TCCTAGGCAC GGGTAATAG
19001 AGCCAGAGCT GGGACGCCTC CCTCACTCTG GGGCTCCATA GGCTGGGCCA
19051 AGCTAAATGA CTGAAAGTCA CATAGGGGTC TGTGGAAGAC CAGCCCTCTG
19101 GGGCTTGTTC CTTTCCCCAA ATGCTACTCC TCTGCCCCAT CAGTTGTCTG
19151 TTTCCCCAGT AGGTTGTGGA TGTCAGTCTA AAATGCTGCC CACCCGGCAG
19201 AGGATGGTAT GGGAGGCTGT GGGGCCATGT GGGGTGCTGT TCCCTGGCCT
19251 GTTTGGGAAA AGAGAAGGCA GAAAGCATCT AACCTTTATT GAGCACCTGC
19301 TGTCTGCCAG GCACTATGTC CATCTCACCA AATCCTCACA GCAGTCTTAT
19351 GAAGTATTAC TCAAATCTCA GCATCTCATG GCTAAACAAA TTTTCTATTA
19401 TGAAAAAATT TAAGAATATA TCCTGAACCT CCATCACCTA GCACCCCACT
19451 TCAACATTCA ACAAGTCATG CATAATCTTG TTTCATCCAC ACCTTTACCA
19501 GCTTCCCTCT CTCCTCCATT GTTTTGGAGT ACATCTCAGC CATAATAGAT
19551 TGTATCTGCA AGTGTTTCAT TGTGTATATA AACTCCTGGA CTCAACTGAA
19601 AAGGATTCTT TAAAGCTACA CTACTATTCT CACACCTAAA AAAAAATCAA
19651 ACAATAGTTT TCTTTTGAAT TTTTTTAATT AAAAAAATTT TAAAAAATAG
19701 AGATGGGGTC TTGCTGTCTT GAACTCCTGG GCTCAAGTGA TCCTCCTGCC
```

FIGURE 3 E

```
19751 TTGGCCTCCC AAAGTGCTGG GATTACAGGT GTGAGCCATT GTGCCCTGCC
19801 ATGAATTTTT AATAAATGGT ATTGGAACAT CTGGATAGTC ATTTTGAAAG
19851 ATATCAAAGT GTATTTATTC CTCACATCAT ATATCAGAAT AAACTCCAAG
19901 CGGATCAGAG ATCTCTATGT GAAAATATAA ATCATACACG TCCTAGAAGA
19951 AAACAAGGCT CTGTATATGG GAAAAGCCCT CCCTTAAAAA AAAAACAAAA
20001 AAACAAAAAA CTATGCCTCA AAATTCAGAT GCATGAAAGA TTATTAAATT
20051 CACCCACATT AAAAAATTTG TTTTTTGAGC CAGGGTCTTG CTCTGTCACT
20101 CAGGCTGGAG TGCAGTAGTG CAAACAGTGC TCACTGCAGC CTCAATCTCC
20151 TGGGTTCAAG TGATCCTTCC ACCTCAGCCT CCCAAGTAAG AGTAGCAGGG
20201 ACATCAGGTG CATGCCACCA TGCATTAAAA TGAGGATTAA AAATGCTCAG
20251 GTGAATTTTT AAAATATTTT GTAGCAACAG GGGCTTCCCA TCTTACCCAG
20301 GCTGGTCTTG AACTCCTGGG CTCAAGCAGT CCTTCCTCCT TGACCTCCCA
20351 AAGTGTTGGG ATTGCAGGTG TGAACCACTG CACCTGACCT AAATTTTTTT
20401 TTTTTTTTTG CATGCAAAAA CACCACAAGC AGAGTCAAAA GACAAGTGAC
20451 AAACTGGGGG AAATCATTTA CAAGAAATAT CACAAAGGGC TAATTTTCCC
20501 AATAGAGAGA AAACATTTTT TAAAATAGGG AAAAGAATAA AAACCAAGAC
20551 CTGACAGAAA AATTGGGAAA GACATGAGTA GACAGTTCAC AGAAAAAGAT
20601 ATACAGATGG TCCTTAATCA TATGGAGAGA TGTTTGACTT TACTCATAAT
20651 AAGCAAAATG CAAAGTAAGC CCCAATGAGA GATCATTTCT CCTCCATGTG
20701 ATTGGCAGAC ATGCAAATGT TTGATCAACA CTCTGGTGGT GAGCTTCAAG
20751 AAAATCCCTC ATACAGTGCT AGCAGGAGAG CAAACTGGCC AAAGTCCCAT
20801 GGAGGGGAAT TTGTCAATAT CTAAGAAAAT TACGTATGTA TTTGCTGCTT
20851 GACCCAGCAA GACTTCTAGG AATTTACATG GAAGATCTTC TCCACAGATA
20901 TAGAATACTA TGCCGGAGTC ATTTACTGCA ACATTATTTG CAATAGCAAA
20951 GTATTAGAAA CAACCTAAAT ACCCATGGAG ACTGGTTGAA TAAATTACAG
21001 GAATCCAGTC ATGCAATGGA GTCAAATGCA GTAATTAAAA TAATAAGATG
21051 GGCATGGTGG TTCATGCCTG TAATCCCAAC CTGGGAGGCA GAGGTTGCAG
21101 TGAGCTGAGA TCGCGCCACT GCACTCCATC CTGGGTGACA GAGCAAGACT
21151 CTGTCTCAAA CAAACTAACA ATAATAATTA ATAAAGGAAG ATCTCCATGC
21201 AGTTTCATGG AGTGATTTCT ATGACATATT TTTAAATAAA AAGCCAGAAA
21251 ACCAAACCAG TTAAATAAAA GCCCTAGGGT ATCAAAGGGT ATATACAGTG
21301 TTACTGTGTT TTATGTAAGA AAGGGCAATA TATTTATTTA ATTTTTTTTT
21351 TTGGAAACAG AGTCTTGCTC TGTTGCCCAG GCTGGAGGGC AGTGGCGCGA
21401 TCTCAGCTCC TTGCAACCTC TGCCTCCCGG GTCCAAGTGA TTCTCATGAC
21451 TCAGCCTCCT GAGTAGCTGG GATTACAGGC ATGTGCCACA TGCCCGGCTA
21501 ATTTTGTATT TTTGGTAGAG ATGGTGTTTC ACCATGTTGG TCAGGCTCGT
21551 CTCAAACTCC TGACCTCAGG TGATCCTCCT GCCTTGGCTT CCCAAAGTGC
21601 GGGATTACAG GCATGAGCCA CTGTGCCTGG CCTTTAGTGG TGATTTCTGA
21651 GATTTTGATG CACCCATCAC CCAAGCAGTA TACACTGTAC CCAGTGTGTA
21701 GTCTTTTATC CCTTACGCCC CTACTACCCT TCCCGGCTGA TTTTTACTAA
21751 TAGATTTGTG ATAGGTAGTA GCAGTTGTAT AGCAATTTTG AAACTGCTTT
21801 GAATATTGAA GGACAGAACA AATAAGTAAA TATACTGATG TTATTGGGAA
21851 ATAAGTTCTC ACTGAAGGAG AAGGGAGACA CAAATATGGA ATGGGGGAAG
21901 ATGAGAAAAA TCCTTTAATT TTATTTGGAG CCATTAGTAT CTACTAATGA
21951 CTGCCAAAGA AATGATGCCC AGAAACAATG GGTATTGAGT GTCCACATCT
22001 TGGTTTCTAA ATACTATCTC CTGCTAAAAG GAATCAGGGT TCCTTGGAGA
22051 AATTGCTGAT TCCAGACCTG GGGTAGGGAA TGCATCAGAT GAGCCTGTGC
22101 CAGAAGGGAA GAAGATGCTC AAGGACTGAT GGGAACATGT CAACAGGACA
22151 GAGGTGTGAA TGGGCTCCC ACTGGACAAA TTTGGGATAA ACTGGGTCAA
22201 CGAAGATAGT GATCGTAATG GATTAGAACA CATGGAATAA AAAAAATTCA
22251 TAGTGATATC ATGAGGAGGA AAGAGGAGTA AGGTGGTAGG
22301 GAGAAAAGAA GAGCTCATTC TTTTTTTTTT TTTTTTTTGA GCTGGAGTTT
22351 TGCTCTTGTT GCCCAGGCTG GAGTGCAATG GCATGATCTC GGCTCATTGC
22401 AACCTCCACC TCCCAGGTTC AAGCGGTTCT CCTGCCTCAG CCTCCTGAGT
22451 AGCTGGGATT ACAGGCGCCC ACCACTATGC TAGGCTAATT TTTTATATCT
22501 GTAGTAGAAA CGGGGTTTCA CCATGTTGGC CAGGCTGTTT TGCAAACTCC
22551 TGACCTCAGG TAATCCACCT GCCTTGGCCT CCCAAAGTGC AGGGATTACA
22601 GGCGTGAGCC ACTGTGCCTG GCTGAAAAGC TCATTCTTAT AGCAGAATGC
22651 CAATAAATGT AGAAGGAATG ATGGGAATTA GGTAATCACT ATTTTGCAAC
22701 CTCCAGTATA ATAACTCATT TAGGCAAGGG TCATAAATTG ACACTAAATC
22751 CATTGGTGAA GGATTTTGGG GTAACAGAAT AGTCACATAG TCTCAAAGTA
22801 TGGGAAAGAC ACAAAGACAC AAGTACTTCT ACGTAGAACT CTTGTCAAAA
22851 GGATTAACGT AAGTCTAATC ATGAGGAAAC AATCAACTAA ATCTAGTGGT
22901 AGAGCATCCT AAAAACTACT GGCCTGGAGT CTAAAAATGT CTAGGCTGGG
22951 TGCAGTGGCT CATGCCTGTA ATCTCAGGCT TTGGGAGCCT GAAGCAGGAG
23001 GATCACTTGA AGCCAAGAGT TTGAGCTGAC CCTAGGCAAC GTAGTGAGAC
23051 CCTGTCCCTA CAAAACAAAA ACAGAAACAA AAAAAACAAA ACAACAAATG
23101 TTCTGAAAGT CTAAAAGTTA TTGGGATCTG TTCTAGATTA GAGGAGAATA
23151 AAAAGATATG TCAACCAACT ACAACATATG ATCATCAATT AGATCCTGAA
23201 TCAGAAAAAA TAAAATTATA AAGGATACTT TTGGGACAAG AGTGAACATT
23251 TGAATGTGGA CTGTCTTACA TAATGTATTA ATGAATCGAT GTTAAATTTC
23301 TTGCAGGTGA TAATGGTATT GTGGTTTATG CAGCAGAATG TCTTTGTTCC
23351 TATGAAATAC ATGCTGAAAT ACTTTGGGGT AAAGTGGCTT GTGTTGTCTG
23401 CAATGATCTT TCAAAGATTC AGAGGGGAAA AATGGTCTTC ATATATATTA
23451 TTGAAATGGA ATTCTTTTCT TCCTGACCCA TCTAACCTAA CACTCCCCAC
23501 TGGGCTGGTC ACTGGCGAAG GATTCCTTTT CTGTTTTCAG CGCTCCTTGG
23551 TATGGAGCCC GGAGCCAGCA GAGCAACAAA TAGGTGCAGG GCCTGCTCCT
23601 GGCACCGTGT TCTGATTTCC TGTCCCCTCA TTCGCTGGGA ACACTGAGTT
23651 GAGGGCCTGG AGACGCAAGT TCAAGTCCCA TTGACCCTGG GAAAGTTATT
```

FIGURE 3 F

```
23701 CTACCTCCCT AATTTCCTCA TCCTGGGCTT CAGGGTCTTC AAGGCCCCAC
23751 CCAACCATGA TGTCTGGTGG AAGAAGCCGT CTTTGAACGC CAATGCATAT
23801 AGGGTCCTGG GAGCTGGGGA CAATTTGGTA ACTTCTAATG ACCCTCTGTG
23851 GCAAGGGGAT GGAAAGGAAG GTTTGTCCTT TGGTTTCTTC CTTCCCTAAA
23901 CTAGGTCCTA GTAATTTTGG GGAAGAAAGG AGACAGCAAG GAATGCATGT
23951 GCACGTGTGG GTATGATTGT CAGTGAGTGA GGAGCTGAAG CTGGGGGCTG
24001 GGGGGTGGGA TGGGGAAAAT GCCTGGGGGC TGAGGGAGGA CCCTGCTTGG
24051 TGTCCCAGGG CTCCTGGGGA AGCTCCTAGC CCCACCTGTT CTGCTTCCAC
24101 CCCCAGGCCC ATGAGAGGCT GGAGGAGACG AAGCTGGAGG CCGTGAGAGA
24151 CAACAACCTG GAGCTGGTGC AGGAGATCCT GCGGGACCTG GCGCAGCTGG
24201 CTGAGCAGAG CAGCACAGCC GCCGAGCTGG CCCACATCCT CCAGGAGCCC
24251 CACTTCCAGG TTCCTGGCTG CTAGGGCTGG GGTGAGGGAG CAGGAGGTGG
24301 GTGGACTGGG GCATGCTGCT GTTGGATGGG CCAGCAGGAA GTTGGATCTG
24351 GGATGGGAAG AGACCCGGGA CACTGCCCCA TTGTCCCTTC TCTTCCCACC
24401 ACCCCCCAGT CCCTCCTGGA GACGCACGAC TCTGTGGCCT CAAAGACCTA
24451 TGAGACACCA CCCCCCAGCC CTGGCCTGGA CCCTACATTC AGCAACCAGC
24501 CTGTACCTCC CGATGCTGTG CGCATGGTGG GCATCCGCAA GACAGCCGGA
24551 GAACATCTGG TGAGGACTGG GCAGGGCCAG AGGTGGTGCT GGTGAGGGTG
24601 GGGGGATTGA GAATAACCAA TGAACGGACA AAAAAGGCCA AGTGTGGTCT
24651 GAAGATGAAG ATGGGGCCAG CTTTGTGCAG GGAAGGATCG ATGCAGCAAA
24701 GGGTCGGGGG AAGACCCAGG AGACCATAGA CACTGCACAC ACACCTGTGT
24751 CCGCACCTCT CCAGTCTGCC CACCTCTCCC CTCATTAGTA CCTGCTGTAA
24801 GTGAAGAATT TAGGCAGAAG GATGGAGGAG GACTTTGTGA GGGTGGGGGT
24851 GGGTGGGTAG GGACAGGAAT GGAGGAGCTA TTAGGAGACT ATTTGAAGAT
24901 TCTGACTTGG AGCAATTGGG GCCTCATCTT ACACTCCCTC TGACCTCCAG
24951 GGTGTAACGT TCCGCGTGGA GGGCGGCGAG CTGGTGATCG CGCGCATTCT
25001 GCATGGGGGC ATGGTGGCTC AGCAAGGCCT GCTGCATGTG GGTGACATCA
25051 TCAAGGAGGT GAACGGGCAG CCAGTGGGCA GTGACCCCCG CGCACTGCAG
25101 GAGCTCCTGC GCAATGCCAA TGGCAGTGTC ATCCTCAAGA TCCTGCCCAG
25151 CTACCAGGAG CCCCATCTGC CCCGCCAGGT GGGGCCCCTCA CCCAGCACAA
25201 GGCCCAAGGG ATGGCTGAGC CTCCTGGCTG TCAAGGTTGC AGGTCTCACG
25251 GAGGCCCTCC TCTCCTACTG GTTTCCTCCA GGGAAGATGG GGGGTGGGAC
25301 CTGCAGCCCA GGGGCAGCTG ACCGCAGCCG CCGACAGGCC TCTGCCGCTG
25351 CTGCACCTGC ACATGCTCCC ACATTGGCTG GTATTATGCA CGCAGCCACA
25401 GCCTGGGGTA CAAGTGTATG AGAGAGCGCC TGCATTATGG TCAGCGTTCT
25451 TCACGTTTGT GCGCGTGCGC AGGGTGGGGT TGTCATATGT CCTGGATAGC
25501 TGTCTCCTGG TTGGTCAATT CTGGGGGTGT GGCTGCTCTG TCTCCCTATC
25551 CTATTGGGTC TCTCGCCCTC CACCAGAGCC CTTCTCCAAG GGGAGAGGGT
25601 GAGTGGAGGG AGGGATCCAG GATTAGGTGC CAGGGTCCTG TGCCCTACTT
25651 GGTGGTCCCG CATCCTTGGT CCTGAGATCT GAATCTGTA GTACTAGATG
25701 CAAAGGGAGG TTGGCACCAG GGAGGAGCAT GGGCAGGCCT GGAGGCATCA
25751 CTCCTGCAGG GGGACAGTTC CATTGCCCCT TAGTCTCTGT GAAAAGAGGG
25801 GGCATGGGGT AGACCTCCAC CTGCAGCCTT CTGCTGACCC TTCCCCCGAC
25851 CCTTTGCTGA TTCCTGGGCC CAGGTATTTG TGAAATGTCA CTTTGACTAT
25901 GACCCGGCCC GAGACAGCCT CATCCCCTGC AAGGAAGCAG GCCTGCGCTT
25951 CAACGCCGGG GACTTGCTCC AGATCGTAAA CCAGGATGAT GCCAACTGGT
26001 GGCAGGTGAG CTGCGGGCAC CCCCGCATCT CTCCAGGTAT GGTGCATGGG
26051 AGGGCGAGGG CACAGGGAGG GGTCCTCTTG CTCAGGCAGA TCTTGGTCTC
26101 ATGTCCGTTT TAGGCATGCC ATGTCGAAGG GGGCAGTGCT GGGCTCATTC
26151 CCAGCCAGCT GCTGGAGGAG AAGCGGAAAG CATTTGTCAA GAGGGACCTG
26201 GAGCTGACAC CAAACTCAGG TAGGAGGTCC CCCCTACCCC ACACCTCCAA
26251 TCTGGGATCC AACAGGGCCC TGTCTGACCA ACTCACCCAT CTCCCTATGG
26301 CCAGGGACCC TATGCGGCAG CCTTTCAGGA AAGAAAAAGA AGCGAATGAT
26351 GTATTTGACC ACCAAGAATG CAGGTGGGTA TCAGAGCGCC CCCTCCCTTA
26401 CCCTCCTCTA ACATGGCATG CCTTTCCCTG TCCCCACCCA TCACCTGTGA
26451 CGACGTGTGC CTGGCTCAGA TGCTGCCAGC CGTGTCCCTA GGCCCTGCCC
26501 GACTCCCCCC TGCTCCCCTG TTCCAAGCCC TCTTGCCCTC AGCCTCCCTG
26551 AGAGCTCCGC CCCTCCCTCA CCGTGCAGCC TGGTGAGCAG CGCCATCTCC
26601 CTGTGTCCAG AGTTTGACCG TCATGAGCTG CTCATTTATG AGGAGGTGGC
26651 CCGCATGCCC CCGTTCCGCC GGAAAACCCT GGTACTGATT GGGGCTCAGG
26701 GCGTGGGACG GCGCAGCCTG AAGAACAAGC TCATCATGTG GGATCCAGAT
26751 CGCTATGGCA CCACGGTGCC CTGTGAGTGG GAGCTGGGCC CTGCTGAGTT
26801 GGGGACAAGG AGCAGGGCTC CCCTGGGGCC AGGGCTGGGC CCACCGAATG
26851 GGCATCTTCA TGGGCACCAG GCCAGGTGGT ACCTTTGGGT ACACGGGTTG
26901 GGGTGCACGC CCTCTGTGGG TGGTTAGGGG AACTTCAGGC TCAGGAAGGG
26951 TGAGGGAGGT GTCCAGCCAA CAGGTGGCCT AGCGGGCTGG GCTGGCGTCC
27001 ACTTTCCTTC TCTTGTTTCA CTTGCTAAAA GCCATGAAGA AAGTGAGTGC
27051 CCAGCTGTGC ACCCGGGTGA AACAGGCTAC GAGCTGCATG TGTGTAGCCT
27101 TGTGGAAGAC AGGGCTTCTT AGTGGCAGAA ACAGCGGGGG TGGTGGAAGC
27151 TCCTGGCTGC CAGAGGCAGG ACTAAGAGCA CTGCCCTGGT CTGCTTGGCT
27201 CTTGCTGTGT GGCTTTGGGC TGTACATTGC CCTTTCTGGA CCTCAGCCTC
27251 TCTTCTGTGG GCTCTGGGCT GGACCATGAT TACCAGCTCA TGTCTCTGTG
27301 TGTGCCAATG GGGAGAGTGG GGGGCAGGTG TGTGCAAAGG CAGCAGTGCT
27351 GGCAAGATGG GGAGCAGACT GCACCTCCAA GGCTGGGAAA CGGGGGCCTG
27401 GGTAGGGGTG CATATATGTG TCTGAGGCAC TGTAACCTGC CCCTGCCCAT
27451 TTGGTCCAAC CTACCCCCAT CCCCCTAGAC ACCTCCCGGC GGCCGAAAGA
27501 CTCAGAGCGG GAAGGTCAGG GTTACAGCTT TGTGTCCCGT GGGGAGATGG
27551 AGGCTGACGT CCGTGCTGGG CGCTACCTGG AGCATGGCGA ATACGAGGGC
27601 AACCTGTATG GCACACGTAT TGACTCCATC CGGGGCGTGG TCGCTGCTGG
```

FIGURE 3 G

```
27651 GAAGGTGTGC GTGCTGGATG TCAACCCCCA GGTACCGCCA CTCTGCTCCT
27701 TCCCAGCCTG CCCAATGTCC TCTCTGCTGC CTCATTGCTC CCCCATATAG
27751 TTCCAGACAC CTGTCACCTG AACACGCCCA TGTACCCCCT TTGCCCTCAA
27801 CTACTGCTAG AAACCCAGCC CACCTGGAAC CTTTCTCAGC CTTCCAGGGT
27851 CCCCACTCCT CCTCTAGTCT CCTCCAGTCA CCCCAGCCAC CTGCCAGCTG
27901 TTTGTCATTT GTCCCAGGAC TCATGTCCCA GACCCCCGGG CACCCTTTTC
27951 TCATCCACTC CCAAGTGCTC ACCCCAACCC CAGTTACCCT CACAGCCTTT
28001 CTCTGGTTCC TAGGACAGAC ATGGGGATAT ACTCCCTACC TTGCCTTCTC
28051 CTTCTGCAGG CGGTGAAGGT GCTACGAACG GCCGAGTTTG TCCCTTACGT
28101 GGTGTTCATC GAGGCCCCAG ACTTCGAGAC CCTGCGGGCC ATGAACAGGG
28151 CTGCGCTGGA GAGTGGAATA TCCACCAAGC AGCTCACGGT GAGGGCTCTG
28201 AGGTGTGGGG GAGGGGTCTG ATAGCTGCCT AGGGTGGTGG GGGACAGGCC
28251 TGAGCTGACA GAGAGAAGGA GGTGGTGTTG GGGAGGGACA GGGGCCTGCT
28301 CCAGTTATCA GTGAGGCAGG ACGTGGTCCC CCCTGCATAG ATGTGGAAGG
28351 GGAGGTCTGA GAGAGGAAGT CCAAAGTCTC AGAGTGAGCC AGGCACACAC
28401 CTAGCCTGGG ATACATGTGC TTCTGACTCA AGGCCCCCGG CTCAGCCCAC
28451 TCTGCAGAGA CAGAGTGCTG GCCAGAGAGA GTTCCCGAGG GCAACTGGGA
28501 GAGGTGGGCT GGAGGTGGGC CAGGTGAGCT TGGGTTGCTT ACAGCTGGGG
28551 GAAAGCTGAA GGGTAGGAGA AAGCCAGAGG CGGGAAGGCT GGCTGGAGGG
28601 CTGAGTCAGC GTCAGGGAGC AGGCAGCGCC TGGAGGAGAG GCTTCAAGGC
28651 CTCATTGCAG AACTCCAGCC CCATCCTCCT TCCTATGTCT TGCTGCGCCT
28701 TCCCAGGAGG TGGAGGGTTT GCGGCGCTCT GAGCGCAGGG GTCCCTCTGC
28751 TGGCCATGCC TGGTGCTGCA GCATTCCGGC CCCAGGTCAG AGCGTGCCTG
28801 GGGCCCAGGA GAGGCTGTCT AGGCTGGCAC CCTTCTGCCA ATGACCCCCT
28851 TAAGGAGCTC TGGACCTTTG CCTGATCCCC ATTCTGGGCA CCTCCTCCTT
28901 GGCAACAGGT GTGGCCAACT GGAGCTGTTG GGATGCAGCT AGCTTCAGCT
28951 TATTTAAGTC AGTTGTCAAG TACCCTTCCT CACCCCTGCC CATCCAGCTT
29001 CCACTGGGTC GAGGGTGGGG TTGCCCTGGG TACTTGTGGA TTGCCCTGGT
29051 ACCAGCCTGT CTAGCTGCAT AGGTAAGGCA GCCTAGTCAG ACTTGAGGGA
29101 GCACTGGCTT GAGAGTCAGG CAGACCCTGT TTAGCCACTG ACTGGCTATG
29151 TGACCTTTTT ATACCTTCAT TTTCTCTGCT ATAAATGGGA AAGAATTAAT
29201 CCTATCTTGC AGAGCTGTAG TGAAGATTAT GTGGCATGCA AAGCATTTAG
29251 GGGTGTGATT GGCAGTTATT AAAGCTTTAT TCCTCCCTTT CACTCACCAT
29301 CTGTGGTTGA TGGTGAGCCA CTTTGAGGCA CGCAGAGAGG GGCCCCTGCC
29351 TCCCTAGCCA GGGAGTCCAC ACCAGGGTTG GGCTTTGGGG AGGGGGAGTG
29401 GGGGCAGCTG TAGCTCCTTC TGACAGTGGG GGTGAGTTGT GGGCACTGAC
29451 TGTAGGGAGG TCCCCTTGTG CCTGGGCAGG AGGCGGACCT GAGACGGACA
29501 GTGGAGGAGA GCAGCCGCAT CCAGCGGGGC TACGGGCACT ACTTTGACCT
29551 CTGCCTGGTC AATAGCAACC TGGAGAGGAC CTTCCGCGAG CTCCAGACAG
29601 CCATGGAGAA GCTACGGACA GAGCCCCAGT GGGTGCCTGT CAGCTGGGTG
29651 TACTGAGCCT GTTCACCTGG TCCTTGGCTC ACTCTGTGTT GAAACCCAGA
29701 ACCTGAATCC ATCCCCCTCC TGACCTGTGA CCCCCTGCCA CAATCCTTAG
29751 CCCCCATATC TGGCTGTCCT TGGGTAACAG CTCCCAGCAG GCCCTAAGTC
29801 TGGCTTCAGC ACAGAGGCGT GCACTGCCAG GGAGGTGGGC ATTCATGGGG
29851 TACCTTGTGC CCAGGTGCTG CCCACTCCTG ATGCCCATTG GTCACCAGAT
29901 ATCTCTGAGG GCCAAGCTAT GCCCAGGAAT GTGTCAGAGT CACCTCCATA
29951 ATGGTCAGTA CAGAGAAGAG AAAAGCTGCT TTGGGACCAC ATGGTCAGTA
30001 GGCACACTGC CCCCTGCCAC CCCTCCCCAG TCACCAGTTC TCCTCTGGAC
30051 TGGCCACACC CACCCCATTC CTGGACTCCT CCCACCTCTC ACCCCTGTGT
30101 CGGAGGAACA GGCCTTGGGC TGTTTCCGTG TGACCAGGGG AATGTGTGGC
30151 CCGCTGGCAG CCAGGCAGGC CCGGGTGGTG GTGCCAGCCT GGTGCCATCT
30201 TGAAGGCTGG AGGAGTCAGA GTGAGAGCCA GTGGCCACAG CTGCAGAGCA
30251 CTGCAGCTCC CAGCTCCTTT GGAAAGGGAC AGGGTCGCAG GGCAGATGCT
30301 GCTCGGTCCT TCCCTCATCC ACAGCTTCTC ACTGCCGAAG TTTCTCCAGA
30351 TTTCTCCAAT GTGTCCTGAC AGGTCAGCCC TGCTCCCCAC AGGGCCAGGC
30401 TGGCAGGGGC CAGTGGGCTC AGCCCAGGTA GGGGCAGGAT GGAGGGCTGA
30451 GCCCTGTGAC AACCTGCTGC TACCAACTGA AGAGCCCCAA GCTCTCCATG
30501 GCCCACAGCA GGCACAGGTC TGAGCTCTAT GTCCTTGACC TTGGTCCATT
30551 TGGTTTTCTG TCTAGCCAGG TCCAGGTAGC CCACTTGCAT CAGGGCTGCT
30601 GGGTTGGAGG GGCTAAGGAG GAGTGCAGAG GGGACCTTGG GAGCCTGGGC
30651 TTGAAGGACA GTTGCCCTCC AGGAGGTTCC TCACACACAA CTCCAGAGGC
30701 GCCATTTACA CTGTAGTCTG TACAACCTGT GGTTCCACGT GCATGTTCGG
30751 CACCTGTCTG TGCCTCTGGC ACCAGGTTGT GTGTGTGTGC GTGTGCACGT
30801 GCGTGTGTGT GTGTGTGTGT CAGGTTTAGT TTGGGGAGGA AGCAAAGGGT
30851 TTTGTTTTGG AGGTCACTCT TTGGGGCCCC TTTCTGGGGG TTCCCCATCA
30901 GCCCTCATTT CTTATAATAC CCTGATCCCA GACTCCAAAG CCCTGGTCCT
30951 TTCCTGATGT CTCCTCCCTT GTCTTATTGT CCCCCTACCC TAAATGCCCC
31001 CCTGCCATAA CTTGGGGAGG GCAGTTTTGT AAAATAGGAG ACTCCCTTTA
31051 AGAAAGAATG CTGTCCTAGA TGTACTTGGG CATCTCATCC TTCATTATTC
31101 TCTGCATTCC TTCCGGGGGG AGCCTGTCCT CAGAGGGGAC AACCTGTGAC
31151 ACCCTGAGTC CAAACCCTTG TGCCTCCCAG TTCTTCCAAG TGTCTAACTA
31201 GTCTTCGCTG CAGCGTCAGC CAAAGCTGGC CCCTGAACCA CTGTGTGCCC
31251 ATTTCCTAGG GAAGGGGAAG GAGAATAAAC AGAATATTTA TTACAAATGT
31301 TAGAATATAT TTCTTATACT AGGAATCTCA TTTGCATTTG CATAGACTAT
31351 ACACATGGGG TGGAAAGGCC AGGCCTGCCC CCATCTCGTT GGTGTGGCTC
31401 TGCGTATACT ACACACTCAT TCTCCTGCTC CTCTTTTCCC TTAGTCAGTG
31451 TCCTTTCATC CTGATTCAGC TCTGCCTTGC ATCACCCTCA GCCTAAGGGA
31501 GTGGGAAGGA AATGGGGTGT TTTCTTGCTG ACCTGAGGCT ATAGGGTCAC
31551 TTGCCATTTC CTACCTTCTC TGGGGGATTT GAGGGTAGAG GCAGGGGAAG
```

FIGURE 3 H

```
31601 ATCTGTTGTT GCAGTTGCTT CTGCCCCCTT GATCCAAATG ACCATCATCT
31651 CTGATGGAGA TGGGTTGGGT ACCTGGCCTT CATGGCACCT TCACTGCTAG
31701 GGATGCTCAA GGGGCAGGCC TGGGGCCCTT CCCTCCTGTC TCTTCTCGGT
31751 CTTTCCTCTC TGAGCAGCCT CCTACCTCCC CTGCCTGAGC CCTCACTCCA
31801 CAGCCCTCCC AGGTACCTAG CAGAGGCTGT CAGTCCTTGG CTCACCTGGA
31851 ACAGGGCTGG GGCTGGGTTG GAACAGGTGT GTGCCCCAC CACAGCTCTA
31901 TGACTCTGTT CTCCCTCCCT GCCATTGTGG ACTCTTGTAT TTGAGGGACC
31951 TCAAGAGAGT GAGGACCCTA CCATCCACTG TCCATATTCA GTCCCAGCCC
32001 CAGTGCGCTT CCTCTGTTCC CTCCCTCAGC CATCCAATTC TTGAGTTTTC
32051 TCACTGATTG GTTTTCTTTC TTTTTCCTTG GATTAAATGT GAAAGCAAAG
32101 GCTTCTGGCT CTGCTTTTCT TTGGTTGGGG TTGGATGGAT GGCTTTGGGA
32151 GAGAGTGAGA GCTGGGGAGC ACAGCACAGA TGACTACTAG AATGGAAGTC
32201 AGAGCAACAT GTCTTGTTTT CTGCGATGTC TTCCTTTCCT CTGTCTTGCC
32251 CCTGCACACT CCCCCATCCC CAGAAGATGC TCCTTCTAAG TGCTTGTACC
32301 CAAGGACATG AACAGACATT TCTCAAAAGA AGACATACAA GTGACAATGT
32351 ATGAAAAAGT GCTTTACGTC ACTAATCATC AGAGAAATGC AAACCAAAAC
32401 TACCATGAGT TACCATCTCA CACCAGTCAG AATGGCTATT AAAAGGTCAA
32451 AAAATAAGAG ATGCTGGTGA AGTTGCAGAT AAGAGGGAGT GCTTATACAC
32501 TATTGGTGGG AACGTACATT AGTTCAGCCC CCGTGGAAAG CTGTTTGGGG
32551 AGTTCTCATA GAACTACCAT TCATTCCAGC AATCCCATCA CTGGGCATCT
32601 ACCCAAAGGA GAAGAAATCG TTCCACCAAA AAGATACCTG CACTTGTGTG
32651 ACTG
(SEQ ID NO:3)
```

FEATURES:
Start: 3000
Exon: 3000-3030
Intron: 3031-9096
Exon: 9097-9215
Intron: 9216-24106
Exon: 24107-24259
Intron: 24260-24409
Exon: 24410-24559
Intron: 24560-24950
Exon: 24951-25178
Intron: 25179-25873
Exon: 25874-26005
Intron: 26006-26113
Exon: 26114-26219
Intron: 26220-26304
Exon: 26305-26373
Intron: 26374-26610
Exon: 26611-26772
Intron: 26773-27478
Exon: 27479-27681
Intron: 27682-28059
Exon: 28060-28188
Intron: 28189-29479
Exon: 29480-29653
Stop: 29654

SNPs:

| DNA Position | Major | Minor | Domain | Protein Position | Major | Minor |
|---|---|---|---|---|---|---|
| 310 | G | T | Beyond ORF(5') | | | |
| 314 | T | G | Beyond ORF(5') | | | |
| 1200 | C | G | Beyond ORF(5') | | | |
| 1211 | T | C | Beyond ORF(5') | | | |
| 1329 | C | T | Beyond ORF(5') | | | |
| 1339 | C | A | Beyond ORF(5') | | | |
| 1412 | T | C | Beyond ORF(5') | | | |
| 2121 | - | A | Beyond ORF(5') | | | |
| 2264 | T | A | Beyond ORF(5') | | | |
| 2278 | T | - | Beyond ORF(5') | | | |
| 2482 | C | G | Beyond ORF(5') | | | |
| 2584 | G | T | Beyond ORF(5') | | | |
| 2816 | C | T | Beyond ORF(5') | | | |
| 3424 | C | T | Intron | | | |
| 3528 | A | G | Intron | | | |
| 3581 | T | C | Intron | | | |
| 3784 | C | G | Intron | | | |
| 4170 | - | T | Intron | | | |
| 4526 | A | G | Intron | | | |
| 4579 | C | T | Intron | | | |
| 4730 | C | T | Intron | | | |
| 5060 | C | T | Intron | | | |
| 5195 | A | C | Intron | | | |

FIGURE 3 I

| | | | | | | | |
|---|---|---|---|---|---|---|---|
| 6070 | C | A | Intron | | | | |
| 7829 | C | G | Intron | | | | |
| 7899 | C | G | Intron | | | | |
| 8880 | C | T | Intron | | | | |
| 8978 | C | T | Intron | | | | |
| 9594 | G | C | Intron | | | | |
| 11334 | T | C | Intron | | | | |
| 11467 | G | A | Intron | | | | |
| 12353 | T | A | Intron | | | | |
| 12538 | A | G | Intron | | | | |
| 13471 | T | C | Intron | | | | |
| 13969 | C | G | T | Intron | | | |
| 14560 | T | A | Intron | | | | |
| 14637 | A | G | Intron | | | | |
| 15797 | C | T | Intron | | | | |
| 17246 | T | C | Intron | | | | |
| 18359 | A | G | Intron | | | | |
| 18494 | A | G | Intron | | | | |
| 18998 | T | C | Intron | | | | |
| 20312 | A | G | Intron | | | | |
| 20745 | T | C | Intron | | | | |
| 21422 | G | C | Intron | | | | |
| 21624 | T | C | Intron | | | | |
| 22826 | T | G | C | Intron | | | |
| 23041 | G | A | Intron | | | | |
| 23379 | G | A | Intron | | | | |
| 23439 | T | C | Intron | | | | |
| 23779 | A | G | Intron | | | | |
| 24196 | C | G | Exon | 80 | H | Q | |
| 24197 | C | G | Exon | 81 | L | V | |
| 24487 | A | G | Exon | 127 | T | T | |
| 24689 | C | T | Intron | | | | |
| 25022 | A | G | Exon | 175 | Q | Q | |
| 26015 | G | A | Intron | | | | |
| 28829 | A | C | Intron | | | | |
| 29260 | C | T | Intron | | | | |
| 29673 | T | C | Beyond ORF(3') | | | | |
| 30229 | T | C | Beyond ORF(3') | | | | |
| 30470 | C | T | Beyond ORF(3') | | | | |
| 30829 | A | G | Beyond ORF(3') | | | | |
| 31615 | C | T | Beyond ORF(3') | | | | |
| 32020 | C | T | Beyond ORF(3') | | | | |

Context:

DNA
Position

310
CAGCTCCTATCCCAAGACCTCCGCCTTCTTTTCGTCCTGACACGGCACTTAGGACCCTAT
TCACTGGGTTTAAACTCCACAGGCCCCTTTCACCCAGGCCCGTTCCCTCCCTGTCCACCC
GCCCCCGCCCCTGGGCCCTCTTTCTGGGGTGCTGGTTGGGAGAACCAAGCCCCGCTGCCC
ATTGACACTGGTCCCCGCCCCTGCGGTAGGGGCTCCAAAGTGGCTTCAGGCACCAAGGTG
GTGAGCTGTGAGGGGCCCCGGTATCTGCGCGGCCTCCCCGGGGGCTGTGCGGGTTGGGGG
[G,T]
ACTTAGAAGCCCGGCATTACGTAAGAACCGTGCTGTTAGCGCTTCCGGGGGTTGGGGAGC
GAGACAGAGGTTGCGCTGGGTCCCGGTGGCCCCCTGGTCCCCCTAGGCAGCTAACACCAC
AATCTTCCCTGGGAGGGGGTCCGCAGAAGGGCGCGCGCTGCTTCTCCCGCTTCCCAAGCT
GTAGCGGGGCGGGTCGGGAGCCAGGGTTAGGGTCTGGAGACTTGGGAGGGGACCGGTGCC
AGAAGCGAAGAGCTAGGGTTAGAAAGTTAGGTCAATTAAGGGGGGGGCGGTGCGGATAAA

314
TCCTATCCCAAGACCTCCGCCTTCTTTTCGTCCTGACACGGCACTTAGGACCCTATTCAC
TGGGTTTAAACTCCACAGGCCCCTTTCACCCAGGCCCGTTCCCTCCCTGTCCACCCGCCC
CCGCCCCTGGGCCCTCTTTCTGGGGTGCTGGTTGGGAGAACCAAGCCCCGCTGCCCATTG
ACACTGGTCCCCGCCCCTGCGGTAGGGGCTCCAAAGTGGCTTCAGGCACCAAGGTGGTGA
GCTGTGAGGGGCCCCGGTATCTGCGCGGCCTCCCCGGGGGCTGTGCGGGTTGGGGGGACT
[T,G]
AGAAGCCCGGCATTACGTAAGAACCGTGCTGTTAGCGCTTCCGGGGGTTGGGGAGCGAGA
CAGAGGTTGCGCTGGGTCCCGGTGGCCCCCTGGTCCCCCTAGGCAGCTAACACCACAATC
TTCCCTGGGAGGGGGTCCGCAGAAGGGCGCGCGCTGCTTCTCCCGCTTCCCAAGCTGTAG
CGGGGCGGGTCGGGAGCCAGGGTTAGGGTCTGGAGACTTGGGAGGGGACCGGTGCCAGAA
GCGAAGAGCTAGGGTTAGAAAGTTAGGTCAATTAAGGGGGGGGCGGTGCGGATAAAGACG

1200
TCTTTGTATGTGTATGGATGGAGGGATGGGTGGGAGGTTGGAAGAAACCTCTCCCTTTCA
CTGCTGGTCCGCTCGCCTGCGGACACTATGGCTGATGTGGATATCTCGGAGGCAGAGCTG
AGAGGGCATCTGGGCCCAGGCTTTTGGAAGCCGAGGTGCAGGTTCCCAGATGTCTGGGTG
CAGGACCTTGGCACGGAGCCAGGCTAGCTTGCCTGGCACTGCCGTTCTCCTGTGGACACA
GCCAGGCCCCGCCCTCTCAGAGGCTTGGACGGGCGTGGGGGAGCAAAGCCAGCCGATGCT
[C,G]

FIGURE 3 J

```
        TGGGAACCGACTCCCCGGGAGAAAACCCAGGCAGGCTGGGCAAGACTTCCGAGCGCAGGG
        ATTTCATACAGGATCCTCCCTGCCTTTTCCCGCCCTCCACGCTCTAGGGAAGGAGGACTT
        CTGGAGTCCCTTCTCTGACCCTGTGAGGGAGAGCAGCGCCAGCCAGGAGAAGGCTCCAGG
        TCATCAAGGCCTGGGAGGGGGAGGGAAGGGATCCCTCCTCCCTGCTCTCTAGGAGTAGAG
        ATTGGCACCAGGGGCACGGGCCAGCACAGTGGATCCTGGGCATTTCTTCCAGCCTGGGTG

1211    GTATGGATGGAGGGATGGGTGGGAGGTTGGAAGAAACCTCTCCCTTTCACTGCTGGTCCG
        CTCGCCTGCGGACACTATGGCTGATGTGGATATCTCGGAGGCAGAGCTGAGAGGGCATCT
        GGGCCCAGGCTTTTGGAAGCCGAGGTGCAGGTTCCCAGATGTCTGGGTGCAGGACCTTGG
        CACGGAGCCAGGCTAGCTTGCCTGGCACTGCCGTTCTCCTGTGGACACAGCCAGGCCCCG
        CCCTCTCAGAGGCTTGGACGGGCGTGGGGGAGCAAAGCCAGCCGATGCTCTGGGAACCGA
        [T,C]
        TCCCCGGGAGAAAACCCAGGCAGGCTGGGCAAGACTTCCGAGCGCAGGGATTTCATACAG
        GATCCTCCCTGCCTTTTCCCGCCCTCCACGCTCTAGGGAAGGAGGACTTCTGGAGTCCCT
        TCTCTGACCCTGTGAGGGAGAGCAGCGCCAGCCAGGAGAAGGCTCCAGGTCATCAAGGCC
        TGGGAGGGGGAGGGAAGGGATCCCTCCTCCCTGCTCTCTAGGAGTAGAGATTGGCACCAG
        GGGCACGGGCCAGCACAGTGGATCCTGGGCATTTCTTCCAGCCTGGGTGTAGCCTGAATA

1329    CTGGGCCCAGGCTTTTGGAAGCCGAGGTGCAGGTTCCCAGATGTCTGGGTGCAGGACCTT
        GGCACGGAGCCAGGCTAGCTTGCCTGGCACTGCCGTTCTCCTGTGGACACAGCCAGGCCC
        CGCCCTCTCAGAGGCTTGGACGGGCGTGGGGGAGCAAAGCCAGCCGATGCTCTGGGAACC
        GACTCCCCGGGAGAAAACCCAGGCAGGCTGGGCAAGACTTCCGAGCGCAGGGATTTCATA
        CAGGATCCTCCCTGCCTTTTCCCGCCCTCCACGCTCTAGGGAAGGAGGACTTCTGGAGTC
        [C,T]
        CTTCTCTGACCCTGTGAGGGAGAGCAGCGCCAGCCAGGAGAAGGCTCCAGGTCATCAAGG
        CCTGGGAGGGGGAGGGAAGGGATCCCTCCTCCCTGCTCTCTAGGAGTAGAGATTGGCACC
        AGGGGCACGGGCCAGCACAGTGGATCCTGGGCATTTCTTCCAGCCTGGGTGTAGCCTGAA
        TAGGGGTGCCCTTCCTCTCCCTGAAAGCACCTTTATTCCATGTCCTCAGCGGCAGAGCTG
        GGAGGAAAGGGAACCATCCCCCTCACTTTTGTAATTTCTGTCACCTGAGCTCAGGTGACC

1339    GCTTTTGGAAGCCGAGGTGCAGGTTCCCAGATGTCTGGGTGCAGGACCTTGGCACGGAGC
        CAGGCTAGCTTGCCTGGCACTGCCGTTCTCCTGTGGACACAGCCAGGCCCCGCCCTCTCA
        GAGGCTTGGACGGGCGTGGGGGAGCAAAGCCAGCCGATGCTCTGGGAACCGACTCCCCGG
        GAGAAAACCCAGGCAGGCTGGGCAAGACTTCCGAGCGCAGGGATTTCATACAGGATCCTC
        CCTGCCTTTTCCCGCCCTCCACGCTCTAGGGAAGGAGGACTTCTGGAGTCCCTTCTCTGA
        [C,A]
        CCTGTGAGGGAGAGCAGCGCCAGCCAGGAGAAGGCTCCAGGTCATCAAGGCCTGGGAGGG
        GGAGGGAAGGGATCCCTCCTCCCTGCTCTCTAGGAGTAGAGATTGGCACCAGGGGCACGG
        GCCAGCACAGTGGATCCTGGGCATTTCTTCCAGCCTGGGTGTAGCCTGAATAGGGGTGCC
        CTTCCTCTCCCTGAAAGCACCTTTATTCCATGTCCTCAGCGGCAGAGCTGGGAGGAAAGG
        GAACCATCCCCCTCACTTTTGTAATTTCTGTCACCTGAGCTCAGGTGACCAGCTCAGGCC

1412    CTGGCACTGCCGTTCTCCTGTGGACACAGCCAGGCCCCGCCCTCTCAGAGGCTTGGACGG
        GCGTGGGGGAGCAAAGCCAGCCGATGCTCTGGGAACCGACTCCCCGGGAGAAAACCCAGG
        CAGGCTGGGCAAGACTTCCGAGCGCAGGGATTTCATACAGGATCCTCCCTGCCTTTTCCC
        GCCCTCCACGCTCTAGGGAAGGAGGACTTCTGGAGTCCCTTCTCTGACCCTGTGAGGGAG
        AGCAGCGCCAGCCAGGAGAAGGCTCCAGGTCATCAAGGCCTGGGAGGGGGAGGGAAGGGA
        [T,C]
        CCCTCCTCCCTGCTCTCTAGGAGTAGAGATTGGCACCAGGGGCACGGGCCAGCACAGTGG
        ATCCTGGGCATTTCTTCCAGCCTGGGTGTAGCCTGAATAGGGGTGCCCTTCCTCTCCCTG
        AAAGCACCTTTATTCCATGTCCTCAGCGGCAGAGCTGGGAGGAAAGGGAACCATCCCCCT
        CACTTTTGTAATTTCTGTCACCTGAGCTCAGGTGACCAGCTCAGGCCTGAGAAGGGAATG
        GGAGCAGAGAGGGTTTTATTGAAATCAGGTACTAGTCCTCTGGGAAGAATCCTCTTTTGG

2121    CCACTGCCTCCTGTTGTCATGGCAACTGGGAATTAGGGTTTTATCCAGCAGCACATGCCC
        AGGAAGGCAAAGGGAAGAAGGGTGGGGGTAACCCCCTGCCCTCTCCTGGGAGAACGAGG
        GAGCCACTCCTAGCCTGGGGAGGCCCTGGAATGGAAACTGGGGCTGTAGACTCCATGCTT
        GGTTCTGCCCAGAGCACTTGGTCTCCTTGTGCCAGCTCTGAGCTAAGAAAGGGAGAGAGG
        AGAGAGAGCCAGCCAGAGGGGCCGTGGAGAGGTAGATATCACTCTGTCAGCCCCCCAGAT
        [-,A]
        AATGTGGAACATCGGCGCTTTGGTAGGCCTAGGTTCCAGAAGCAAATAAAATCAATGTGG
        TTCTGACTCTCAGGGAACCTGCAGTCTAGGAGTACTCATGTTTTCTACTTTGGCTCAAAT
        TCTGGACTCTTTTATTATTTTTTAAATGACTTTTTTTTTTTTAAGACAGGTTCTTGCTCT
        GTTGCCCAGGCTGGAGTGCAGTGCGCAATCATGGCTTACCGTAGCCTCGACCTCCTGGG
        CTCAAGAGATCCCCCTGCCTCAGCCCCACAAGTAGCTGGGATCATAGGCATGCACCACCA

2264    CCCTGGAATGGAAACTGGGGCTGTAGACTCCATGCTTGGTTCTGCCCAGAGCACTTGGTC
        TCCTTGTGCCAGCTCTGAGCTAAGAAAGGGAGAGAGGAGAGAGAGCCAGCCAGAGGGGCC
        GTGGAGAGGTAGATATCACTCTGTCAGCCCCCCAGATAAATGTGGAACATCGGCGCTTTG
        GTAGGCCTAGGTTCCAGAAGCAAATAAAATCAATGTGGTTCTGACTCTCAGGGAACCTGC
        AGTCTAGGAGTACTCATGTTTTCTACTTTGGCTCAAATTCTGGACTCTTTTATTATTTTT
        [T,A]
        AAATGACTTTTTTTTTTTTAAGACAGGTTCTTGCTCTGTTGCCCAGGCTGGAGTGCAGTG
        GCGCAATCATGGCTTACCGTAGCCTCGACCTCCTGGGCTCAAGAGATCCCCCTGCCTCAG
        CCCCACAAGTAGCTGGGATCATAGGCATGCACCACCACACCTGGATAATTTTTAATTTTT
        TTGTAGAGATGGGGTCTCGCCATGTTGCCCAGGTGGCTCTCAAACTCCTGGGCTCAGGT
        GATTCTCCTGCCTCAGCCTCCTAAAGTGCTGGGATTATAGGCGTGAGCCACCTTGCTCAG

2278    CTGGGGCTGTAGACTCCATGCTTGGTTCTGCCCAGAGCACTTGGTCTCCTTGTGCCAGCT
```

FIGURE 3 K

```
         CTGAGCTAAGAAAGGGAGAGAGGAGAGAGAGCCAGCCAGAGGGGCCGTGGAGAGGTAGAT
         ATCACTCTGTCAGCCCCCCAGATAAATGTGGAACATCGGCGCTTTGGTAGGCCTAGGTTC
         CAGAAGCAAATAAAATCAATGTGGTTCTGACTCTCAGGGAACCTGCAGTCTAGGAGTACT
         CATGTTTTCTACTTTGGCTCAAATTCTGGACTCTTTTATTATTTTTTAAATGACTTTTTT
         [T,-]
         TTTTTAAGACAGGTTCTTGCTCTGTTGCCCAGGCTGGAGTGCAGTGGCGCAATCATGGCT
         TACCGTAGCCTCGACCTCCTGGGCTCAAGAGATCCCCCTGCCTCAGCCCCACAAGTAGCT
         GGGATCATAGGCATGCACCACCACACCTGGATAATTTTTAATTTTTTTGTAGAGATGGGG
         GTCTCGCCATGTTGCCCAGGTGGCTCTCAAACTCCTGGGCTCAGGTGATTCTCCTGCCTC
         AGCCTCCTAAAGTGCTGGGATTATAGGCGTGAGCCACCTTGCTCAGCCAAATTATAGTCT

2482     TTCTGACTCTCAGGGAACCTGCAGTCTAGGAGTACTCATGTTTTCTACTTTGGCTCAAAT
         TCTGGACTCTTTTATTATTTTTTAAATGACTTTTTTTTTTTTAAGACAGGTTCTTGCTCT
         GTTGCCCAGGCTGGAGTGCAGTGGCGCAATCATGGCTTACCGTAGCCTCGACCTCCTGGG
         CTCAAGAGATCCCCCTGCCTCAGCCCCACAAGTAGCTGGGATCATAGGCATGCACCACCA
         CACCTGGATAATTTTTAATTTTTTTGTAGAGATGGGGGTCTCGCCATGTTGCCCAGGTGG
         [C,G]
         TCTCAAACTCCTGGGCTCAGGTGATTCTCCTGCCTCAGCCTCCTAAAGTGCTGGGATTAT
         AGGCGTGAGCCACCTTGCTCAGCCAAATTATAGTCTTACCCTCTAAAAATTCTACTTGTT
         TCCTCTTCAAAAAACAAACAAACAAAAAATACAACAGGAAGAAACACTTTATTTATATAC
         TTATTTTTGAGTCATAAAACCTGGATTTTCATTTTAGCTCTCCTTATTAGCTTTGTGAAC
         TTGGGCAAATCAGTTAACCTCCCTTATCCTCCCTGGTCTCCTCCTCCTCAGAGAAATAGG

2584     AAGACAGGTTCTTGCTCTGTTGCCCAGGCTGGAGTGCAGTGGCGCAATCATGGCTTACCG
         TAGCCTCGACCTCCTGGGCTCAAGAGATCCCCCTGCCTCAGCCCCACAAGTAGCTGGGAT
         CATAGGCATGCACCACCACACCTGGATAATTTTTAATTTTTTTGTAGAGATGGGGGTCTC
         GCCATGTTGCCCAGGTGGCTCTCAAACTCCTGGGCTCAGGTGATTCTCCTGCCTCAGCCT
         CCTAAAGTGCTGGGATTATAGGCGTGAGCCACCTTGCTCAGCCAAATTATAGTCTTACCC
         [G,T]
         CTAAAAATTCTACTTGTTTCCTCTTCAAAAAACAAACAAACAAAAAATACAACAGGAAGA
         AACACTTTATTTATATACTTATTTTTGAGTCATAAAACCTGGATTTTCATTTTAGCTCTC
         CTTATTAGCTTTGTGAACTTGGGCAAATCAGTTAACCTCCCTTATCCTCCCTGGTCTCCT
         CCTCCTCAGAGAAATAGGCGAGTAATACCTGCTCTTCCTGCTTCCCAGGACCGTTGGAAT
         CATTGTTGTTCTCCAACCCCCACTTTCTGGGCAGCACCTTCTCCCCTACCTTTCTGGCTC

2816     CTCAGCCTCCTAAAGTGCTGGGATTATAGGCGTGAGCCACCTTGCTCAGCCAAATTATAG
         TCTTACCCTCTAAAAATTCTACTTGTTTCCTCTTCAAAAAACAAACAAACAAAAAATACA
         ACAGGAAGAAACACTTTATTTATATACTTATTTTTGAGTCATAAAACCTGGATTTTCATT
         TTAGCTCTCCTTATTAGCTTTGTGAACTTGGGCAAATCAGTTAACCTCCCTTATCCTCCC
         TGGTCTCCTCCTCCTCAGAGAAATAGGCGAGTAATACCTGCTCTTCCTGCTTCCCAGGAC
         [C,T]
         GTTGGAATCATTGTTGTTCTCCAACCCCCACTTTCTGGGCAGCACCTTCTCCCCTACCTT
         TCTGGCTCGTCCTGAAGGGGAGGCTCTTCCTATTCCCTTCCCCATTGCTTTGCCCTTGTA
         TCTGCTCATCCTCCTCTCTCCCCTCTCCAGGAGAGACGTTTCAGAGCCCTTGCCTCCTTC
         ACCATGCCGGTTGCCGCCACCAACTCTGAAACTGGTAAGAAGGGGGTGAGGATGTTAGCT
         TATTTCAGTGGTTCAGAGGGTGCCAGGCGAGGACTTAGGGGTGGGCACTTGCACAGCTCC

3424     AACCAACTGGCTCCACTGCTGTCCACCCTACCACTCAGCCATTCCTTCTGGCAGCTGCTG
         TGGCCATCTCCTCTGTGTGGGTTCCTGTGCTGGAACGGAGAAGAGAAAGAATAAGACCCA
         TACCTGCTCCAGTGTAGGGCTGGAGCACAACTCACCTCCGTGGAGGGCAGGGGATGCATG
         CTCCAGAGGTGACCCGTACTATTGCTGGAGGGCAGTGGCATAGGACCAGGCCTTCAGGAG
         GTGGCCCCGGAGCTGGGCCTTGGAGAATGGCTTGGGGGTGGAGGGATTACAGCAGCACAG
         [C,T]
         CTGGGGCTGAGAAGTCCATAATCGCTGCCCACTAGGCCAGCATGTGCCAGAGGTGGACAG
         GGGGTACTGGGGACCAGGAAGCTGTGAGTGAAGGAACAAGAATACCAGGTTAGGATACCT
         GGACGTGGCTCTGTAGGAGGCATTAGGACAAGGGAGTGGGCCACTCAGACAAACTAGCAA
         AGCCTCAGTGGCAAACTGCTTAACCTCTTGGAGCTCGCATTTCTTCTTCTGTAAAGAGGC
         TGCTGTGAGACGCAAAGGCTGTAATGGGAGAGCACATTACTTTTAGGAATAGTCATAATT

3528     GAAAGAATAAGACCCATACCTGCTCCAGTGTAGGGCTGGAGCACAACTCACCTCCGTGGA
         GGGCAGGGGATGCATGCTCCAGAGGTGACCCGTACTATTGCTGGAGGGCAGTGGCATAGG
         ACCAGGCCTTCAGGAGGTGGCCCCGGAGCTGGGCCTTGGAGAATGGCTTGGGGGTGGAGG
         GATTACAGCAGCACAGCCTGGGCTGAGAAGTCCATAATCGCTGCCCACTAGGCCAGCAT
         GTGCCAGAGGTGGACAGGGGGTACTGGGGACCAGGAAGCTGTGAGTGAAGGAACAAGAAT
         [A,G]
         CCAGGTTAGGATACCTGGACGTGGCTCTGTAGGAGGCATTAGGACAAGGGAGTGGGCCAC
         TCAGACAAACTAGCAAAGCCTCAGTGGCAAACTGCTTAACCTCTTGGAGCTCGCATTTCT
         TCTTCTGTAAAGAGGCTGCTGTGAGACGCAAAGGCTGTAATGGGAGAGCACATTACTTTT
         AGGAATAGTCATAATTATTATGCTGCTGTTGCTGCCGCTGCCACCAAGTTGTTGTTGTTG
         TTTTTGAGACAAGTTCTGGCTCTTTAGCCTAGGCTGGAGTGCAGTGGCGCAAGCTTGGCT

3581     CCGTGGAGGGCAGGGGATGCATGCTCCAGAGGTGACCCGTACTATTGCTGGAGGGCAGTG
         GCATAGGACCAGGCCTTCAGGAGGTGGCCCCGGAGCTGGGCCTTGGAGAATGGCTTGGGG
         GTGGAGGGATTACAGCAGCACAGCCTGGGCTGAGAAGTCCATAATCGCTGCCCACTAGG
         CCAGCATGTGCCAGAGGTGGACAGGGGGTACTGGGGACCAGGAAGCTGTGAGTGAAGGAA
         CAAGAATACCAGGTTAGGATACCTGGACGTGGCTCTGTAGGAGGCATTAGGACAAGGGAG
         [T,C]
         GGGCCACTCAGACAAACTAGCAAAGCCTCAGTGGCAAACTGCTTAACCTCTTGGAGCTCG
         CATTTCTTCTTCTGTAAAGAGGCTGCTGTGAGACGCAAAGGCTGTAATGGGAGAGCACAT
```

FIGURE 3 L

```
        TACTTTTAGGAATAGTCATAATTATTATGCTGCTGTTGCTGCCGCTGCCACCAAGTTGTT
        GTTGTTGTTTTTGAGACAAGTTCTGGCTCTTTAGCCTAGGCTGGAGTGCAGTGGCGCAAG
        CTTGGCTCACTGCAACCTCTGCCTACCAGCCTCAAGTCATTCTCCCACCTCAGCCTCCCA

3784    GGGGGTACTGGGGACCAGGAAGCTGTGAGTGAAGGAACAAGAATACCAGGTTAGGATACC
        TGGACGTGGCTCTGTAGGAGGCATTAGGACAGGAGTGGGCCACTCAGACAAACTAGCA
        AAGCCTCAGTGGCAAACTGCTTAACCTCTTGGAGCTCGCATTTCTTCTTCTGTAAAGAGG
        CTGCTGTGAGACGCAAAGGCTGTAATGGGAGAGCACATTACTTTTAGGAATAGTCATAAT
        TATTATGCTGCTGTTGCTGCCGCTGCCACCAAGTTGTTGTTGTTGTTTTTGAGACAAGTT
        [C,G]
        TGGCTCTTTAGCCTAGGCTGGAGTGCAGTGGCGCAAGCTTGGCTCACTGCAACCTCTGCC
        TACCAGCCTCAAGTCATTCTCCCACCTCAGCCTCCCAAGTAGCTGGGACTACAGGTGTGC
        ACCACCATGCCCAGCTAATTTTTGTATTTTTCGTAAAGACAAAAATGTTGCCCATGCTGG
        TCTCAAACTCCTGAGCTCAAGTACTCCACCCGCCTCGACCTCCCAAACTACTGGGATTAC
        AGGTGTGAACCACTGTGCCTGGCCTGAGTTGTTATTTTGGCATTAACCCTGTGTCCTTGA

4170    CTCAGCCTCCCAAGTAGCTGGGACTACAGGTGTGCACCACCATGCCCAGCTAATTTTTGT
        ATTTTTCGTAAAGACAAAAATGTTGCCCATGCTGGTCTCAAACTCCTGAGCTCAAGTACT
        CCACCCGCCTCGACCTCCCAAACTACTGGGATTACAGGTGTGAACCACTGTGCCTGGCCT
        GAGTTGTTATTTTGGCATTAACCCTGTGTCCTTGAAACAGTCACCTCCTTTTGAAGACCT
        GAGATTTCCCTAAGATGAGATGATGGGACAAGATCAGTGTTCTTAACTTTTTTCTTTTTC
        [-,T]
        TTTTTTTTTTTTTGAGATGGAGTCTCCCTCTGTTGCCCAGGCTGGAGGGCAGTGGTGGGAT
        CTCGGCTCACTGCAACCTTCACCTCCCAGGTTCAAGTGATTCTCCTGCCTCAGCCTCCCA
        AGTAGCTGGGATTACAGGCACCTGCTATCATGCCCAGCTAATTTTTGTATTTTTGTAGAG
        ACTGGGTTTCACCATGTTGGCCAGGCTGTCCTGACCTCAGGTGATCCACCTGCCTTGGCC
        TCCCAAAGTGCTGGGATTACAGGCATGAGCCACCACACCTGGCCTGTTCTTAATTTTATT

4526    GGGATCTCGGCTCACTGCAACCTTCACCTCCCAGGTTCAAGTGATTCTCCTGCCTCAGCC
        TCCCAAGTAGCTGGGATTACAGGCACCTGCTATCATGCCCAGCTAATTTTTGTATTTTTG
        TAGAGACTGGGTTTCACCATGTTGGCCAGGCTGTCCTGACCTCAGGTGATCCACCTGCCT
        TGGCCTCCCAAAGTGCTGGGATTACAGGCATGAGCCACCACACCTGGCCTGTTCTTAATT
        TTATTGGTCCTGAGTCACTTAGAATCTGGTGACAGCAGTGAGCCCTCATCGTAGACATAT
        [A,G]
        CATCCATGCACAAAAGGTATATTCTACTCTAGGGGATCATGGATTCCCGTAGTGCACGCA
        GGACCCCAGAAGGTTAAGTTCCCTGTGCTAGAGGCCCTCTGAGGCCCGGGCAGCTGGGAA
        CTGCTATGGTTCTGCTCTGAGTTGTCTGAACTTCCCCCTGCCTGGATGCCTCCCTCCCAT
        GCAGCTCCTTCCCTTGCTCTAGGCCCCACTACTGCCTCTGCCAGAGGTTCCAGGGCTGCC
        ACTTTGGGTAGAATGATTCCTCTGTGCCTCCTCTCCGAGAAAGTGAAGGGAGTGAGCCAG

4579    CTCAGCCTCCCAAGTAGCTGGGATTACAGGCACCTGCTATCATGCCCAGCTAATTTTTGT
        ATTTTTGTAGAGACTGGGTTTCACCATGTTGGCCAGGCTGTCCTGACCTCAGGTGATCCA
        CCTGCCTTGGCCTCCCAAAGTGCTGGGATTACAGGCATGAGCCACCACACCTGGCCTGTT
        CTTAATTTTATTGGTCCTGAGTCACTTAGAATCTGGTGACAGCAGTGAGCCCTCATCGTA
        GACATATACATCCATGCACAAAAGGTATATTCTACTCTAGGGGATCATGGATTCCCGTAG
        [C,T]
        GCACGCAGGACCCCAGAAGGTTAAGTTCCCTGTGCTAGAGGCCCTCTGAGGCCCGGGCAG
        CTGGGAACTGCTATGGTTCTGCTCTGAGTTGTCTGAACTTCCCCCTGCCTGGATGCCTCC
        CTCCCATGCAGCTCCTTCCCTTGCTCTAGGCCCCACTACTGCCTCTGCCAGAGGTTCCAG
        GGCTGCCACTTTGGGTAGAATGATTCCTCTGTGCCTCCTCTCCGAGAAAGTGAAGGGAGT
        GAGCCAGGGCCTAAACTGTGGTACACTTGTCCAGGAAAGGCCTCTTCTCCTTGCAGTGGA

4730    CAGGCATGAGCCACCACACCTGGCCTGTTCTTAATTTTATTGGTCCTGAGTCACTTAGAA
        TCTGGTGACAGCAGTGAGCCCTCATCGTAGACATATACATCCATGCACAAAAGGTATATT
        CTACTCTAGGGGATCATGGATTCCCGTAGTGCACGCAGGACCCCAGAAGGTTAAGTTCCC
        TGTGCTAGAGGCCCTCTGAGGCCCGGGCAGCTGGGAACTGCTATGGTTCTGCTCTGAGTT
        GTCTGAACTTCCCCCTGCCTGGATGCCTCCCTCCCATGCAGCTCCTTCCCTTGCTCTAGG
        [C,T]
        CCCACTACTGCCTCTGCCAGAGGTTCCAGGGCTGCCACTTTGGGTAGAATGATTCCTCTG
        TGCCTCCTCTCCGAGAAAGTGAAGGGAGTGAGCCAGGGCCTAAACTGTGGTACACTTGTC
        CAGGAAAGGCCTCTTCTCCTTGCAGTGAAGGGATGGCACCAATGTCCCCAGCTTCTGCAG
        CATCAGAGGGCTCAGTCCCCCATCTCCTGTCCAGCCTGCTGGGCTCCCTGGGGTCTCCCT
        GCCTCTTTCAGCCTGCCTAGGCCCCACTGTAAGCTGCTTAGGCATTAATTAAACCCACCC

5060    GGCTGCCACTTTGGGTAGAATGATTCCTCTGTGCCTCCTCTCCGAGAAAGTGAAGGGAGT
        GAGCCAGGGCCTAAACTGTGGTACACTTGTCCAGGAAAGGCCTCTTCTCCTTGCAGTGGA
        GGGATGGCACCAATGTCCCCAGCTTCTGCAGCATCAGAGGGCTCAGTCCCCCATCTCCTG
        TCCAGCCTGCTGGGCTCCCTGGGGTCTCCCTGCCTCTTTCAGCCTGCCTAGGCCCCACTG
        TAAGCTGCTTAGGCATTAATTAAACCCACCCCTGAGCCTGTGCTTAATGGCCTCTCCAGC
        [C,T]
        GGGACTGCCCAGTAAACCCACCAATAGTGCCTGACTGGGGCGTAGGAGGAGGAGCAAGCC
        CAGCAATTTGGCTTCGTTGTTGCAGACCACTTGATGGGGGCGTGGTGGGGAGGATGGGG
        GACAGGGAGTGGAGACTTGGGGTGTGGCGGTGGGTTCTGCTTCCTCAAAGGACTCCTGGG
        GCTCCTGCTCCCCTTCATGTTGTTCGAGGGGCTGCTCCTGGCTTCTCATATTCAAAGGAA
        GAAGTACAAAGTGTTTTTCTTCCTTCAGGCAGCCTCTGTCCTATCCTGAGCTACATTAGC

5195    TCCCCAGCTTCTGCAGCATCAGAGGGCTCAGTCCCCCATCTCCTGTCCAGCCTGCTGGGC
        TCCCTGGGGTCTCCCTGCCTCTTTCAGCCTGCCTAGGCCCCACTGTAAGCTGCTTAGGCA
        TTAATTAAACCCACCCCTGAGCCTGTGCTTAATGGCCTCTCCAGCCGGGACTGCCCAGTA
```

FIGURE 3 M

```
        AACCCACCAATAGTGCCTGACTGGGGCGTAGGAGGAGGAGCAAGCCCAGCAATTTGGCTT
        CGTTGTTGCAGACCACTTGATGGGGGCGTGGTGGGGGAGGATGGGGGACAGGGAGTGGAG
        [A,C]
        CTTGGGGTGTGGCGGTGGGTTCTGCTTCCTCAAAGGACTCCTGGGGCTCCTGCTCCCCTT
        CATGTTGTTCGAGGGGCTGCTCCTGGCTTCTCATATTCAAAGGAAGAAGTACAAAGTGTT
        TTTCTTCCTTCAGGCAGCCTCTGTCCTATCCTGAGCTACATTAGCTCCCAGCTTCAAAAA
        TCTAATGGTGGATTCTGCCCCTTATTATCTGGTGGTCATTATACTTCCCACAGGATAGAG
        AGACAGCTGTGTCCCTGCCTCTGAGTTCAGGCTCCCCTTCCCTCCTCCTCCCCTGGGAGA

6070    TTTTTGGATCAAGGCTGGGATATGTGGCTGCTTTCAGGTGGAGCTGTCCCTTTAAATCTC
        TCCTCCATCCCTGGGTTACTGTCCTGGTGTGTAATTCTACTGTCATGGCAACCAGGGGTG
        CAATGCGACCTGGTGCCACTCCTCAGGGAATGTCTGAGTGGAGGCTGCAGTACCCTGATG
        GTGGCCTCTTGGGCACAAGATCTCAGAGGAATGGGGTCACCGGAGCGGAGCTGAGTCCTT
        CCCTTCTGCCCACACTTTTCCCTGTGTGCAAATGTGCCCTCATTTTTCCTTTCTGGGGAA
        [C,A]
        TGAGTTCCAAGTATGCCTGACTTGCTTCCTGGGCATCATCCCCTTCATTAAGAGGAAGAA
        CTCATGGGAGATGGGGGAGGGGAAGAAGCTGCTGTGAGGCGAGGGGTAAGCAGGGCTGGG
        GCACCATCCCTACCCACAGCGATGCCACCTCCCCCACGTACCCTGCCTCCCAGTGGCTGA
        CCAAGGGTGGGTAGGGGGAGGCGTCTGAGGCTTGAGGTATTTGCCCCATGCCCAAGTGAG
        GCTGCCTCCCGGTGGAGGGCTGAGTCGTTCTTGGGGACTTCCTTAGACTGAGGGACTATT

7829    ATGGTGGCAGAGTAATGATACCCTTCGCCCATCTCTGCCCCCAGCTGGGCACATTCTGCT
        TCTCGCTTCCTTTCCCCGGAACTTGCCACAGCCTGGAACTCCCACCTCTGTCAGTGAGTG
        AAGGCAGCCCTCACCTCAGGTCTCGGGGGCATTGTTGCGGCCCAGCTGCAGGTGTTATCG
        TGTCCTCCATTATGTCCCATTTCGGGCTGAGAGTTTTGCTTATCCCTGTGATGACTTGGTG
        TGACCTCAGCCTTTGGGTCACACCAAGGCCTCCAGTGCCTGTTTCCCTAGCTCCTGCCAG
        [C,G]
        GTTCCAGGCCTCAGCTTTGACTTCCTATCATCCATGTTAATTTCTCAGTGATTATAGATC
        ATTGTCACTCAGAGCTGAAGGCCTGTAAACATCATCTAGCCCAATCCATCCATTTTACAG
        GCAGGAAAGACTGAGGCCAGTGAGGGACAGTGACTTGTACAATGTCACACTGAATTAGTG
        GTGCTTAGACTGGAGGCTGCAGGCCCTGGCTCCTGTGTGGCTGCCTGCTTGACTCTGGGC
        CTGTACTCACGGACTTGCTCCGAGTACTGTCTGTCTCATCCTTGAGCCTGCCAGGTACAG

7899    TTTCCCCGGAACTTGCCACAGCCTGGAACTCCCACCTCTGTCAGTGAGTGAAGGCAGCCC
        TCACCTCAGGTCTCGGGGGCATTGTTGCGGCCCAGCTGCAGGTGTTATCGTGTCCTCCAT
        TATGTCCCATTTCGGGCTGAGAGTTTTGCTTATCCCTGTGATGACTTGGTGTGACCTCAGC
        CTTTGGGTCACACCAAGGCCTCCAGTGCCTGTTTCCCTAGCTCCTGCCAGCGTTCCAGGC
        CTCAGCTTTGACTTCCTATCATCCATGTTAATTTCTCAGTGATTATAGATCATTGTCACT
        [C,G]
        AGAGCTGAAGGCCTGTAAACATCATCTAGCCCAATCCATCCATTTTACAGGCAGGAAAGA
        CTGAGGCCAGTGAGGGACAGTGACTTGTACAATGTCACACTGAATTAGTGGTGCTTAGAC
        TGGAGGCTGCAGGCCCTGGCTCCTGTGTGGCTGCCTGCTTGACTCTGGGCCTGTACTCAC
        GGACTTGCTCCGAGTACTGTCTGTCTCATCCTTGAGCCTGCCAGGTACAGGTGGCTGAGC
        CCTGGGCTTCAGCCCATCTAGAGGTTGAGTGAGGAGCTTGTGGTTTTCTTTTCTTTTTCT

8880    AGTTCTCCTGCCTCAGCCTCCTGAGTAGCTAGAATTACAGACCTACACCACTATGCCTGG
        CTAATTTTGGTATTTTTAGTAGAGATGGGGTTTTGCCTTGTTGCCCAGGCTGGTCTTGAA
        CTCCTGGCCTCAAGTGATCCACCCAACAGCTTGTGGTTTTCTGGTGCAGGGCAGGATCTG
        CAACCTGACACCTGCTTCCCTTTCTCCCTTCTCTCCACCTCAGAGTCTCTTCCAGCTGCC
        TGGAGCCTCCCACCTGCTCAGGCTGGCATTACCTAGGGTGGAGAGAACAGGCCAAGGAAA
        [C,T]
        TGTCCCCTTCCTCCAGGATCCCTGTCCCAGGCATTCAAGGGCCTGGGGTGCCTGTGCTGG
        GCAGGGAGGGGAATGTTGCTGGGGAGGGGAATGTTGCCGGGGAGGGGCTGCCTTCTGTGG
        GACATGGGGGTGGGGAAGTGGCAAGTATTGTGGTGTGTTTTGGTCTTCTGTACCCAGCTG
        GTACCTGTGTATCTCACTGCCCGTACCTTCCCCCAGCCATGCAGCAAGTCCTGGACAACT
        TGGGATCCCTCCCCAGTGCCACGGGGGCTGCAGAGCTGGACCTGATCTTCCTTCGAGGCA

8978    TGTTGCCCAGGCTGGTCTTGAACTCCTGGCCTCAAGTGATCCACCCAACAGCTTGTGGTT
        TTCTGGTGCAGGGCAGGATCTGCAACCTGACACCTGCTTCCCTTTCTCCCTTCTCTCCAC
        CTCAGAGTCTCTTCCAGCTGCCTGGAGCCTCCCACCTGCTCAGGCTGGCATTACCTAGGG
        TGGAGAGAACAGGCCAAGGAAACTGTCCCCTTCCTCCAGGATCCCTGTCCCAGGCATTCA
        AGGGCCTGGGGTGCCTGTGCTGGGCAGGGAGGGGAATGTTGCTGGGGAGGGGAATGTTGC
        [C,T]
        GGGGAGGGGCTGCCTTCTGTGGGACATGGGGGTGGGGAAGTGGCAAGTATTGTGGTGTGT
        TTTGGTCTTCTGTACCCAGCTGGTACCTGTGTATCTCACTGCCCGTACCTTCCCCCAGCC
        ATGCAGCAAGTCCTGGACAACTTGGGATCCCTCCCCAGTGCCACGGGGGCTGCAGAGCTG
        GACCTGATCTTCCTTCGAGGCATTATGGAAAGTCCCATAGTAAGATCCCTGGCCAAGGTA
        CAGTGCTCCAGGGAGGTGGGCACAAGGGCACTGTGCTTGGGGAGGCACAGTAGGGGATGG

9594    GGGCTTTGGGAATGGGACATGTGGCACAAGAGGCCCCCCTGAAGGGGATTGTAGAAGAAA
        ATCATGCCCAGGTGATGACCTGAGTGGCTGCAGGTAGAGGGGGCTGCCCCCACACCTGTC
        TGGTGAGTGCGTGGGTGGATGTTTGTTGACTGCCAGCTTGTGGAGTGTGTGATTGGTGCG
        GGCTAGCATGCACATGTTGGAGAATCTCTAGAATTCATCTTGCCTGTCCTTCTGCCTTTG
        GGCGTTTTGTGTGTATGTCTTTCTAAGGTCACCTGCCATGTATCAGGTTGGGGAGAGATT
        [G,C]
        ACTAAAAGAGAAAATTATAGGACAATTTGGTAATGACAGTGATAGAGGTGGATACACTAT
        GCATTTTGGGAGCATAAAGGACAGGTGTCTAACCCAGCCTGGGGTGGGTGAGGAGGGCTT
        CCTGGAGGAAGGACCACTTGAGCTGAGTGGAAGAATGAGGAAGAGGGGGAGGGCATTCTG
        GGCCACAGAAGAGCTTGAGCAGAAGCACAGAGGTAAGAAAGAGTCAGGAGTGTGCAGGGG
```

FIGURE 3 N

```
         ATTGGAAGGGCTGGTGTGAGGCTGAGCCTCAAGTGTAAGACAATGCGAGCTGTGCAAAGG
11334    AGACCAAGGTCAGAGGAAGGGAGGTAGGAGGTGAAAGTTTTCCAAGGAGGACAGTTCTAG
         GGATGCCATGATAATGTAGGGTGGGGCTGCAGTGGACAGGTAGGTCATCAGTGTTGAAGA
         CACCCAGAAATGGAAGGCTCAGGAGTGGGATGGGCTTGTCCACACACCTATTGGCATGTA
         GGGCTATGGCAGGCGTCAGGGTGGGGAGAAGACTGAGGCAGTCCCCAGGGTTTTCAGTGC
         ATGGTGGTGGAGGTGACCAGGAAGTCGGCAATGACAGCAAGGGTAGGGAGAAAGAAGGTA
         [T,C]
         AGCCAGGTGGTGGGTTTTCTGTAGAGCGGGGACTCTGTCACAGGCTGGCTATGGCTGGCC
         CTGGCATGGGATGTGGAGGACCACGTCCCACTGGAGTGGGGATTGCTGCTGCAGGGGACA
         CCATGTCCTTGGGTTGTAGCCTATTCACATTATCTGTGGAATGGTTGAAGACTTGGGAAG
         ATTGTTAACAGCGAAAGATGAAAAGTTGCAGAGGTTTAATAGTGGGAAGTTCTGGGGAAG
         AGAAAACTGAGCAGATTGGAGGAGATTGGAGAAAGGCAGGGTGCTTTTCATTCAGCAATC

11467    AAGGCTCAGGAGTGGGATGGGCTTGTCCACACACCTATTGGCATGTAGGGCTATGGCAGG
         CGTCAGGGTGGGGAGAAGACTGAGGCAGTCCCCAGGGTTTTCAGTGCATGGTGGTGGAGG
         TGACCAGGAAGTCGGCAATGACAGCAAGGGTAGGGAGAAAGAAGGTACAGCCAGGTGGTG
         GGTTTTCTGTAGAGCGGGGACTCTGTCACAGGCTGGCTATGGCTGGCCCTGGCATGGGAT
         GTGGAGGACCACGTCCCACTGGAGTGGGGATTGCTGCTGCAGGGGACACCATGTCCTTGG
         [G,A]
         TTGTAGCCTATTCACATTATCTGTGGAATGGTTGAAGACTTGGGAAGATTGTTAACAGCG
         AAAGATGAAAAGTTGCAGAGGTTTAATAGTGGGAAGTTCTGGGGAAGAGAAAACTGAGCA
         GATTGGAGGAGATTGGAGAAAGGCAGGGTGCTTTTCATTCAGCAATCGAAGATCCTACTC
         ATTTACTAAAGATAAAGACAAGAAGCTGGGAGTAGGGGCATGCACCTGTAGTCCCAGCTA
         CTCTGGAGGCTGAGGTGAGAGCATTGCTTGAGGCCAAGAAGCTCAAGTGCAGTTCATGTA

12353    TATGAGGCACACGGCACGGTGTGGCTTACAGCTTTAGTCCCAGCACTTTGGGAGACCAAG
         GTGGGTGGATCATTTGAGCTCAGGATTTCAAGACCAGCCTGATCAACATGGTGAAATCCT
         GTCTCTATAAAAAAATAGAATTAGCTAAGCATGGTGGCATTCACCTGTAGTCCCAACTAC
         TCAAGAGGCTGAGGCAGGAGAGTTGCTTGAGCTGGGTAGGTCGAGGCTACAATGAGCCAT
         GATCATGCCACTACAGTCCAGCCTGGGTGACCGAGTGAGACACTGTCTCAAAAAAAAAAA
         [T,A]
         AAATAAATAAATAAAAAGTTTGGCACAGTTAATGCCTCTCCCCTTCCTCATTTTCACTGC
         ATTCCCTTCCCACAGGTAACCACTGCCTAGAGATTGATGTCATTTCATTGAATGTTGGCT
         TATCTTGCCTACATATGTGTTTAGCTGTAAACAATATACCTTTGTGGGATTTTTTTTTAG
         ACAGGGTCTTATTCCATCTCCCAGGTTGGAGTACAGTGGAACAATTATAGCTCACTGCAG
         CCTGGAACTCCTGGGCTCAAATGATCCTCCTGCCCTCCTGCCTTAGCCTCCTGAGTAACT

12538    AGGCTGAGGCAGGAGAGTTGCTTGAGCTGGGTAGGTCGAGGCTACAATGAGCCATGATCA
         TGCCACTACAGTCCAGCCTGGGTGACCGAGTGAGACACTGTCTCAAAAAAAAAAATAAAT
         AAATAAATAAAAAGTTTGGCACAGTTAATGCCTCTCCCCTTCCTCATTTTCACTGCATTC
         CCTTCCCACAGGTAACCACTGCCTAGAGATTGATGTCATTTCATTGAATGTTGGCTTATC
         TTGCCTACATATGTGTTTAGCTGTAAACAATATACCTTTGTGGGATTTTTTTTTAGACAG
         [A,G]
         GTCTTATTCCATCTCCCAGGTTGGAGTACAGTGGAACAATTATAGCTCACTGCAGCCTGG
         AACTCCTGGGCTCAAATGATCCTCCTGCCCTCCTGCCTTAGCCTCCTGAGTAACTGGGGC
         TACAAATATGTACCACCATGCCTGGCTAATCTTTAAATTTTTTTGTAGAGGCAGGGTCTT
         GCTACATTGTCCAGGCTAGTCTCAAACTCCTGGCCTCAAGTAATCCTCTCAGCCTCCCAA
         AGCACTGGGATTATAGGCATGAGCCACCATGACTGGCTCTACCTTTGTTATGTGTGCTTT

13471    AGGACTACAGGCATGCGCTACCATGCCCAGCTAATTTTTGTATTTTTAGTAGAGATGGGG
         TTTCACCATGTTGGCCAGGATGGTCTCGATCTCTTGACCTCGCAATCCGCCTGCCTTGGC
         CTCCCAAAGTGATGGGATTATAGGTGTGAGCCACCGCACCTGGCCATTTTTGTATTTTTT
         TTTTTTTTTTTTAGTAGAGACAGGGTTTCACCATATTGGCCAGGCTGGTCTTGAACTCCTG
         ACCTCATGATTCGCCTGCCTCAGCCTCCCAAAGTGCTGGGATTACAGGCGTGAGCCACCA
         [T,C]
         GCCTGGCCATTACGTGTGCTTTTAAATTTTATATAAATGAAATGATAGTGTAAGGTGCTT
         CTGTTTTTGAGATTTCTATTTCATACAAGTAGTACAGCTATCGACCTAAGTATAGATATA
         GATAGAGATAGGGAGATTCATTTGAACTGCGGTGTGGTGTTCTGATACAGCAGTCCCCAA
         CCTTTTTGGCACCAGGGACCAGTTTTGTGGAAGACAATTTTTTCCACGGATCAGGGTGAGG
         GGGGTGGTTTTGGTATGCAACTGTTCCACTCAGATCATCAGGCATTTGTTAGACTTCTCA

13969    ACCAGTTTTGTGGAAGACAATTTTTTCCACGGATCAGGGTGAGGGGGGTGGTTTTGGTATG
         CAACTGTTCCACTCAGATCATCAGGCATTTGTTAGACTTCTCATAAGGAGCACACAACCT
         AGATCCCTGGCACGTGCAGTTCACGGTAGGGTTGGTGCCCCTGTGAGAATCTAATGCCAC
         CACTGATCTGACAGGAGGTGGAGCTCAGGCAGTAATGCTTGCTCACCTCCTGCTGTTCAC
         CTACTTCCTAACAGGCCACGGATCACTACTGGTCCATGGCTTGGGGGTTGGGGACCCCTG
         [C,G,T]
         TCTAATATATGAATAGAGCTGTTTGTTTATTGGTTCCCTTCCTGAGAGATGTGTATGTCA
         CTGCTGATTTTGCTGTCTTAAAAACAGTGCTGCAGTGAACATCCTCATATCCATCTGCTT
         CTGCATGCATATGAGGGTTTCTCTAGAATGGACACTTGGCAATGAAATTGATGAATATGT
         GCAGTTTTGAACCTCAACATCTGTAACTTTCCAAAATTGATTTCAGAGTTGGGTTTATGA
         GCCCACATCACCTCTGGGTACTTTAGCTATTGTCTCCACAGTGAGACAGTGAGACTCTGC

14560    GAGACTCTGCTTTGTGATGGCAGAGTCTCAGAATGAGACAGCCCTCTTGCCAATACCCTT
         CAAAGCAGGGTCCCCCTTGATAGCATTCCTCTCTGGTCCAGTCCACTCGACAGTCCACTC
         GACAGCTCTCTAATGATGGGTTTGCTGGCTGGCTGGCTATGTCATTCACTCATTTGTCCA
         TCCATCCATCCATCCATCCATCCATCCATCCATCCATCAAATACCTATTTTGCACTCGCC
         ACATACCAGGCACAGTGCTGGGGTTATGGCAGTGAACTGCCAGATAGTTTGTTTTCCTGA
```

FIGURE 3 O

```
              [T,A]
       GAAGCCCAAGTCTGTCTTCCTTTCACTGGACACCACAATGCCCCAGTCCTGGGACCTCAC
       AGTAAAGCCTAATTGAAAATGAACCAATGTGCTGTGTCACATTGTAAGTAAACTCCCTTC
       TCTGGAAACGTTTTTGGCGAGAAGCTGGTCAGGATTTTTTCCAAGAAATTCCTGGTATGG
       TTCCGGATTTGTAGAGCACAATAGAAGAGAGTATGGACGTTTCTTCCCCTCTGAGACCCC
       CAGTATGAGGCTAATGGGCTAAGGCAATCCAGTAACTTCTTTCTCCCTGTGGTTGTGAAA

14637  TGATAGCATTCCTCTCTGGTCCAGTCCACTCGACAGTCCACTCGACAGCTCTCTAATGAT
       GGGTTTGCTGGCTGGCTGGCTATGTCATTCACTCATTTGTCCATCCATCCATCCATCCAT
       CCATCCATCCATCCATCCATCCATCAAATACCTATTTTGCACTCGCCACATACCAGGCACAGTG
       CTGGGGTTATGGCAGTGAACTGCCAGATAGTTTGTTTTCCTGATGAAGCCCAAGTCTGTC
       TTCCTTTCACTGGACACCACAATGCCCCAGTCCTGGGACCTCACAGTAAAGCCTAATTGA
       [A,G]
       AATGAACCAATGTGCTGTGTCACATTGTAAGTAAACTCCCTTCTCTGGAAACGTTTTTGG
       CGAGAAGCTGGTCAGGATTTTTTCCAAGAAATTCCTGGTATGGTTCCGGATTTGTAGAGC
       ACAATAGAAGAGAGTATGGACGTTTCTTCCCCTCTGAGACCCCCAGTATGAGGCTAATGG
       GCTAAGGCAATCCAGTAACTTCTTTCTCCCTGTGGTTGTGAAACAAACAGGAAGTGAATC
       TCCATAAAGGAGCCTACCTGAGCCCACTGGAAAAAAAAAAGCCATTCATTTCTTCTGTCC

15797  CATTCAGAAATTCAGAAAAATTGTTACTAATGGGGACAGCTGAGAGGCATGTGAAGGCTG
       TTGTGAACTAATTCACATGGAGATGAAGAAGAAAGAACACAGGGCTTGAGTCAGAAGATT
       CCACTGACCAGCTTTGTGAGTTTGGTATATCTGTCAACCTCTCTGAACTTCAGTTATTTC
       TTATGGAGGAATTTTTAAAAAATTAATATTTCTTTATGTATTTATTTTAAAAGAAAGGTG
       AGGTCTCACCGTGTTGCCCAGGCTGGTCTTGAACTCCTGAGCTCAAGTGATCCTCCCACC
       [C,T]
       TGGCTTCCTAAAGTGCTAGGATTACAGGTGTGAGCCACCATGCCCAGCCCAGTTATTTCT
       TTTGAGAAGTGGGGAGAATGATACCTATCCCTCAGAGTCGTGGTGGGGCTAGGTGGAGGT
       TATGGAAGTGTAAGTTTTTTTTTTTTTTGAGACGGAGTCTTGCTTTGTTGCCCAGGCTGG
       AGTGTAATGGTGCAATCTCGGCTCACTGCAACCTCTGCCTCCCAGGTTCAAGCGATTCTC
       CTGCCTCAGCCTCCCGAGTAGCTGGGATTACAGGCCCACCATCCCCGGCTAATTTGTGTA

17246  AGGGAAAACTTTTCAGTGAAATGACTGTGTAGTGTTTGCATTTGCAGCCTGCTACAGCTC
       TGGATTGGGAGCAAACAGAACAGAGTGCAGGCTGGTGCCACTATAAACTAGCTGTGTCTC
       CCACTTAAGCTTCTGGTCTACCATGAGCTTGAGCCCCTGCTTTGCTGAGGATAATTTTCA
       GAGCAGAATGAAATGAATGGCTACCACAGAAATTCAAATCACTCTTCTAGTTCTGGGCCA
       TGTGTCACTTAACATGAAAAAGAAGAATAAGTCTTAGCAAAATAATAGTGAGTAAAAAAG
       [T,C]
       AGTAAGGGAAATAATTGTTCACTTAATGTTAAGTGAAAAAAAAATCAGACCCCAGGGATGG
       ATAAAATCATGATTCCCCCCTTTTTTTATGTCATAGAAAATACGGCCGGGTGCGGTGGCT
       CACGCCTGTAATCCCAGCACTTTGGGAGGCCGAGGTGGGTGGATCACCAGTTCAGGAGAT
       CGAGACCATCCTGGCTAACATGGTGAAACCCCGTCTCTACTAAAATTACAAAAAATTAGC
       CAGGCGTGGTGGTGCATGCCTGTAGTCCCAGCTACTCGGGAGGCTGAGGCAGGAGAATGG

18359  GATAGAGCGAGACTCTGTCTCAAAAAAAAAAAAAAAAAAAAAAAGATGGTGATTTCTGCAAG
       TGGGAAGGGTGAGTGGGGCATGTGGTTAGATGTAGGATATTGACAAGAGCTTTGTTTTTT
       AGTTTGGGTGGTGGGTTCTCTTAGATCCTTGTTATATCATTTAAAAAATCTAATTTAGGC
       CAGGTGTGGTGGCTCACGCCTGTAATTCCAGCACTTTGGGAGGCCGAGGCAGGCAGATCA
       CCTGAGCTCAGGAGTTTGTGACTAGCCTGGGCAACATGGTGAAACCTCATCTCAACTGAA
       [A,G]
       TATAAAAAATTAGCCAGGGGTGGTGGCGCGTGCCTGTAGTCCCAGCTGTTCGGGAGGTTG
       AAGCACAAGAATTTTTGAGCCCAGGAAGTGGAGGTTGCAGTGAGCCAAGATTGTGCCACT
       GCACTCCAATTTGGGCTACAGAGTGAGACTCCGTCTAAAAAAAAAAAAAATTATTTGTTC
       AGCCTACTGAATTGTTGGTTTTGTATTTGAATGATTAAATGTTTAAAGTTTCCTCTGGGC
       TATGAGGTTGAGCTTGGAGAGCTGTGCTTTCATATCTGTGGGTATAAAACGTCCAGGGGT

18494  TTCTCTTAGATCCTTGTTATATCATTTAAAAAATCTAATTTAGGCCAGGTGTGGTGGCTC
       ACGCCTGTAATTCCAGCACTTTGGGAGGCCGAGGCAGGCAGATCACCTGAGCTCAGGAGT
       TTGTGACTAGCCTGGGCAACATGGTGAAACCTCATCTCAACTGAAATATAAAAAATTAGC
       CAGGGGTGGTGGCGCGTGCCTGTAGTCCCAGCTGTTCGGGAGGTTGAAGCACAAGAATTT
       TTGAGCCCAGGAAGTGGAGGTTGCAGTGAGCCAAGATTGTGCCACTGCACTCCAATTTGG
       [A,G]
       CTACAGAGTGAGACTCCGTCTAAAAAAAAAAAAAATTATTTGTTCAGCCTACTGAATTGT
       TGGTTTTGTATTTGAATGATTAAATGTTTAAAGTTTCCTCTGGGCTATGAGGTTGAGCTT
       GGAGAGCTGTGCTTTCATATCTGTGGGTATAAAACGTCCAGGGGTGGCCACAGGAGGAGG
       AATGGATTAGCCCATGGTGGGAATGTCATTAAGTCAAAGATAGGAGGTAAGCAGCTTAGG
       AGGCACCCTGGCTTCCCCCTTGATCACACACGTCTCCTCGGAAAACTTGTCCTCCATCCG

18998  TGTCATTAAGTCAAAGATAGGAGGTAAGCAGCTTAGGAGGCACCCTGGCTTCCCCCTTGA
       TCACACACGTCTCCTCGGAAAACTTGTCCTCCATCCGTGGACCAGATAGTGCTAAAGTCA
       AAATGAGTGACTTCTCTAATGCTCACATCAGGACACCTGTGCCAGAGCTGGCTCCTGTTA
       ACCCAAAAGAGCCATGCAAGGGTTGCCATGGTGAGATTGTTGCTGCCTGAGTGCCATTGT
       TTATTCTTGACACTCAGTTATTTGGGCTTTGATTCCAACATTGTCCTAGGCACAGGGTAA
       [T,C]
       AGAGCCAGAGCTGGGACGCCTCCCTCACTCTGGGGCTCCATAGGCTGGGCCAAGCTAAAT
       GACTGAAAGTCACATAGGGGTCTGTGGAAGACCAGCCCTCTGGGGCTTGTTCCTTTCCCC
       AAATGCTACTCCTCTGCCCCATCAGTTGTCTGTTTCCCCAGTAGGTTGTGGATGTCAGTC
       TAAAATGCTGCCCACCCGGCAGAGGATGGTATGGGAGGCTGTGGGGCCATGTGGGGTGCT
       GTTCCCTGGCCTGTTTGGGAAAAGAGAAGGCAGAAAGCATCTAACCTTTATTGAGCACCT
```

FIGURE 3 P

| | |
|---|---|
| 20312 | TATGCCTCAAAATTCAGATGCATGAAAGATTATTAAATTCACCCACATTAAAAAATTTGT<br>TTTTTGAGCCAGGGTCTTGCTCTGTCACTCAGGCTGGAGTGCAGTAGTGCAAACAGTGCT<br>CACTGCAGCCTCAATCTCCTGGGTTCAAGTGATCCTTCCACCTCAGCCTCCCAAGTAAGA<br>GTAGCAGGGACATCAGGTGCATGCCACCATGCATTAAAATGAGGATTAAAAATGCTCAGG<br>TGAATTTTTAAAATATTTTGTAGCAACAGGGGCTTCCCATCTTACCCAGGCTGGTCTTGA<br>[A,G]<br>CTCCTGGGCTCAAGCAGTCCTTCCTCCTTGACCTCCCAAAGTGTTGGGATTGCAGGTGTG<br>AACCACTGCACCTGACCTAAATTTTTTTTTTTTTTTTTGCATGCAAAAACACCACAAGCAG<br>AGTCAAAAGACAAGTGACAAACTGGGGGAAATCATTTACAAGAAATATCACAAAGGGCTA<br>ATTTTCCCAATAGAGAGAAAACATTTTTTAAAATAGGGAAAAGAATAAAAACCAAGACCT<br>GACAGAAAAATTGGGAAAGACATGAGTAGACAGTTCACAGAAAAAGATATACAGATGGTC |
| 20745 | AGTGACAAACTGGGGGAAATCATTTACAAGAAATATCACAAAGGGCTAATTTTCCCAATA<br>GAGAGAAAACATTTTTTAAAATAGGGAAAAGAATAAAAACCAAGACCTGACAGAAAAATT<br>GGGAAAGACATGAGTAGACAGTTCACAGAAAAAGATATACAGATGGTCCTTAATCATATG<br>GAGAGATGTTTGACTTTACTCATAATAAGCAAAATGCAAAGTAAGCCCCAATGAGAGATC<br>ATTTCTCCTCCATGTGATTGGCAGACATGCAAATGTTTGATCAACACTCTGGTGGTGAGC<br>[T,C]<br>TCAAGAAAATCCCTCATACAGTGCTAGCAGGAGAGCAAACTGGCCAAAGTCCCATGGAGG<br>GGAATTTGTCAATATCTAAGAAAATTACGTATGTATTTGCTGCTTGACCCAGCAAGACTT<br>CTAGGAATTTACATGGAAGATCTTCTCCACAGATATAGAATACTTATGCCGGAGTCATTTA<br>CTGCAACATTATTTGCAATAGCAAAGTATTAGAAACAACCTAAATACCCATGGAGACTGG<br>TTGAATAAATTACAGGAATCCAGTCATGCAATGGAGTCAAATGCAGTAATTAAAATAATA |
| 21422 | CACTCCATCCTGGGTGACAGAGCAAGACTCTGTCTCAAACAAACTAACAATAATAATTAA<br>TAAAGGAAGATCTCCATGCAGTTTCATGGAGTGATTTCTATGACATATTTTTAAATAAAA<br>AGCCAGAAAACCAAACCAGTTAAATAAAAGCCCTAGGGTATCAAAGGGTATATACAGTGT<br>TACTGTGTTTTATGTAAGAAAGGGCAATATATTTATTTAATTTTTTTTTTTGGAAACAGA<br>GTCTTGCTCTGTTGCCCAGGCTGGAGGGCAGTGGCGCGATCTCAGCTCCTTGCAACCTCT<br>[G,C]<br>CCTCCCGGGTCCAAGTGATTCTCATGACTCAGCCTCCTGAGTAGCTGGGATTACAGGCAT<br>GTGCCACATGCCCGGCTAATTTTGTATTTTTGGTAGAGATGGTGTTTCACCATGTTGGTC<br>AGGCTCGTCTCAAACTCCTGACCTCAGGTGATCCTCCTGCCTTGGCTTCCCAAAGTGCGG<br>GATTACAGGCATGAGCCACTGTGCCTGGCCTTTAGTGGTGATTTCTGAGATTTTGATGCA<br>CCCATCACCCAAGCAGTATACACTGTACCCAGTGTGTAGTCTTTTATCCCTTACGCCCCT |
| 21624 | GGCAATATATTTATTTAATTTTTTTTTTTGGAAACAGAGTCTTGCTCTGTTGCCCAGGCT<br>GGAGGGCAGTGGCGCGATCTCAGCTCCTTGCAACCTCTGCCTCCCGGGTCCAAGTGATTC<br>TCATGACTCAGCCTCCTGAGTAGCTGGGATTACAGGCATGTGCCACATGCCCGGCTAATT<br>TTGTATTTTTGGTAGAGATGGTGTTTCACCATGTTGGTCAGGCTCGTCTCAAACTCCTGA<br>CCTCAGGTGATCCTCCTGCCTTGGCTTCCCAAAGTGCGGGATTACAGGCATGAGCCACTG<br>[T,C]<br>GCCTGGCCTTTAGTGGTGATTTCTGAGATTTTGATGCACCCATCACCCAAGCAGTATACA<br>CTGTACCCAGTGTGTAGTCTTTTATCCCTTACGCCCCTACTACCCTTCCCGGCTGATTTT<br>TACTAATAGATTTGTGATAGGTAGTAGCAGTTGTATAGCAATTTTGAAACTGCTTTGAAT<br>ATTGAAGGACAGAACAAATAAGTAAATATACTGATGTTATTGGGAAATAAGTTCTCACTG<br>AAGGAGAAGGGAGACACAAATATGGAATGGGGAAGATGAGAAAAATCCTTTAATTTTAT |
| 22826 | TTGGCCAGGCTGTTTTGCAAACTCCTGACCTCAGGTAATCCACCTGCCTTGGCCTCCCAA<br>AGTGCAGGGATTACAGGCGTGAGCCACTGTGCCTGGCTGAAAAGCTCATTCTTATAGCAG<br>AATGCCAATAAATGTAGAAGGAATGATGGGAATTAGGTAATCACTATTTTGCAACCTCCA<br>GTATAATAACTCATTTAGGCAAGGGTCATAAATTGACACTAAATCCATTGGTGAAGGATT<br>TTGGGGTAACAGAATAGTCACATAGTCTCAAAGTATGGGAAAGACACAAAGACACAAGAT<br>[T,G,C]<br>ACCTACGTAGAACTCTTGTCAAAAGGATTAACGTAAGTCTAATCATGAGGAAACAATCAA<br>CTAAATCTAGTGGTAGAGCATCCTAAAAAACTACTGGCCTGGAGTCTAAAAATGTCTAGGC<br>TGGGTGCAGTGGCTCATGCCTGTAATCTCAGGCTTTGGGAGCCTGAAGCAGGAGGATCAC<br>TTGAAGCCAAGAGTTTGAGACTAGCCTAGGCAACGTAGTGAGACCCTGTCCCTACAAAAC<br>AAAAACAGAAACAAAAAAAACAAAACAACAAATGTTCTGAAAGTCTAAAAGTTATTGGGA |
| 23041 | ACACTAAATCCATTGGTGAAGGATTTTTGGGGTAACAGAATAGTCACATAGTCTCAAAGTA<br>TGGGAAAGACACAAAGACACAAGATCACCTACGTAGAACTCTTGTCAAAAGGATTAACGT<br>AAGTCTAATCATGAGGAAACAATCAACTAAATCTAGTGGTAGAGCATCCTAAAAACTACT<br>GGCCTGGAGTCTAAAAATGTCTAGGCTGGGTGCAGTGGCTCATGCCTGTAATCTCAGGCT<br>TTGGGAGCCTGAAGCAGGAGGATCACTTGAAGCCAAGAGTTTGAGACTAGCCTAGGCAAC<br>[G,A]<br>TAGTGAGACCCTGTCCCTACAAAACAAAAACAGAAACAAAAAAAACAAAACAACAAATGT<br>TCTGAAAGTCTAAAAGTTATTGGGATCTGTTCTAGATTAGAGGAGAATAAAAAGATATGT<br>CAACCAACTACAACATATGATCATCAATTAGATCCTGAATCAGAAAAAATAAAATTATAA<br>AGGATACTTTTGGGACAAGAGTGAACATTTGAATGTGGACTGTCTTACATAATGTATTAA<br>TGAATCGATGTTAAATTTCTTGCAGGTGATAATGGTATTGTGGTTTATGCAGCAGAATGT |
| 23379 | AAAAAAAACAAAACAACAAATGTTCTGAAAGTCTAAAAGTTATTGGGATCTGTTCTAGAT<br>TAGAGGAGAATAAAAAGATATGTCAACCAACTACAACATATGATCATCAATTAGATCCTG<br>AATCAGAAAAAATAAAATTATAAAGGATACTTTTGGGACAAGAGTGAACATTTGAATGTG<br>GACTGTCTTACATAATGTATTAATGAATCGATGTTAAATTTCTTGCAGGTGATAATGGTA<br>TTGTGGTTTATGCAGCAGAATGTCTTTGTTCCTATGAAATACATGCTGAAATACTTTGGG<br>[G,A]<br>TAAAGTGGCTTGTGTTGTCTGCAATGATCTTTCAAAGATTCAGAGGGGAAAAATGGTCTT |

FIGURE 3 Q

```
        CATATATATATTATTGAAATGGAATTCTTTTCTTCCTGACCCATCTAACCTAACACTCCCCA
        CTGGGCTGGTCACTGGCGAAGGATTCCTTTTCTGTTTTCAGCGCTCCTTGGTATGGAGCC
        CGGAGCCAGCAGAGCAACAAATAGGTGCAGGGCCTGCTCCTGGCACCGTGTTCTGATTTC
        CTGTCCCCTCATTCGCTGGGAACACTGAGTTGAGGGCCTGGAGACGCAAGTTCAAGTCCC

23439   TAGAGGAGAATAAAAAGATATGTCAACCAACTACAACATATGATCATCAATTAGATCCTG
        AATCAGAAAAAATAAAATTTATAAAGGATACTTTTGGGACAAGAGTGAACATTTGAATGTG
        GACTGTCTTACATAATGTATTAATGAATCGATGTTAAATTTCTTGCAGGTGATAATGGTA
        TTGTGGTTTATGCAGCAGAATGTCTTTGTTCCTATGAAATACATGCTGAAATACTTTGGG
        GTAAAGTGGCTTGTGTTGTCTGCAATGATCTTTCAAAGATTCAGAGGGGAAAAATGGTCT
        [T,C]
        CATATATATTATTGAAATGGAATTCTTTTCTTCCTGACCCATCTAACCTAACACTCCCCA
        CTGGGCTGGTCACTGGCGAAGGATTCCTTTTCTGTTTTCAGCGCTCCTTGGTATGGAGCC
        CGGAGCCAGCAGAGCAACAAATAGGTGCAGGGCCTGCTCCTGGCACCGTGTTCTGATTTC
        CTGTCCCCTCATTCGCTGGGAACACTGAGTTGAGGGCCTGGAGACGCAAGTTCAAGTCCC
        ATTGACCCTGGGAAAGTTATTCTACCTCCCTAATTTCCTCATCCTGGGCTTCAGGGTCTT

23779   CATCTAACCTAACACTCCCCACTGGGCTGGTCACTGGCGAAGGATTCCTTTTCTGTTTTC
        AGCGCTCCTTGGTATGGAGCCCGGAGCCAGCAGAGCAACAAATAGGTGCAGGGCCTGCTC
        CTGGCACCGTGTTCTGATTTCCTGTCCCCTCATTCGCTGGGAACACTGAGTTGAGGGCCT
        GGAGACGCAAGTTCAAGTCCCATTGACCCTGGGAAAGTTATTCTACCTCCCTAATTTCCT
        CATCCTGGGCTTCAGGGTCTTCAAGGCCCCACCCAACCATGATGTCTGGTGGAAGAAGCC
        [A,G]
        TCTTTGAACGCCAATGCATATAGGGTCCTGGGAGCTGGGGACAATTTGGTAACTTCTAAT
        GACCCTCTGTGGCAAGGGGATGGAAAGGAAGGTTTGTCCTTTGGTTTCTTCCTTCCCTAA
        ACTAGGTCCTAGTAATTTTGGGGAAGAAAGGAGACAGCAAGGAATGCATGTGCACGTGTG
        GGTATGATTGTCAGTGAGTGAGGAGCTGAAGCTGGGGGCTGGGGGGTGGGATGGGGAAAA
        TGCCTGGGGGCTGAGGGAGGACCCTGCTTGGTGTCCCAGGGCTCCTGGGGAAGCTCCTAG

24196   CTAAACTAGGTCCTAGTAATTTTGGGGAAGAAAGGAGACAGCAAGGAATGCATGTGCACG
        TGTGGGTATGATTGTCAGTGAGTGAGGAGCTGAAGCTGGGGGCTGGGGGGTGGGATGGGG
        AAAATGCCTGGGGGCTGAGGGAGGACCCTGCTTGGTGTCCCAGGGCTCCTGGGGAAGCTC
        CTAGCCCCACCTGTTCTGCTTCCACCCCCAGGCCCATGAGAGGCTGGAGGAGACGAAGCT
        GGAGGCCGTGAGAGACAACAACCTGGAGCTGGTGCAGGAGATCCTGCGGGACCTGGCGCA
        [C,G]
        CTGGCTGAGCAGAGCAGCACAGCCGCCGAGCTGGCCCACATCCTCCAGGAGCCCCACTTC
        CAGGTTCCTGGCTGCTAGGGCTGGGGTGAGGGAGCAGGAGGTGGGTGGACTGGGGCATGC
        TGCTGTTGGATGGGCCAGCAGGAAGTTGGATCTGGGATGGGAAGAGACCCGGGACACTGC
        CCCATTGTCCCTTCTCTTCCCACCACCCCCAGTCCCTCCTGGAGACGCACGACTCTGTG
        GCCTCAAAGACCTATGAGACACCACCCCCCAGCCCTGGCCTGGACCCTACATTCAGCAAC

24197   TAAACTAGGTCCTAGTAATTTTGGGGAAGAAAGGAGACAGCAAGGAATGCATGTGCACGT
        GTGGGTATGATTGTCAGTGAGTGAGGAGCTGAAGCTGGGGGCTGGGGGGTGGGATGGGGA
        AAATGCCTGGGGGCTGAGGGAGGACCCTGCTTGGTGTCCCAGGGCTCCTGGGGAAGCTCC
        TAGCCCCACCTGTTCTGCTTCCACCCCCAGGCCCATGAGAGGCTGGAGGAGACGAAGCTG
        GAGGCCGTGAGAGACAACAACCTGGAGCTGGTGCAGGAGATCCTGCGGGACCTGGCGCAG
        [C,G]
        TGGCTGAGCAGAGCAGCACAGCCGCCGAGCTGGCCCACATCCTCCAGGAGCCCCACTTCC
        AGGTTCCTGGCTGCTAGGGCTGGGGTGAGGGAGCAGGAGGTGGGTGGACTGGGGCATGCT
        GCTGTTGGATGGGCCAGCAGGAAGTTGGATCTGGGATGGGAAGAGACCCGGGACACTGCC
        CCATTGTCCCTTCTCTTCCCACCACCCCCAGTCCCTCCTGGAGACGCACGACTCTGTGG
        CCTCAAAGACCTATGAGACACCACCCCCCAGCCCTGGCCTGGACCCTACATTCAGCAACC

24487   CCTGGCGCAGCTGGCTGAGCAGAGCAGCACAGCCGCCGAGCTGGCCCACATCCTCCAGGA
        GCCCCACTTCCAGGTTCCTGGCTGCTAGGGCTGGGGTGAGGGAGCAGGAGGTGGGTGGAC
        TGGGGCATGCTGCTGTTGGATGGGCCAGCAGGAAGTTGGATCTGGGATGGGAAGAGACCC
        GGGACACTGCCCCATTGTCCCTTCTCTTCCCACCACCCCCAGTCCCTCCTGGAGACGCA
        CGACTCTGTGGCCTCAAAGACCTATGAGACACCACCCCCCAGCCCTGGCCTGGACCCTAC
        [A,G]
        TTCAGCAACCAGCCTGTACCTCCCGATGCTGTGCGCATGGTGGGCATCCGCAAGACAGCC
        GGAGAACATCTGGTGAGGACTGGGCAGGGCCAGAGGTGGTGCTGGTGAGGGTGGGGGGAT
        TGAGAATAACCAATGAACGGACAAAAAAGGCCAAGTGTGGTCTGAAGATGAAGATGGGGC
        CAGCTTTGTGCAGGGAAGGATCGATGCAGCAAAGGGTCGGGGGAAGACCCAGGAGACCAT
        AGACACTGCACACACACCTGTGTCCGCACCTCTCCAGTCTGCCCACCTCTCCCCTCATTA

24689   TCTCTTCCCACCACCCCCAGTCCCTCCTGGAGACGCACGACTCTGTGGCCTCAAAGACC
        TATGAGACACCACCCCCCAGCCCTGGCCTGGACCCTACATTCAGCAACCAGCCTGTACCT
        CCCGATGCTGTGCGCATGGTGGGCATCCGCAAGACAGCCGGAGAACATCTGGTGAGGACT
        GGGCAGGGCCAGAGGTGGTGCTGGTGAGGGTGGGGGGATTGAGAATAACCAATGAACGGA
        CAAAAAAGGCCAAGTGTGGTCTGAAGATGAAGATGGGGCCAGCTTTGTGCAGGGAAGGAT
        [C,T]
        GATGCAGCAAAGGGTCGGGGGAAGACCCAGGAGACCATAGACACTGCACACACACCTGTG
        TCCGCACCTCTCCAGTCTGCCCACCTCTCCCCTCATTAGTACCTGCTGTAAGTGAAGAAT
        TTAGGCAGAAGGATGGAGGAGGACTTTGTGAGGGTGGGGGTGGGTGGGTAGGGACAGGAA
        TGGAGGAGCTATTAGGAGACTATTTTGAAGATTCTGACTTGGAGCAATTGGGGCCTCATCT
        TACACTCCCTCTGACCTCCAGGGTGTAACGTTCCGCGTGGAGGGCGGCGAGCTGGTGATC

25022   GACCATAGACACTGCACACACACCTGTGTCCGCACCTCTCCAGTCTGCCCACCTCTCCCC
        TCATTAGTACCTGCTGTAAGTGAAGAATTTAGGCAGAAGGATGGAGGAGGACTTTGTGAG
```

FIGURE 3 R

```
         GGTGGGGGTGGGTGGGTAGGGACAGGAATGGAGGAGCTATTAGGAGACTATTTGAAGATT
         CTGACTTGGAGCAATTGGGGCCTCATCTTACACTCCCTCTGACCTCCAGGGTGTAACGTT
         CCGCGTGGAGGGCGGCGAGCTGGTGATCGCGCGCATTCTGCATGGGGGCATGGTGGCTCA
         [A,G]
         CAAGGCCTGCTGCATGTGGGTGACATCATCAAGGAGGTGAACGGGCAGCCAGTGGGCAGT
         GACCCCCGCGCACTGCAGGAGCTCCTGCGCAATGCCAGTGGCAGTGTCATCCTCAAGATC
         CTGCCCAGCTACCAGGAGCCCATCTGCCCCGCCAGGTGGCCCCTCACCCAGCACAAGG
         CCCAAGGGATGGCTGAGCCTCCTGGCTGTCAAGGTTGCAGGTCTCACGGAGGCCCTCCTC
         TCCTACTGGTTTCCTCCAGGGAAGATGGGGGGTGGGACCTGCAGCCCAGGGGCAGCTGAC
26015    CACCAGGGAGGAGCATGGGCAGGCCTGGAGGCATCACTCCTGCAGGGGGACAGTTCCATT
         GCCCCTTAGTCTCTGTGAAAAGAGGGGGCATGGGGTAGACCTCCACCTGCAGCCTTCTGC
         TGACCCTTCCCCCGACCCTTTGCTGATTCCTGGGCCCAGGTATTTGTGAAATGTCACTTT
         GACTATGACCCGGCCCGAGACAGCCTCATCCCCTGCAAGGAAGCAGGCCTGCGCTTCAAC
         GCCGGGGACTTTGCTCCAGATCGTAAACCAGGATGATGCCAACTGGTGGCAGGTGAGCTGC
         [G,A]
         GGCACCCCCGCATCTCTCCAGGTATGGTGCATGGGAGGGCGAGGGCACAGGGAGGGGTCC
         TCTTGCTCAGGCAGATCTTGGTCTCATGTCCGTTTTAGGCATGCCATGTCGAAGGGGCA
         GTGCTGGGCTCATTCCCAGCCAGCTGCTGGAGGAGAAGCGGAAAGCATTTGTCAAGAGGG
         ACCTGGAGCTGACACCAAACTCAGGTAGGAGGTCCCCCCTACCCCACACCTCCAATCTGG
         GATCCAACAGGGCCCTGTCTGCCTCACTCACCCATCTCCCTATGGCCAGGGACCCTATGC
28829    CTTGGGTTGCTTACAGCTGGGGGAAAGCTGAAGGGTAGGAGAAAGCCAGAGGCGGGAAGG
         CTGGCTGGAGGGCTGAGTCAGCGTCAGGGAGCAGGCAGCGCCTGGAGGAGAGGCTTCAAG
         GCCTCATTGCAGAACTCCAGCCCCATCCTCCTTCCTATGTCTTGCTGCGCCTTCCCAGGA
         GGTGGAGGGTTTGCGGCGCTCTGAGCGCAGGGGTCCCTCTGCTGGCCATGCCTGGTGCTG
         CAGCATTCCGGCCCCAGGTCAGAGCGTGCCTGGGGCCCAGGAGAGGCTGTCTAGGCTGGC
         [A,C]
         CCCTTCTGCCAATGACCCCCTTAAGGAGCTCTGGACCTTTGCCTGATCCCCATTCTGGGC
         ACCTCCTCCTTGGCAACAGGTGTGGCCAACTGGAGCTGTTGGGATGCAGCTAGCTTCAGC
         TTATTTAAGTCAGTTGTCAAGTACCCTTCCTCACCCCTGCCCATCCAGCTTCCACTGGGT
         CGAGGGTGGGGTTGCCCTGGGTACTTGTGGATTGCCCTGGTACCAGCCTGTCTAGCTGCA
         TAGGTAAGGCAGCCTAGTCAGACTTGAGGGAGCACTGGCTTGAGAGTCAGGCAGACCCTG
29260    CAGTTGTCAAGTACCCTTCCTCACCCCTGCCCATCCAGCTTCCACTGGGTCGAGGGTGGG
         GTTGCCCTGGGTACTTGTGGATTGCCCTGGTACCAGCCTGTCTAGCTGCATAGGTAAGGC
         AGCCTAGTCAGACTTGAGGGAGCACTGGCTTGAGAGTCAGGCAGACCCTGTTTAGCCACT
         GACTGGCTATGTGACCTTTTTATACCTTCATTTTCTCTGCTATAAATGGGAAAGAATTAA
         TCCTATCTTGCAGAGCTGTAGTGAAGATTATGTGGCATGCAAAGCATTTAGGGGTGTGAT
         [C,T]
         GGCAGTTATTAAAGCTTATTTCCTCCCTTTCACTCACCATCTGTGGTTGATGGTGAGCCA
         CTTTGAGGCACGCAGAGAGGGGCCCCTGCCTCCCTAGCCAGGGAGTCCACACCAGGGTTG
         GGCTTTGGGGAGGGGGAGTGGGGGCAGCTGTAGCTCCTTCTGACAGTGGGGTGAGTTGT
         GGGCACTGACTGTAGGGAGGTCCCCTTGTGCCTGGGCAGGAGGCGGACCTGAGACGGACA
         GTGGAGGAGAGCAGCCGCATCCAGCGGGGCTACGGGCACTACTTTGACCTCTGCCTGGTC
29673    CAGGGTTGGGCTTTGGGGAGGGGGAGTGGGGGCAGCTGTAGCTCCTTCTGACAGTGGGGG
         TGAGTTGTGGGCACTGACTGTAGGGAGGTCCCCTTGTGCCTGGGCAGGAGGCGGACCTGA
         GACGGACAGTGGAGGAGAGCAGCCGCATCCAGCGGGGCTACGGGCACTACTTTGACCTCT
         GCCTGGTCAATAGCAACCTGGAGAGGACCTTCCGCGAGCTCCAGACAGCCATGGAGAAGC
         TACGGACAGAGCCCCAGTGGGTGCCTGTCAGCTGGGTGTACTGAGCCTGTTCACCTGGTC
         [T,C]
         TTGGCTCACTCTGTGTTGAAACCCAGAACCTGAATCCATCCCCCTCCTGACCTGTGACCC
         CCTGCCACAATCCTTAGCCCCCATATCTGGCTGTCCTTGGGTAACAGCTCCCAGCAGGCC
         CTAAGTCTGGCTTCAGCACAGAGGCGTGCACTGCCAGGGAGGTGGGCATTCATGGGGTAC
         CTTGTGCCCAGGTGCTGCCCACTCCTGATGCCCATTGGTCACCAGATATCTCTGAGGGCC
         AAGCTATGCCCAGGAATGTGTCAGAGTCACCTCCATAATGGTCAGTACAGAGAAGAGAAA
30229    ATGTGTCAGAGTCACCTCCATAATGGTCAGTACAGAGAAGAGAAAAGCTGCTTTGGGACC
         ACATGGTCAGTAGGCACACTGCCCCCTGCCACCCCTCCCCAGTCACCAGTTCTCCTCTGG
         ACTGGCCACACCCACCCCATTCCTGGACTCCTCCCACCTCTCACCCCTGTGTCGGAGGAA
         CAGGCCTTGGGCTGTTTCCGTGTGACCAGGGGAATGTGTGGCCCGCTGGCAGCCAGGCAG
         GCCCGGGTGGTGGTGCCAGCCTGGTGCCATCTTGAAGGCTGGAGGAGTCAGAGTGAGAGC
         [T,C]
         AGTGGCCACAGCTGCAGAGCACTGCAGCTCCCAGCTCCTTTGGAAAGGGACAGGGTCGCA
         GGGCAGATGCTGCTCGGTCCTTCCCTCATCCACAGCTTCTCACTGCCGAAGTTTCTCCAG
         ATTTCTCCAATGTGTCCTGACAGGTCAGCCCTGCTCCCCACAGGGCCAGGCTGGCAGGGG
         CCAGTGGGCTCAGCCCAGGTAGGGGCAGGATGGAGGGCTGAGCCCTGTGACAACCTGCTG
         CTACCAACTGAAGAGCCCCAAGCTCTCCATGGCCCACAGCAGGCACAGGTCTGAGCTCTA
30470    CCCGGGTGGTGGTGCCAGCCTGGTGCCATCTTGAAGGCTGGAGGAGTCAGAGTGAGAGCC
         AGTGGCCACAGCTGCAGAGCACTGCAGCTCCCAGCTCCTTTGGAAAGGGACAGGGTCGCA
         GGGCAGATGCTGCTCGGTCCTTCCCTCATCCACAGCTTCTCACTGCCGAAGTTTCTCCAG
         ATTTCTCCAATGTGTCCTGACAGGTCAGCCCTGCTCCCCACAGGGCCAGGCTGGCAGGGG
         CCAGTGGGCTCAGCCCAGGTAGGGGCAGGATGGAGGGCTGAGCCCTGTGACAACCTGCTG
         [C,T]
         TACCAACTGAAGAGCCCCAAGCTCTCCATGGCCCACAGCAGGCACAGGTCTGAGCTCTAT
         GTCCTTGACCTTGGTCCATTTGGTTTTCTGTCTAGCCAGGTCCAGGTAGCCCACTTGCAT
         CAGGGCTGCTGGGTTGGAGGGGCTAAGGAGGAGTGCAGAGGGGACCTTGGGAGCCTGGGC
```

FIGURE 3 S

```
              TTGAAGGACAGTTGCCCTCCAGGAGGTTCCTCACACACAACTCCAGAGGCGCCATTTACA
              CTGTAGTCTGTACAACCTGTGGTTCCACGTGCATGTTCGGCACCTGTCTGTGCCTCTGGC

30829      ATGTCCTTGACCTTGGTCCATTTGGTTTTCTGTCTAGCCAGGTCCAGGTAGCCCACTTGC
              ATCAGGGCTGCTGGGTTGGAGGGGCTAAGGAGGAGTGCAGAGGGGACCTTGGGAGCCTGG
              GCTTGAAGGACAGTTGCCCTCCAGGAGGTTCCTCACACACAACTCCAGAGGCGCCATTTA
              CACTGTAGTCTGTACAACCTGTGGTTCCACGTGCATGTTCGGCACCTGTCTGTGCCTCTG
              GCACCAGGTTGTGTGTGTGTGCGTGTGCACGTGCGTGTGTGTGTGTGTGTGTCAGGTTTA
              [A,G]
              TTTGGGGAGGAAGCAAAGGGTTTTGTTTTGGAGGTCACTCTTTGGGGCCCCTTTCTGGGG
              GTTCCCCATCAGCCCTCATTTCTTATAATACCCTGATCCCAGACTCCAAAGCCCTGGTCC
              TTTCCTGATGTCTCCTCCCTTGTCTTATTGTCCCCCTACCCTAAATGCCCCCCTGCCATA
              ACTTGGGGAGGGCAGTTTTGTAAAATAGGAGACTCCCTTTAAGAAAGAATGCTGTCCTAG
              ATGTACTTGGGCATCTCATCCTTCATTATTCTCTGCATTCCTTCCGGGGGGAGCCTGTCC

31615      TATACTAGGAATCTCATTTGCATTTGCATAGACTATACACATGGGGTGGAAAGGCCAGGC
              CTGCCCCCATCTCGTTGGTGTGGCTCTGCGTATACTACACACTCATTCTCCTGCTCCTCT
              TTTCCCTTAGTCAGTGTCCTTTCATCCTGATTCAGCTCTGCCTTGCATCACCCTCAGCCT
              AAGGGAGTGGGAAGGAAATGGGGTGTTTTCTTGCTGACCTGAGGCTATAGGGTCACTTGC
              CATTTCCTACCTTCTCTGGGGGATTTGAGGGTAGAGGCAGGGGAAGATCTGTTGTTGCAG
              [C,T]
              TGCTTCTGCCCCCTTGATCCAAATGACCATCATCTCTGATGGAGATGGGTTGGGTACCTG
              GCCTTCATGGCACCTTCACTGCTAGGGATGCTCAAGGGGCAGGCCTGGGGCCCTTCCCTC
              CTGTCTCTTCTCGGTCTTTCCTCTCTGAGCAGCCTCCTACCTCCCCTGCCTGAGCCCTCA
              CTCCACAGCCCTCCCAGGTACCTAGCAGAGGCTGTCAGTCCTTGGCTCACCTGGAACAGG
              GCTGGGGCTGGGTTGGAACAGGTGTGTGCCCCCACCACAGCTCTATGACTCTGTTCTCCC

32020      CTGGGGCCCTTCCCTCCTGTCTCTTCTCGGTCTTTCCTCTCTGAGCAGCCTCCTACCTCC
              CCTGCCTGAGCCCTCACTCCACAGCCCTCCCAGGTACCTAGCAGAGGCTGTCAGTCCTTG
              GCTCACCTGGAACAGGGCTGGGGCTGGGTTGGAACAGGTGTGTGCCCCCACCACAGCTCT
              ATGACTCTGTTCTCCCTCCCTGCCATTGTGGACTCTTGTATTTGAGGGACCTCAAGAGAG
              TGAGGACCCTACCATCCACTGTCCATATTCAGTCCCAGCCCCAGTGCGCTTCCTCTGTTC
              [C,T]
              CTCCCTCAGCCATCCAATTCTTGAGTTTTCTCACTGATTGGTTTTCTTTCTTTTTCCTTG
              GATTAAATGTGAAAGCAAAGGCTTCTGGCTCTGCTTTTCTTTGGTTGGGGTTGGATGGAT
              GGCTTTGGGAGAGAGTGAGAGCTGGGGAGCACAGCACAGATGACTACTAGAATGGAAGTC
              AGAGCAACATGTCTTGTTTTCTGCGATGTCTTCCTTTCCTCTGTCTTGCCCCTGCACACT
              CCCCCATCCCCAGAAGATGCTCCTTCTAAGTGCTTGTACCCAAGGACATGAACAGACATT

Chromosome map:   Chromosome 17
```

FIGURE 3 T

SEQUENCE LISTING

```
<160> NUMBER OF SEQ ID NOS: 8

<210> SEQ ID NO 1
<211> LENGTH: 3604
<212> TYPE: DNA
<213> ORGANISM: Homo sapiens

<400> SEQUENCE: 1
gtggtctgtg cggtgtctcc caaaccacta cctggctgcc cccgtaccag ctgctgggaa       60
agactacttc ctccgagttg tgccggcctc cgcgttctcc tcacctcccc tctcctccgg      120
acctccgccc cctcgcggag aggccttgcc gctttaagag ccgggctagc gattgacaag      180
caataaacgc tgagcgcccg gctgcgctgg agccgcccgg agctaggggc ttcccgcggc      240
gcaggagaga cgtttcagag cccttgcctc cttcaccatg ccggttgccg ccaccaactc      300
tgaaactgcc atgcagcaag tcctggacaa cttgggatcc ctccccagtg ccacgggggc      360
tgcagagctg gacctgatct tccttcgagg cattatggaa agtcccatag taagatccct      420
ggccaaggcc catgagaggc tggaggagac gaagctggag gccgtgagag acaacaacct      480
ggagctggtg caggagatcc tgcgggacct ggcgcagctg gctgagcaga gcagcacagc      540
cgccgagctg gcccacatcc tccaggagcc ccacttccag tccctcctgg agacgcacga      600
ctctgtggcc tcaaagacct atgagacacc accccccagc cctggcctgg accctacgtt      660
cagcaaccag cctgtacctc ccgatgctgt gcgcatggtg ggcatccgca agacagccgg      720
agaacatctg ggtgtaacgt tccgcgtgga gggcggcgag ctggtgatcg cgcgcattct      780
gcatgggggc atggtggctc agcaaggcct gctgcatgtg ggtgacatca tcaaggaggt      840
gaacgggcag ccagtgggca gtgaccccg cgcactgcag gagctcctgc gcaatgccag      900
tggcagtgtc atcctcaaga tcctgcccag ctaccaggag ccccatctgc cccgccaggt      960
atttgtgaaa tgtcactttg actatgaccc ggcccgagac agcctcatcc cctgcaagga     1020
agcaggcctg cgcttcaacg ccggggactt gctccagatc gtaaaccagg atgatgccaa     1080
ctggtggcag gcatgccatg tcgaaggggg cagtgctggg ctcattccca gccagctgct     1140
ggaggagaag cggaaagcat ttgtcaagag ggacctggag ctgacaccaa actcagggac     1200
cctatgcggc agcctttcag gaaagaaaaa gaagcgaatg atgtatttga ccaccaagaa     1260
tgcagagttt gaccgtcatg agctgctcat ttatgaggag gtggcccgca tgccccgtt     1320 ccgccggaaa accctggtac tgattggggc tcagggcgtg ggacggcgca gcctgaagaa     1380
caagctcatc atgtgggatc cagatcgcta tggcaccacg tgcccctaca cctcccggcg     1440
gccgaaagac tcagagcggg aaggtcaggg ttacagcttt gtgtcccgtg gggagatgga     1500
ggctgacgtc cgtgctgggc gctacctgga gcatggcgaa tacgagggca acctgtatgg     1560
cacacgtatt gactccatcc ggggcgtggt cgctgctggg aaggtgtgcg tgctggatgt     1620
```

-continued

| | |
|---|---|
| caaccccag gcggtgaagg tgctacgaac ggccgagttt gtcccttacg tggtgttcat | 1680 |
| cgaggcccca gacttcgaga ccctgcgggc catgaacagg gctgcgctgg agagtggaat | 1740 |
| atccaccaag cagctcacgg aggcggacct gagacggaca gtggaggaga gcagccgcat | 1800 |
| ccagcgggc tacgggcact actttgacct ctgcctggtc aatagcaacc tggagaggac | 1860 |
| cttccgcgag ctccagacag ccatggagaa gctacggaca gagccccagt gggtgcctgt | 1920 |
| cagctgggtg tactgagcct gttcacctgg tccttggctc actctgtgtt gaaacccaga | 1980 |
| acctgaatcc atccccctcc tgacctgtga ccccctgcca caatccttag cccccatatc | 2040 |
| tggctgtcct tgggtaacag ctcccagcag gccctaagtc tggcttcagc acagaggcgt | 2100 |
| gcactgccag ggaggtgggc attcatgggg taccttgtgc ccaggtgctg cccactcctg | 2160 |
| atgcccattg gtcaccagat atctctgagg gccaagctat gcccaggaat gtgtcagagt | 2220 |
| cacctccata atggtcagta cagagaagag aaaagctgct ttgggaccac atggtcagta | 2280 |
| ggcacactgc cccctgccac ccctccccag tcaccagttc tcctctggac tggccacacc | 2340 |
| caccccattc ctggactcct cccacctctc accctgtgt cggaggaaca ggccttgggc | 2400 |
| tgtttccgtg tgaccagggg aatgtgtggc ccgctggcag ccaggcaggc ccgggtggtg | 2460 |
| gtgccagcct ggtgccatct tgaaggctgg aggagtcaga gtgagagcca gtggccacag | 2520 |
| ctgcagagca ctgcagctcc cagctccttt ggaaagggac agggtcgcag ggcagatgct | 2580 |
| gctcggtcct tccctcatcc acagcttctc actgccgaag tttctccaga tttctccaat | 2640 |
| gtgtcctgac aggtcagccc tgctccccac agggccaggc tggcagggc cagtgggctc | 2700 |
| agcccaggta ggggcaggat ggagggctga gccctgtgac aacctgctgt taccaactga | 2760 |
| agagccccaa gctctccatg gcccacagca ggcacaggtc tgagctctat gtccttgacc | 2820 |
| ttggtccatt tggttttctg tctagccagg tccaggtagc ccacttgcat cagggctgct | 2880 |
| gggttggagg ggctaaggag gagtgcagag gggaccttgg gagcctgggc ttgaaggaca | 2940 |
| gttgccctcc aggaggttcc tcacacacaa ctccagaggc gccatttaca ctgtagtctg | 3000 |
| tacaacctgt ggttccacgt gcatgttcgg cacctgtctg tgcctctggc accaggttgt | 3060 |
| gtgtgtgtgc gtgtgcacgt gcgtgtgtgt gtgtgtgtgt caggtttagt ttggggagga | 3120 |
| agcaaagggt tttgttttgg aggtcactct ttggggcccc tttctggggg ttccccatca | 3180 |
| gccctcattt cttataatac cctgatccca gactccaaag ccctggtcct ttcctgatgt | 3240 |
| ctcctccctt gtcttattgt cccctaccc taaatgcccc cctgccataa cttggggagg | 3300 |
| gcagttttgt aaaataggag actccctta agaaagaatg ctgtcctaga tgtacttggg | 3360 |
| catctcatcc ttcattattc tctgcattcc ttccggggg agcctgtcct cagaggggac | 3420 |
| aacctgtgac accctgagtc caaacccttg tgcctcccag ttcttccaag tgtctaacta | 3480 |
| gtcttcgctg cagcgtcagc caaagctggc ccctgaacca ctgtgtgccc atttcctagg | 3540 |
| gaagggaag gagaataaac agaatattta ttacaaaaaa aaaaaaaaaa aaaaaaaaa | 3600 |
| aaaa | 3604 |

<210> SEQ ID NO 2
<211> LENGTH: 552
<212> TYPE: PRT
<213> ORGANISM: Homo sapiens

<400> SEQUENCE: 2

Met Pro Val Ala Ala Thr Asn Ser Glu Thr Ala Met Gln Gln Val Leu
1               5                   10                  15

-continued

```
Asp Asn Leu Gly Ser Leu Pro Ser Ala Thr Gly Ala Ala Glu Leu Asp
         20                  25                  30

Leu Ile Phe Leu Arg Gly Ile Met Glu Ser Pro Ile Val Arg Ser Leu
         35                  40                  45

Ala Lys Ala His Glu Arg Leu Glu Glu Thr Lys Leu Glu Ala Val Arg
 50                  55                  60

Asp Asn Asn Leu Glu Leu Val Gln Glu Ile Leu Arg Asp Leu Ala Gln
 65                  70                  75                  80

Leu Ala Glu Gln Ser Ser Thr Ala Ala Glu Leu Ala His Ile Leu Gln
                 85                  90                  95

Glu Pro His Phe Gln Ser Leu Leu Glu Thr His Asp Ser Val Ala Ser
             100                 105                 110

Lys Thr Tyr Glu Thr Pro Pro Ser Pro Gly Leu Asp Pro Thr Phe
             115                 120                 125

Ser Asn Gln Pro Val Pro Pro Asp Ala Val Arg Met Val Gly Ile Arg
 130                 135                 140

Lys Thr Ala Gly Glu His Leu Gly Val Thr Phe Arg Val Glu Gly Gly
145                 150                 155                 160

Glu Leu Val Ile Ala Arg Ile Leu His Gly Gly Met Val Ala Gln Gln
                 165                 170                 175

Gly Leu Leu His Val Gly Asp Ile Ile Lys Glu Val Asn Gly Gln Pro
             180                 185                 190

Val Gly Ser Asp Pro Arg Ala Leu Gln Glu Leu Leu Arg Asn Ala Ser
             195                 200                 205

Gly Ser Val Ile Leu Lys Ile Leu Pro Ser Tyr Gln Glu Pro His Leu
 210                 215                 220

Pro Arg Gln Val Phe Val Lys Cys His Phe Asp Tyr Asp Pro Ala Arg
225                 230                 235                 240

Asp Ser Leu Ile Pro Cys Lys Glu Ala Gly Leu Arg Phe Asn Ala Gly
                 245                 250                 255

Asp Leu Leu Gln Ile Val Asn Gln Asp Asp Ala Asn Trp Trp Gln Ala
             260                 265                 270

Cys His Val Glu Gly Gly Ser Ala Gly Leu Ile Pro Ser Gln Leu Leu
             275                 280                 285

Glu Glu Lys Arg Lys Ala Phe Val Lys Arg Asp Leu Glu Leu Thr Pro
 290                 295                 300

Asn Ser Gly Thr Leu Cys Gly Ser Leu Ser Gly Lys Lys Lys Lys Arg
305                 310                 315                 320

Met Met Tyr Leu Thr Thr Lys Asn Ala Glu Phe Asp Arg His Glu Leu
                 325                 330                 335

Leu Ile Tyr Glu Glu Val Ala Arg Met Pro Pro Phe Arg Arg Lys Thr
             340                 345                 350

Leu Val Leu Ile Gly Ala Gln Gly Val Gly Arg Arg Ser Leu Lys Asn
             355                 360                 365

Lys Leu Ile Met Trp Asp Pro Asp Arg Tyr Gly Thr Thr Val Pro Tyr
 370                 375                 380

Thr Ser Arg Arg Pro Lys Asp Ser Glu Arg Glu Gly Gln Gly Tyr Ser
385                 390                 395                 400

Phe Val Ser Arg Gly Glu Met Glu Ala Asp Val Arg Ala Gly Arg Tyr
                 405                 410                 415

Leu Glu His Gly Glu Tyr Glu Gly Asn Leu Tyr Gly Thr Arg Ile Asp
             420                 425                 430

Ser Ile Arg Gly Val Val Ala Ala Gly Lys Val Cys Val Leu Asp Val
```

```
                    435                 440                 445
Asn Pro Gln Ala Val Lys Val Leu Arg Thr Ala Glu Phe Val Pro Tyr
    450                 455                 460

Val Val Phe Ile Glu Ala Pro Asp Phe Glu Thr Leu Arg Ala Met Asn
465                 470                 475                 480

Arg Ala Ala Leu Glu Ser Gly Ile Ser Thr Lys Gln Leu Thr Glu Ala
                485                 490                 495

Asp Leu Arg Arg Thr Val Glu Glu Ser Ser Arg Ile Gln Arg Gly Tyr
                500                 505                 510

Gly His Tyr Phe Asp Leu Cys Leu Val Asn Ser Asn Leu Glu Arg Thr
                515                 520                 525

Phe Arg Glu Leu Gln Thr Ala Met Glu Lys Leu Arg Thr Glu Pro Gln
            530                 535                 540

Trp Val Pro Val Ser Trp Val Tyr
545                 550

<210> SEQ ID NO 3
<211> LENGTH: 32654
<212> TYPE: DNA
<213> ORGANISM: Homo sapiens

<400> SEQUENCE: 3
cccccgggcc agctcctatc ccaagacctc cgccttcttt tcgtcctgac acggcactta      60
ggaccctatt cactgggttt aaactccaca ggccccttc acccaggccc gttccctccc     120
tgtccacccg ccccgcccc tgggccctct ttctggggtg ctggttggga gaaccaagcc     180
ccgctgccca ttgacactgg tccccgcccc tgcgtaggg gctccaaagt ggcttcaggc     240
accaaggtgg tgagctgtga ggggcccgg tatctgcgcg gcctccccgg gggctgtgcg     300
ggttgggggg acttagaagc ccggcattac gtaagaaccg tgctgttagc gcttccgggg     360 gttgggagc gagacagagg ttgcgctggg tcccggtggc cccctggtcc ccctaggcag     420
ctaacaccac aatcttccct gggagggggt ccgcagaagg gcgcgcgctg cttctcccgc     480
ttcccaagct gtagcggggc gggtcgggag ccagggttag ggtctggaga cttgggaggg     540
gaccggtgcc agaagcgaag agctagggtt agaaagttag gtcaattaag ggggggcgg     600 tgcggataaa gacggggtgg gggttggccg gggcagtcat ttagtgacct catccctggt     660
ctccggcggg cgcgcacgta gagagccttc tttgatggct cacaacacgc ccccctcccc     720
caggtcctag cgcccagggt gttagggctg ggtccgttgg ggcagggtg atctgatggt     780 ccaagcatgc acgtccgcct ggccttcga ccccatcctc tggccctcag ttctgtccag     840
acctccccgc gacctctcgc tctccaaagc gcctttgtca gacctttctt ctccgcacct     900
ctttgtatgt gtatggatgg agggatgggt gggaggttgg aagaaacctc tccctttcac     960
tgctggtccg ctcgcctgcg gacactatgg ctgatgtgga tatctcggag gcagagctga    1020
gagggcatct gggcccaggc ttttggaagc cgaggtgcag gttcccagat gtctgggtgc    1080
aggaccttgg cacggagcca ggctagcttg cctggcactg ccgttctcct gtggacacag    1140
ccaggccccg ccctctcaga ggcttggacg ggcgtggggg agcaaagcca gccgatgctc    1200
tgggaaccga ctccccggga gaaaacccag gcaggctggg caagacttcc gagcgcaggg    1260
atttcataca ggatcctccc tgccttttcc cgccctccac gctctaggga aggaggactt    1320
ctggagtccc ttctctgacc ctgtgaggga gagcagcgcc agccaggaga aggctccagg    1380
tcatcaaggc ctgggagggg gagggaaggg atccctcctc cctgctctct aggagtagag    1440
```

```
attggcacca ggggcacggg ccagcacagt ggatcctggg catttcttcc agcctgggtg    1500
tagcctgaat aggggtgccc ttcctctccc tgaaagcacc tttattccat gtcctcagcg    1560
gcagagctgg gaggaaaggg aaccatcccc ctcacttttg taatttctgt cacctgagct    1620
caggtgacca gctcaggcct gagaagggaa tgggagcaga gagggtttta ttgaaatcag    1680
gtactagtcc tctgggaaga atcctctttt ggggggaggt ggagttgccg tggttccccc    1740
acccccagga ctcagcaggc attcagtcct aaagtgggca ctgccagatg cttcccccca    1800
ctccccaccc ctgctgtgag ccactgcctc ctgttgtcat ggcaactggg aattagggtt    1860
ttatccagca gcacatgccc aggaaggcaa agggaagaag ggtgggggt aaccccctgc    1920 cctctcctgg gagaacgagg gagccactcc tagcctgggg aggccctgga atggaaactg    1980
gggctgtaga ctccatgctt ggttctgccc agagcacttg gtctccttgt gccagctctg    2040
agctaagaaa gggagagagg agagagagcc agccagaggg gccgtggaga ggtagatatc    2100
actctgtcag ccccccagat aaatgtggaa catcggcgct ttggtaggcc taggttccag    2160
aagcaaataa aatcaatgtg gttctgactc tcagggaacc tgcagtctag gagtactcat    2220
gttttctact ttggctcaaa ttctggactc ttttattatt ttttaaatga ctttttttt    2280 tttaagacag gttcttgctc tgttgcccag gctggagtgc agtggcgcaa tcatggctta    2340
ccgtagcctc gacctcctgg gctcaagaga tcccccctgcc tcagcccccac aagtagctgg    2400 gatcataggc atgcaccacc acacctggat aattttaat tttttgtag gatgggggt    2460 ctcgccatgt tgcccaggtg gctctcaaac tcctgggctc aggtgattct cctgcctcag    2520
cctcctaaag tgctgggatt ataggcgtga gccaccttgc tcagccaaat tatagtctta    2580
ccctctaaaa attctacttg tttcctcttc aaaaaacaaa caaacaaaaa atacaacagg    2640
aagaaacact ttatttatat acttattttt gagtcataaa acctggatt tcattttagc    2700 tctccttatt agctttgtga acttgggcaa atcagttaac ctcccttatc ctccctggtc    2760
tcctcctcct cagagaaata ggcgagtaat acctgctctt cctgcttccc aggaccgttg    2820
gaatcattgt tgttctccaa cccccacttt ctgggcagca ccttctcccc tacctttctg    2880
gctcgtcctg aaggggaggc tcttcctatt cccttcccca ttgctttgcc cttgtatctg    2940
ctcatcctcc tctctcccct ctccaggaga gacgtttcag agcccttgcc tccttcacca    3000
tgccggttgc cgccaccaac tctgaaactg gtaagaaggg ggtgaggatg ttagcttatt    3060
tcagtggttc agagggtgcc aggcgaggac ttaggggtgg gcacttgcac agctccagat    3120
aagaaccaac tggctccact gctgtccacc ctaccactca gccattcctt ctggcagctg    3180
ctgtggccat ctcctctgtg tgggttcctg tgctggaacg gagaagagaa agaataagac    3240
ccatacctgc tccagtgtag ggctggagca caactcacct ccgtgagggg cagggatgc    3300 atgctccaga ggtgacccgt actattgctg gagggcagtg gcataggacc aggccttcag    3360
gaggtggccc cggagctggg ccttggagaa tggcttgggg gtggagggat tacagcagca    3420
cagcctgggg ctgagaagtc cataatcgct gcccactagg ccagcatgtg ccagaggtgg    3480 acaggggta ctgggaccaa ggaagctgtg agtgaaggaa caagaatacc aggttaggat    3540
acctggacgt ggctctgtag gaggcattag acaagggag tgggccactc agacaaacta    3600
gcaaagcctc agtggcaaac tgcttaacct cttggagctc gcatttcttc ttctgtaaag    3660
aggctgctgt gagacgcaaa ggctgtaatg ggagagcaca ttactttttag gaatagtcat    3720 aattattatg ctgctgttgc tgccgctgcc accaagttgt tgttgttgtt tttgagacaa    3780
gttctggctc tttagcctag gctggagtgc agtggcgcaa gcttggctca ctgcaacctc    3840
```

-continued

```
tgcctaccag cctcaagtca ttctcccacc tcagcctccc aagtagctgg gactacaggt    3900
gtgcaccacc atgcccagct aattttttgta tttttcgtaa agacaaaaat gttgcccatg   3960
ctggtctcaa actcctgagc tcaagtactc caccgcctc gacctcccaa actactggga    4020
ttacaggtgt gaaccactgt gcctggcctg agttgttatt ttggcattaa ccctgtgtcc   4080
ttgaaacagt cacctccttt tgaagacctg agatttccct aagatgagat gatgggacaa   4140
gatcagtgtt cttaactttt ttcttttttct tttttttttt ttgagatgga gtctccctct   4200
gttgcccagg ctgagggca gtggtgggat ctcggctcac tgcaaccttc acctcccagg    4260
ttcaagtgat tctcctgcct cagcctccca agtagctggg attacaggca cctgctatca   4320
tgcccagcta atttttgtat ttttgtagag actgggtttc accatgttgg ccaggctgtc   4380
ctgacctcag gtgatccacc tgccttggcc tcccaaagtg ctgggattac aggcatgagc   4440
caccacacct ggcctgttct taattttatt ggtcctgagt cacttagaat ctggtgacag   4500
cagtgagccc tcatcgtaga catatacatc catgcacaaa aggtatattc tactctaggg   4560
gatcatggat tcccgtagtg cacgcaggac cccagaaggt taagttccct gtgctagagg   4620
ccctctgagg cccgggcagc tgggaactgc tatggttctg ctctgagttg tctgaacttc   4680
cccctgcctg gatgcctccc tcccatgcag ctccttccct tgctctaggc cccactactg   4740
cctctgccag aggttccagg gctgccactt tgggtagaat gattcctctg tgcctcctct   4800
ccgagaaagt gaagggagtg agccagggcc taaactgtgg tacacttgtc caggaaaggc   4860
ctcttctcct tgcagtggag ggatggcacc aatgtcccca gcttctgcag catcagaggg   4920
ctcagtcccc catctcctgt ccagcctgct gggctccctg gggtctccct gcctctttca   4980
gcctgcctag gccccactgt aagctgctta ggcattaatt aaacccaccc ctgagcctgt   5040
gcttaatggc ctctccagcc gggactgccc agtaaaccca ccaatagtgc ctgactgggg   5100
cgtaggagga ggagcaagcc cagcaatttg gcttcgttgt tgcagaccac ttgatggggg   5160
cgtggtgggg gaggatgggg gacagggagt ggagacttgg ggtgtggcgg tgggttctgc   5220
ttcctcaaag gactcctggg gctcctgctc cccttcatgt tgttcgaggg gctgctcctg   5280
gcttctcata ttcaaaggaa gaagtacaaa gtgttttttct tccttcaggc agcctctgtc   5340
ctatcctgag ctacattagc tcccagcttc aaaaatctaa tggtggattc tgccccttat   5400
tatctggtgg tcattatact tcccacagga tagagagaca gctgtgtccc tgcctctgag   5460
ttcaggctcc cctccctcc tcctccctg ggagatccct gccttggact ctgcaaaggg    5520
caaagctaat aagatccttt ttccgcccttt ccccatgggt cagtatggtt gaagggaggg   5580
aaagggtatg ggtgtattcc tcttgcaggg agaccccata tctactttgg gtagagtcag   5640
gggccctttt cctgagactt gggagataaa tggacagtgg cactgggctg agaacttaga   5700
gatcctgaac ctggcatctc ctgacctgca gccttgctcc ctcttcccct gtcaccagat   5760
tccctcccttt ttttggatca aggctgggat atgtggctgc tttcaggtgg agctgtccct   5820
ttaaatctct cctccatccc tgggttactg tcctggtgtg taattctact gtcatggcaa   5880
ccagggtgc aatgcgacct ggtgccactc ctcagggaat gtctgagtgg aggctgcagt    5940
accctgatgg tggcctcttg ggcacaagat ctcagaggaa tggggtcacc ggagcggagc   6000
tgagtccttc ccttctgccc acactttttcc ctgtgtgcaa atgtgccctc attttttcctt   6060
tctggggaac tgagttccaa gtatgcctga cttgcttcct gggcatcatc cccttcatta    6120
agaggaagaa ctcatgggag atgggggagg ggaagaagct gctgtgaggc gagggggtaag   6180
```

```
cagggctggg gcaccatccc tacccacagc gatgccacct cccccacgta ccctgcctcc    6240
cagtggctga ccaagggtgg gtaggggggag gcgtctgagg cttgaggtat ttgccccatg   6300
cccaagtgag gctgcctccc ggtggagggc tgagtcgttc ttggggactt ccttagactg    6360
agggactatt gtaaaggaaa cagggcctgg agaggggact gagagcagag gtcagagggc    6420
atagggagga ggtggcatgg ggtgtattag aggagggggct tctagaaaag agggtacagg   6480
gacaagatgg gccaagactt ttctccctcg ggtctcctga agctggctgt gaggggaggg    6540
tctcggagta ccgcgccagt cttgaagggg cagcatgcct accccctcct caaaacttcc    6600
tgttagccgc ctcctcccca tccccaccga cactgacatg ctgggatcg ggcaatctgt     6660 gggactaggg ctccctccca ccactcttct cccacccggg ttaccgcctg ctctgcaccg    6720
cgcagcgcca gtcagggctt tagccaatca gcaaggcggt cacggcggct gagccttccc    6780
attggctggt tcctcagagg gcgctcctcg actcccgcct tccccagccc ggccaggctt    6840
tggctgggga ggcggtagac ggcggcgtgt aggacgctcc gggagtcccc gggtctgggg    6900
gccgccatgg caggcagccc aggcagcggg gtctccttgg agggtatatc cctggagtct    6960
tctgaggaag cggagctcca gagggaaggt agggaagggc gggccagatg ggggcggggc    7020
agctggcccc ttagcctacc ttcctccagc agagtcgggg catctgggga gggtggcctg    7080
ggagaggtca tctgagggca ccttcaggag agctgtcctg ggcagagggc accaactccc    7140
ttggctcagt cctcccctag ataacggagg gaatctggca taccctggca ggaagggaag    7200
ggtccctgcc ctgcctctt tcagagccca ctgagggcct cgcaggtctc tgaccaatgc     7260 caagcccgg cctgggcaag aggggtctga agggcaagct tgcactttt tttctggaga      7320 aggcagggag caggaggagg aaggagatgg gagtccagga gtccctgaac catctctgcc    7380
agctccagtt ccagtgcccc ctcctcccca ctcctgttcc ttcctggagg aggggggcac    7440
tgacaagagc attgagaggc gccaggggtg catcctccgc cgtcctccgt ggcttgggta    7500
ctgttatgca gatgtaggca tgggcggcat ggtggcagag taatgatacc cttcgcccat    7560
ctctgccccc agctgggcac attctgcttc tcgcttcctt tccccggaac ttgccacagc    7620
ctggaactcc cacctctgtc agtgagtgaa ggcagccctc acctcaggtc tcgggggcat    7680
tgttgcggcc cagctgcagg tgttatcgtg tcctccatta tgtcccattt cgggctgaga    7740
gtttgcttat ccctgtgatg acttggtgtg acctcagcct ttgggtcaca ccaaggcctc    7800
cagtgcctgt ttccctagct cctgccagcg ttccaggcct cagctttgac ttcctatcat    7860
ccatgttaat ttctcagtga ttatagatca ttgtcactca gagctgaagg cctgtaaaca    7920
tcatctagcc caatccatcc attttacagg caggaaagac tgaggccagt gagggacagt    7980
gacttgtaca atgtcacact gaattagtgg tgcttagact ggaggctgca ggccctggct    8040
cctgtgtggc tgcctgcttg actctgggcc tgtactcacg gacttgctcc gagtactgtc    8100
tgtctcatcc ttgagcctgc caggtacagg tggctgagcc ctgggcttca gcccatctag    8160
aggttgagtg aggagcttgt ggttttcttt tctttttctt ttttttttt ttgagacgga     8220 gtcttgcttc tgtcgcccag gatggagggc aatggcagga tctcagctta ctgcaacctc    8280
cgcctcctgg gttcaagcga ttttcctgcc tcagcctccc ggtagctggg attacaggcg    8340
cctgccacta cgcccagcta atttttttgta tttttagtag agacagggtt tccctgtgtt   8400
ggccaggctg gtcttgaact cttgacctca ggcaatccac ccgcttcggc ctcccaaagt    8460
gctgggatta caggcgtgag ccaccgcgcc cggccagaga cagtcttgct ctgccaccca    8520
ggctggagtg cagtggcgtg atctcagctc actgcaatct ctgcctcaca ggttcaagca    8580
```

-continued

```
gttctcctgc ctcagcctcc tgagtagcta gaattacaga cctacaccac tatgcctggc    8640 taatttggt attttagta gagatgggt tttgccttgt tgcccaggct ggtcttgaac      8700
tcctggcctc aagtgatcca cccaacagct tgtggttttc tggtgcaggg caggatctgc    8760
aacctgacac ctgcttccct ttctcccttc tctccacctc agagtctctt ccagctgcct    8820
ggagcctccc acctgctcag gctggcatta cctagggtgg agagaacagg ccaaggaaac    8880
tgtccccttc ctccaggatc cctgtcccag gcattcaagg cctggggtg cctgtgctgg     8940 gcagggaggg gaatgttgct ggggagggga atgttgccgg ggagggctg ccttctgtgg     9000 gacatggggg tggggaagtg gcaagtattg tggtgtgttt tggtcttctg tacccagctg    9060
gtacctgtgt atctcactgc ccgtaccttc ccccagccat gcagcaagtc ctggacaact    9120
tgggatccct ccccagtgcc acgggggctg cagagctgga cctgatcttc cttcgaggca    9180
ttatggaaag tcccatagta agatccctgg ccaaggtaca gtgctccagg gaggtgggca    9240
caagggcact gtgcttgggg aggcacagta ggggatgggg tattagctac agagggcttt    9300
gggaatggga catgtggcac aagaggcccc cctgaagggg attgtagaag aaaatcatgc    9360
ccaggtgatg acctgagtgg ctgcaggtag agggggctgc ccccacacct gtctggtgag    9420
tgcgtgggtg gatgtttgtt gactgccagc ttgtggagtg tgtgattggt gcgggctagc    9480
atgcacatgt tggagaatct ctagaattca tcttgcctgt ccttctgcct ttgggcgttt    9540
tgtgtgtatg tctttctaag gtcacctgcc atgtatcagg ttggggagag attcactaaa    9600
agagaaaatt ataggacaat ttggtaatga cagtgataga ggtggataca ctatgcattt    9660
tgggagcata aaggacaggt gtctaaccca gcctggggtg ggtgaggagg gcttcctgga    9720
ggaaggacca cttgagctga gtggaagaat gaggaagagg gggagggcat tctgggccac    9780
agaagagctt gagcagaagc acagaggtaa gaaagagtca ggagtgtgca ggggattgga    9840
agggctggtg tgaggctgag cctcaagtgt aagacaatgc gagctgtgca aaggttggca    9900
ggtctggagg gcactggggg ctgtatgtgg gtgcttgggc atccttctgt atcagggagg    9960
ctttatggtt tttttgttt tgttttgttt tgagaaggag ttttgctctt gttgcccagg    10020
ctggagtgca atggcgtgat cttggctcac tgcaacctcc acctcctgag ttcaagtgat    10080
tcttctgcct cagtctcccg agtagctggg attacaggca tgtgccacca cgcccagcta    10140
attttgtagt tttagtagag atggggtttc tccatgttgg tcaggctggt ctccaattcc    10200
tgacctcagg tgatctgcct gcctcagcct tccaaagtgc tgggattaca ggcatgagcc    10260
actgtgcctg gcaggcttta cattatttaa gcagggatat gatggccaaa tgtgggtgtt    10320
ttggcagcca tgtggaggac tgttgggggg ttatatctga agttgagag gccagttagt     10380 ggctcttcag tggattgagt ataagatgct gagagcctga aatggagctg tggtcccaga    10440
ccttagggta aactggtgga acttggtgtt tggcagtaag ggctagggta cagtaaggca    10500
cctgggatcc tgccccaggg agtgtggaag gatgcccct ctcctgaggg ggggaggtgg      10560
ggatggtgcc catggctgcg ttggaggcaa ggctgggagc tgtgggaaat cagacctaat    10620
tgctcagatt tcttggtgaa ggtggagcag tcctctcctg ggaattaggg atcagagatg    10680
gagcaggaag attcagaagg gaaggtttga ctggtcactg aaaggagaa ggaattaaat     10740 ggatggggac ctcgactgtc catgtcaggt gcccgatttc ccagggtggg ggtgactcca    10800
tccagagagg aagagaaagg agcggggct ttggtccagg gcacgtgctg gcctggggct     10860
gtggaagtcg gatgcaggga attgtgaagg gagctggtga gagaggctca gagaaaagag    10920
```

```
gcccaggctg gaaagaggca gaacagggag aaaatggagg tgaaggctcg gtggctctct   10980
gaggtcacag agtatttgag gggtgatggt agggatatag atggaagaga aaaagaccaa   11040
ggtcagagga agggaggtag gaggtgaaag ttttccaagg aggacagttc tagggatgcc   11100
atgataatgt agggtggggc tgcagtggac aggtaggtca tcagtgttga agacacccag   11160
aaatggaagg ctcaggagtg ggatgggctt gtccacacac ctattggcat gtagggctat   11220
ggcaggcgtc agggtgggga gaagactgag gcagtcccca gggttttcag tgcatggtgg   11280
tggaggtgac caggaagtcg gcaatgacag caagggtagg gagaaagaag gtacagccag   11340
gtggtgggtt ttctgtagag cggggactct gtcacaggct ggctatggct ggccctggca   11400
tgggatgtgg aggaccacgt cccactggag tggggattgc tgctgcaggg gacaccatgt   11460
ccttgggttg tagcctattc acattatctg tggaatggtt gaagacttgg gaagattgtt   11520
aacagcgaaa gatgaaaagt tgcagaggtt taatagtggg aagttctggg gaagagaaaa   11580
ctgagcagat tggaggagat tggagaaagg cagggtgctt ttcattcagc aatcgaagat   11640
cctactcatt tactaaagat aaagacaaga agctgggagt aggggcatgc acctgtagtc   11700
ccagctactc tggaggctga ggtgagagca ttgcttgagg ccaagaagct caagtgcagt   11760
tcatgtaaca tagtgagagc tcgtcttcaa taaataagta aataaataat aacaattata   11820
cacatttcaa acatagagac ttccatgaag gcaggaatgt ttgtcttttt gattcactgc   11880
agtatcccca gagcctacaa aatgcctgac acatagtagg tgctcactga atatttgttg   11940
aatgaataaa tacaaagag cataaaaaaa taacaaactc ctgagtaccc atctccaaaa   12000
tgttaataat gtttgttttg actcttgcca tttcttctta agaaataaaa agtatgaggc   12060
acacggcacg gtgtggctta cagctttagt cccagcactt tgggagacca aggtgggtgg   12120
atcatttgag ctcaggattt caagaccagc ctgatcaaca tggtgaaatc ctgtctctat   12180
aaaaaaatag aattagctaa gcatggtggc attcacctgt agtcccaact actcaagagg   12240
ctgaggcagg agagttgctt gagctgggta ggtcgaggct acaatgagcc atgatcatgc   12300
cactacagtc cagcctgggt gaccgagtga gacactgtct caaaaaaaaa aataaataaa   12360
taaataaaaa gtttggcaca gttaatgcct ctccccttcc tcattttcac tgcattccct   12420
tcccacaggt aaccactgcc tagagattga tgtcatttca ttgaatgttg gcttatcttg   12480
cctacatatg tgtttagctg taaacaatat acctttgtgg gatttttttt tagacagggt   12540
cttattccat ctcccaggtt ggagtacagt ggaacaatta tagctcactg cagcctggaa   12600
ctcctgggct caaatgatcc tcctgccctc ctgccttagc ctcctgagta actggggcta   12660
caaatatgta ccaccatgcc tggctaatct ttaaattttt ttgtagaggc agggtcttgc   12720
tacattgtcc aggctagtct caaactcctg gcctcaagta atcctctcag cctcccaaag   12780
cactgggatt ataggcatga gccaccatga ctggctctac ctttgttatg tgtgcttttt   12840
tttttttttt tttttttcctc tggagtctca ctctgttgcc caggctagag tgcagtggcg   12900
catttcggct cactgcaacc tccacctccc aagttgaagc gattcttctg cctcagctcc   12960
ccgagtagct gggactacag gcatgcacca ccatgcccgg ctaattttg tgtgtgtgtg   13020
tgtgtgtata tatatatata tatatatata tattttgaga tggaatctca ctctgtcact   13080
gggctggagt gcagtggcac aatctcagct cactgcaacc tccgcctcct gggttcaagc   13140
gattctcctg ccttagcctc ccaagtagct aggactacag gcatgcgcta ccatgcccag   13200
ctaattttg tattttttagt agagatgggg tttcaccatg ttggccagga tggtctcgat   13260
ctcttgacct cgcaatccgc ctgccttggc ctcccaaagt gatgggatta taggtgtgag   13320
```

-continued

```
ccaccgcacc tggccatttt tgtattttt ttttttttt tagtagagac agggtttcac    13380
catattggcc aggctggtct tgaactcctg acctcatgat tcgcctgcct cagcctccca    13440
aagtgctggg attacaggcg tgagccacca tgcctggcca ttacgtgtgc ttttaaattt    13500
tatataaatg aaatgatagt gtaaggtgct tctgttttg agatttctat ttcatacaag    13560
tagtacagct atcgacctaa gtatagatat agatagagat agggagattc atttgaactg    13620
cggtgtggtg ttctgataca gcagtcccca acctttttgg caccagggac cagttttgtg    13680
gaagacaatt tttccacgga tcagggtgag ggggtggtt ttggtatgca actgttccac    13740
tcagatcatc aggcatttgt tagacttctc ataaggagca cacaacctag atccctggca    13800
cgtgcagttc acgtagggt tggtgcccct gtgagaatct aatgccacca ctgatctgac    13860
aggaggtgga gctcaggcag taatgcttgc tcacctcctg ctgttcacct acttcctaac    13920
aggccacgga tcactactgg tccatggctt ggggttggg gaccctgtt ctaatatatg    13980 aatagagctg tttgtttatt ggttcccttc ctgagagatg tgtatgtcac tgctgatttt    14040
gctgtcttaa aaacagtgct gcagtgaaca tcctcatatc catctgcttc tgcatgcata    14100
tgagggtttc tctagaatgg acacttggca atgaaattga tgaatatgtg cagttttgaa    14160
cctcaacatc tgtaactttc caaaattgat ttcagagttg ggtttatgag cccacatcac    14220
ctctgggtac tttagctatt gtctccacag tgagacagtg agactctgct ttgtgatggc    14280
agagtctcag aatgagacag ccctcttgcc aataccttc aaagcagggt cccccttgat    14340
agcattcctc tctggtccag tccactcgac agtccactcg acagctctct aatgatgggt    14400
ttgctggctg gctggctatg tcattcactc atttgtccat ccatccatcc atccatccat    14460
ccatccatcc atccatcaaa tacctatttt gcactcgcca cataccaggc acagtgctgg    14520
ggttatggca gtgaactgcc agatagtttg ttttcctgat gaagcccaag tctgtcttcc    14580
tttcactgga caccacaatg ccccagtcct gggacctcac agtaaagcct aattgaaaat    14640
gaaccaatgt gctgtgtcac attgtaagta aactcccttc tctggaaacg tttttggcga    14700
gaagctggtc aggatttttt ccaagaaatt cctggtatgg ttccggattt gtagagcaca    14760
atagaagaga gtatggacgt ttcttccct ctgagacccc cagtatgagg ctaatgggct    14820
aaggcaatcc agtaacttct ttctccctgt ggttgtgaaa caaacaggaa gtgaatctcc    14880
ataaaggagc ctacctgagc ccactggaaa aaaaaagcc attcatttct tctgtccttg    14940
tatgggtgag cctttgcaat gtaaattgc cactcctctc atcaaagaca gtgtctctca    15000
gagctccctg cattggacaa tgggacctac ttcctccttc tcaccaattt taatcattat    15060
gtgtacacac acaatttct aacctaatag acaaagcact gtgatcaaag atccagctgc    15120
aaaaacttcg tgaagtggcc cagaaaccca caggaatgaa atcagattgg agccacatgt    15180
ggtagctgtt ggcctccctc ccttacgctg tggagctggg cttgactctg tctggggatg    15240
tggcagacag tgtaggaggg gccaggctgg gtagatctgg gaccagggag ggacagggcc    15300
tgaggataca aacccagagg gttaaaggcc ctaaggaag tcaagtctgg cagagagatc    15360
agaagtccag gcggttggct gcacacagca agtggcggcc ctggcaggtg gctggcatct    15420
gggacggctg acatggatcc agtagcaggt gttccagcta cagacaaggc caaggtgagg    15480
aatccaaggc aggggacatt cagaaattca gaaaattgt tactaatggg acagctgag    15540 aggcatgtga aggctgttgt gaactaattc acatgagatg aagaagaaag aacacaggc    15600 ttggagtcag aagattccac tgaccagctt tgtgagtttg gtatatctgt caacctctct    15660
```

```
gaacttcagt tatttcttat ggaggaattt ttaaaaaatt aatatttctt tatgtattta   15720 tttaaaaga aaggtgaggt ctcaccgtgt tgcccaggct ggtcttgaac tcctgagctc   15780
aagtgatcct cccaccctgg cttcctaaag tgctaggatt acaggtgtga gccaccatgc   15840
ccagcccagt tatttctttt gagaagtggg gagaatgata cctatccctc agagtcgtgg   15900
tggggctagg tggaggttat ggaagtgtaa gttttttttt tttttgagac ggagtcttgc   15960
tttgttgccc aggctggagt gtaatggtgc aatctcggct cactgcaacc tctgcctccc   16020
aggttcaagc gattctcctg cctcagcctc ccgagtagct gggattacag gccaccatc   16080 cccggctaat ttgtgtattt ttagtagaga tggggtttca ccatgttggc caggctggcc   16140
ttgaactcct gacctcaggt gatccaccca cctcggcctc ctcccaaagt gcaggaatta   16200
caggcatgag ccaccccggc cagaagtgat ttttgaatca ggaagagttg ttataatctt   16260
agcttcagac tagagttcac agggaggcct cttgttctgt ggggaggcta gggtggaaga   16320
cctgggaaag caagacaggg ccctagaaga ataaaggtct agggaggtca ctaagatagg   16380
ggctctgaca aggggacatg acaagcagag ggtgtagtgg tgaggccagt gtatcagttc   16440
acttttgctg tgtaacaaac catcgtgctg tgtcgtggct aaaacaact gtgatttaat   16500 tcccctgatt ttgtgggttg gttgggtggt tcttctggcc tgggcttgct tagctggggc   16560
tgggtggtcc gggatggcct cactcacatg tctggtgtct tagctgggaa aactgcaatg   16620
tctgggatgg ccagaccccc tttccatgtg gtctctcatc ctctaggagg gtctctcatc   16680
ctcagccacc ttcacatggt agtctcacaa gcaaggaagg acaagcctcc agtcacaagc   16740
actttctaag cctctgctca catttgataa tggcccattg gctaaagcaa gtcacatctg   16800
tcaaacccag attaaagagt tcctttactt tctgacacac tactctctgg gacatctttt   16860
aatttaacta tttaattatg aaccagggct tcaaatagga attccctgtc ttttgccatg   16920 atcgggggt tggagtggag ggcagaggga aaacttttca gtgaaatgac tgtgtagtgt   16980
ttgcatttgc agcctgctac agctctggat tgggagcaaa cagaacagag tgcaggctgg   17040
tgccactata aactagctgt gtctcccact taagcttctg gtctaccatg agcttgagcc   17100
cctgctttgc tgaggataat tttcagagca gaatgaaatg aatggctacc acagaaattc   17160
aaatcactct tctagttctg ggccatgtgt cacttaacat gaaaaagaag aataagtctt   17220
agcaaaataa tagtgagtaa aaaagtagta agggaaataa ttgttcactt aatgttaagt   17280 gaaaaaaat cagaccccag ggatggataa aatcatgatt ccccccttt tttatgtcat   17340 agaaaatacg gccgggtgcg gtggctcacg cctgtaatcc cagcactttg ggaggccgag   17400
gtgggtggat caccagttca ggagatcgag accatcctgg ctaacatggt gaaaccccgt   17460
ctctactaaa attacaaaaa attagccagg cgtggtggtg catgcctgta gtcccagcta   17520
ctcgggaggc tgaggcagga gaatggtgtg aacccgggag acggaggttg cagtgagccg   17580
agattgcgcc actgcactcc agcctgggca acagagtgag actctgtctc aaaaaaaaa   17640 aaaaaaaaa aaaacgcatt tggacagaca caattccctt tttattaact atattcattt   17700
cagaatttca gaagtatgta gaatacatac agacacatta caactcttta actgggaagc   17760
cagggaatga caaacacact aaatcaagat ggtgctttca gctgggcatg gtggctcatg   17820
cctgtaatcc cagcactttg ggaggctgag ccgggcggat cacctgaggt ctggagttca   17880
aggccagcct caccaacatg gagaaacccc gtctctacta aaaatacaaa attagccggg   17940
tgtgttggtg catgctgtaa tcccagctac tcgagaggct aaggcaggag aatcacttga   18000
acccgggagg tgtaggttgc agtgagccga gattgtgcca ttgcactcca ggctgggcga   18060
```

-continued

```
tagagcgaga ctctgtctca aaaaaaaaaa aaaaaaaaa gatggtgatt tctgcaagtg   18120
ggaagggtga gtggggcatg tggttagatg taggatattg acaagagctt tgttttttag   18180
tttgggtggt gggttctctt agatccttgt tatatcattt aaaaaatcta atttaggcca   18240
ggtgtggtgg ctcacgcctg taattccagc actttgggag gccgaggcag gcagatcacc   18300
tgagctcagg agtttgtgac tagcctgggc aacatggtga aacctcatct caactgaaat   18360
ataaaaaatt agccagggt ggtggcgcgt gcctgtagtc ccagctgttc gggaggttga   18420
agcacaagaa ttttttgagcc caggaagtgg aggttgcagt gagccaagat tgtgccactg   18480
cactccaatt tgggctacag agtgagactc cgtctaaaaa aaaaaaaaat tatttgttca   18540
gcctactgaa ttgttggttt tgtatttgaa tgattaaatg tttaaagttt cctctgggct   18600
atgaggttga gcttggagag ctgtgctttc atatctgtgg gtataaaacg tccagggtg   18660 gccacaggag gaggaatgga ttagcccatg gtgggaatgt cattaagtca aagataggag   18720
gtaagcagct taggaggcac cctggcttcc cccttgatca cacacgtctc ctcggaaaac   18780
ttgtcctcca tccgtggacc agatagtgct aaagtcaaaa tgagtgactt ctctaatgct   18840
cacatcagga cacctgtgcc agagctggct cctgttaacc caaagagcc atgcaagggt   18900 tgccatggtg agattgttgc tgcctgagtg ccattgttta ttcttgacac tcagttattt   18960
gggctttgat tccaacattg tcctaggcac agggtaatag agccagagct gggacgcctc   19020
cctcactctg gggctccata ggctgggcca agctaaatga ctgaaagtca catagggtc   19080 tgtggaagac cagccctctg gggcttgttc ctttccccaa atgctactcc tctgccccat   19140
cagttgtctg tttccccagt aggttgtgga tgtcagtcta aaatgctgcc cacccggcag   19200
aggatggtat gggaggctgt ggggccatgt gggtgctgt tccctggcct gtttgggaaa   19260
agagaaggca gaaagcatct aacctttatt gagcacctgc tgtctgccag gcactatgtc   19320
catctcacca aatcctcaca gcagtcttat gaagtattac tcaaatctca ccatctcatg   19380
gctaaacaaa ttttctatta tgaaaaaatt taagaatata tcctgaacct ccatcaccta   19440
gcaccccact tcaacattca acaagtcatg cataatcttg tttcatccac acctttacca   19500
gcttccctct ctcctccatt gttttggagt acatctcagc cataatagat tgtatctgca   19560
agtgtttcat tgtgtatata aactcctggg ctcaactgaa aaggattctt taaagctaca   19620
ctactattct cacacctaaa aaaaaatcaa acaatagttt tcttttgaat tttttttaatt   19680 aaaaaaattt taaaaaatag agatggggtc ttgctgtctt gaactcctgg gctcaagtga   19740
tcctcctgcc ttggcctccc aaagtgctgg gattacaggt gtgagccatt gtgccctgcc   19800 atgaatttt aataaatggt attggaacat ctggatagtc attttgaaag atatcaaagt   19860
gtatttattc ctcacatcat atatcagaat aaactccaag cggatcagag atctctatgt   19920
gaaaatataa atcatacacg tcctagaaga aaacaaggct ctgtatatgg aaaagcccct   19980
cccttaaaaa aaaacaaaaa aaacaaaaaa ctatgcctca aaattcagat gcatgaaaga   20040
ttattaaatt cacccacatt aaaaaatttg ttttttgagc cagggtcttg ctctgtcact   20100
caggctggag tgcagtagtg caaacagtgc tcactgcagc ctcaatctcc tgggttcaag   20160
tgatccttcc acctcagcct cccaagtaag agtagcaggg acatcaggtg catgccacca   20220
tgcattaaaa tgaggattaa aaatgctcag gtgaattttt aaaatatttt gtagcaacag   20280
gggcttccca tcttacccag gctggtcttg aactcctggg ctcaagcagt ccttcctcct   20340
tgacctccca aagtgttggg attgcaggtg tgaaccactg cacctgacct aaattttttt   20400
```

-continued

```
ttttttttttg catgcaaaaa caccacaagc agagtcaaaa gacaagtgac aaactggggg    20460
aaatcattta caagaaatat cacaaagggc taattttccc aatagagaga aaacattttt    20520
taaaataggg aaaagaataa aaaccaagac ctgacagaaa aattgggaaa gacatgagta    20580
gacagttcac agaaaaagat atacagatgg tccttaatca tatggagaga tgtttgactt    20640
tactcataat aagcaaaatg caaagtaagc cccaatgaga gatcatttct cctccatgtg    20700
attggcagac atgcaaatgt tgatcaaca ctctggtggt gagcttcaag aaaatccctc    20760
atacagtgct agcaggagag caaactggcc aaagtcccat ggagggaat tgtcaatat    20820 ctaagaaaat tacgtatgta tttgctgctt gacccagcaa gacttctagg aatttacatg    20880
gaagatcttc tccacagata tagaatacta tgccggagtc atttactgca acattatttg    20940
caatagcaaa gtattagaaa caacctaaat acccatggag actggttgaa taaattacag    21000
gaatccagtc atgcaatgga gtcaaatgca gtaattaaaa taataagatg ggcatggtgg    21060
ttcatgcctg taatcccaac ctgggaggca gaggttgcag tgagctgaga tcgcgccact    21120
gcactccatc ctgggtgaca gagcaagact ctgtctcaaa caaactaaca ataataatta    21180
ataaaggaag atctccatgc agtttcatgg agtgatttct atgacatatt tttaaataaa    21240
aagccagaaa accaaaccag ttaaataaaa gccctagggt atcaaagggt atatacagtg    21300
ttactgtgtt ttatgtaaga aagggcaata tatttattta attttttttt ttggaaacag    21360
agtcttgctc tgttgcccag gctggagggc agtggcgcga tctcagctcc ttgcaacctc    21420
tgcctcccgg gttccaagtga ttctcatgac tcagcctcct gagtagctgg gattacaggc    21480
atgtgccaca tgcccggcta attttgtatt tttggtagag atggtgtttc accatgttgg    21540
tcaggctcgt ctcaaactcc tgacctcagg tgatcctcct gccttggctt cccaaagtgc    21600
gggattacag gcatgagcca ctgtgcctgg cctttagtgg tgatttctga gattttgatg    21660
cacccatcac ccaagcagta tacactgtac ccagtgtgta gtcttttatc ccttacgccc    21720
ctactaccct tcccggctga ttttttactaa tagatttgtg ataggtagta gcagttgtat    21780
agcaattttg aaactgcttt gaatattgaa ggacagaaca aataagtaaa tatactgatg    21840
ttattgggaa ataagttctc actgaaggag aagggagaca caaatatgga atgggggaag    21900
atgagaaaaa tccttttaatt ttatttggag ccattagtat ctactaatga ctgccaaaga    21960
aatgatgccc agaaacaatg ggtattgagt gtccacatct tggtttctaa atactatctc    22020
ctgctaaaag gaatcagggt tccttggaga aattgctgat tccagacctg gggtagggaa    22080
tgcatcagat gagcctgtgc cagaagggaa gaagatgctc aaggactgat gggaacatgt    22140
caacaggaca gaggtgtgaa tggggctccc actggacaaa tttgggataa actgggtcaa    22200
cgaagatagt gatcgtaatg gattagaaca catgaataa aaaaaattca tagtgatatc    22260
atgagagaga gaaggagaga aagaggagta aggtggtagg gagaaaagaa gagctcattc    22320
tttttttttt ttttttttga gctggagttt tgctcttgtt gcccaggctg gagtgcaatg    22380
gcatgatctc ggctcattgc aacctccacc tcccaggttc aagcggttct cctgcctcag    22440
cctcctgagt agctgggatt acaggcgccc accactatgc taggctaatt ttttatatct    22500
gtagtagaaa cggggtttca ccatgttggc caggctgttt tgcaaactcc tgacctcagg    22560
taatccacct gccttggcct cccaaagtgc agggattaca ggcgtgagcc actgtgcctg    22620
gctgaaaagc tcattcttat agcagaatgc caataaatgt agaaggaatg atgggaatta    22680
ggtaatcact atttttgcaac ctccagtata ataactcatt taggcaaggg tcataaattg    22740
acactaaatc cattggtgaa ggattttggg gtaacagaat agtcacatag tctcaaagta    22800
```

-continued

```
tgggaaagac acaaagacac aagatcacct acgtagaact cttgtcaaaa ggattaacgt    22860
aagtctaatc atgaggaaac aatcaactaa atctagtggt agagcatcct aaaaactact    22920
ggcctggagt ctaaaaatgt ctaggctggg tgcagtggct catgcctgta atctcaggct    22980
ttgggagcct gaagcaggag gatcacttga agccaagagt ttgagactag cctaggcaac    23040
gtagtgagac cctgtcccta caaaacaaaa acagaaacaa aaaaaacaaa acaacaaatg    23100
ttctgaaagt ctaaaagtta ttgggatctg ttctagatta gaggagaata aaagatatg     23160 tcaaccaact acaacatatg atcatcaatt agatcctgaa tcagaaaaaa taaaattata    23220
aaggatactt ttgggacaag agtgaacatt tgaatgtgga ctgtcttaca taatgtatta    23280
atgaatcgat gttaaatttc ttgcaggtga taatggtatt gtggtttatg cagcagaatg    23340
tctttgttcc tatgaaatac atgctgaaat actttgggt  aaagtggctt gtgttgtctg    23400
caatgatctt tcaaagattc agaggggaaa aatggtcttc atatatatta ttgaaatgga    23460
attcttttct tcctgaccca tctaacctaa cactccccac tgggctggtc actggcgaag    23520
gattcctttt ctgttttcag cgctccttgg tatggagccc ggagccagca gagcaacaaa    23580
taggtgcagg gcctgctcct ggcaccgtgt tctgatttcc tgtcccctca ttcgctggga    23640
acactgagtt gagggcctgg agacgcaagt tcaagtccca ttgaccctgg gaaagttatt    23700
ctacctccct aatttcctca tcctgggctt cagggtcttc aaggcccac  ccaaccatga    23760 tgtctggtgg aagaagccgt ctttgaacgc caatgcatat agggtcctgg gagctgggga    23820
caatttggta acttctaatg accctctgtg gcaagggaat ggaaaggaag gtttgtcctt    23880
tggtttcttc cttccctaaa ctaggtccta gtaattttgg ggaagaaagg agacagcaag    23940
gaatgcatgt gcacgtgtgg gtatgattgt cagtgagtga ggagctgaag ctgggggctg    24000
gggggtggga tgggaaaat  gcctggggc  tgagggagga ccctgcttgg tgtcccaggg    24060
ctcctgggga agctcctagc cccacctgtt ctgcttccac ccccaggccc atgagaggct    24120
ggaggagacg aagctggagg ccgtgagaga caacaacctg gagctggtgc aggagatcct    24180
gcgggacctg gcgcagctgg ctgagcagag cagcacagcc gccgagctgg cccacatcct    24240
ccaggagccc cacttccagg ttcctggctg ctagggctgg ggtgagggag caggaggtgg    24300
gtggactggg gcatgctgct gttggatggg ccagcaggaa gttggatctg ggatgggaag    24360
agacccggga cactgcccca ttgtcccttc tcttcccacc acccccagt  ccctcctgga    24420 gacgcacgac tctgtggcct caaagaccta tgagacacca ccccccagcc ctggcctgga    24480
ccctacattc agcaaccagc ctgtacctcc cgatgctgtg cgcatggtgg gcatccgcaa    24540
gacagccgga gaacatctgg tgaggactgg gcagggccag aggtggtgct ggtgagggtg    24600
gggggattga gaataaccaa tgaacggaca aaaaaggcca agtgtggtct gaagatgaag    24660
atggggccag ctttgtgcag ggaaggatcg atgcagcaaa gggtcggggg aagacccagg    24720
agaccataga cactgcacac acacctgtgt ccgcacctct ccagtctgcc cacctctccc    24780
ctcattagta cctgctgtaa gtgaagaatt taggcagaag gatggaggag gactttgtga    24840 gggtggggt  gggtgggtag ggacaggaat ggaggagcta ttaggagact atttgaagat    24900
tctgacttgg agcaattggg gcctcatctt acactccctc tgacctccag ggtgtaacgt    24960
tccgcgtgga gggcggcgag ctggtgatcg cgcgcattct gcatggggc  atggtggctc    25020 agcaaggcct gctgcatgtg ggtgacatca tcaaggaggt gaacgggcag ccagtgggca    25080 gtgaccccg  cgcactgcag gagctcctgc gcaatgccag tggcagtgtc atcctcaaga    25140
```

```
tcctgcccag ctaccaggag ccccatctgc cccgccaggt gggcccctca cccagcacaa    25200 gcccaaggg atggctgagc ctcctggctg tcaaggttgc aggtctcacg gaggccctcc     25260
tctcctactg gtttcctcca gggaagatgg ggggtgggac ctgcagccca ggggcagctg    25320
accgcagccg ccgacaggcc tctgccgctg ctgcacctgc acatgctccc acattggctg    25380
gtattatgca cgcagccaca gcctgggta caagtgtatg agagagcgcc tgcattatgg     25440
tcagcgttct tcacgtttgt gcgcgtgcgc agggtgcggt tgtcatatgt cctggatagc    25500
tgtctcctgg ttggtcaatt ctggggtgt ggctgctctg tctccctatc ctattgggtc     25560
tctcgccctc caccagagcc cttctccaag ggagagggt gagtggaggg agggatccag     25620
gattaggtgc cagggtcctg tgccctactt ggtggtcccg catccttggt cctgagatct    25680
gaatcctgta gtactagatg caaagggagg ttggcaccag ggaggagcat gggcaggcct    25740
ggaggcatca ctcctgcagg gggacagttc cattgcccct tagtctctgt gaaagaggg    25800 ggcatggggt agacctccac ctgcagcctt ctgctgaccc ttcccccgac ctttgctga    25860 ttcctgggcc caggtatttg tgaaatgtca ctttgactat gacccggccc gagacagcct    25920 catccctgc aaggaagcag gcctgcgctt caacgccggg gacttgctcc agatcgtaaa    25980
ccaggatgat gccaactggt ggcaggtgag ctgcgggcac ccccgcatct ctccaggtat   26040
ggtgcatggg agggcgaggg cacagggagg ggtcctcttg ctcaggcaga tcttggtctc   26100
atgtccgttt taggcatgcc atgtcgaagg gggcagtgct gggctcattc ccagccagct   26160
gctggaggag aagcggaaag catttgtcaa gagggacctg gagctgacac caaactcagg   26220
taggaggtcc cccctacccc acacctccaa tctgggatcc aacagggccc tgtctgcctc   26280
actcacccat ctccctatgg ccagggaccc tatgcggcag cctttcagga aagaaaaaga   26340
agcgaatgat gtatttgacc accaagaatg caggtgggta tcagagcgcc ccctccctta   26400
ccctcctcta acatggcatg cctttccctg tccccaccca tcacctgtga cgacgtgtgc   26460
ctggctcaga tgctgccagc cgtgtcccta ggccctgccc gactcccccc tgctcccctg   26520
ttccaagccc tcttgccctc agcctccctg agagctccgc ccctccctca ccgtgcagcc   26580
tggtgagcag cgccatctcc ctgtgtccag agtttgaccg tcatgagctg ctcatttatg   26640
aggaggtggc ccgcatgccc ccgttccgcc ggaaaaccct ggtactgatt ggggctcagg   26700
gcgtgggacg gcgcagcctg aagaacaagc tcatcatgtg ggatccagat cgctatggca   26760
ccacggtgcc ctgtgagtgg gagctgggcc ctgctgagtt ggggacaagg agcagggctc   26820 ccctgggcc agggctgggc ccaccgaatg ggcatcttca tgggcaccag gccaggtggt    26880
acctttgggt acacggggttg gggtgcacgc cctctgtggg tggttagggg aacttcaggc   26940
tcaggaaggg tgagggaggt gtccagccaa caggtggcct agcgggctgg gctggcgtcc    27000
actttccttc tcttgtttca cttgctaaaa gccatgaaga aagtgagtgc ccagctgtgc    27060
acccgggtga acaggctac gagctgcatg tgtgtagcct tgtggaagac agggcttctt    27120
agtggcagaa acagcggggg tggtggaagc tcctggctgc cagaggcagg actaagagca    27180 ctgcccctggt ctgcttggct cttgctgtgt ggctttgggc tgtacattgc cctttctgga   27240
cctcagcctc tcttctgtgg gctctgggct ggaccatgat taccagctca tgtctctgtg    27300
tgtgccaatg gggagagtgg ggggcaggtg tgtgcaaagg cagcagtgct ggcaagatgg    27360
ggagcagact gcacctccaa ggctgggaaa cgggggcctg ggtaggggtg catatatgtg    27420
tctgaggcac tgtaacctgc ccctgcccat ttggtccaac ctaccccat cccctagac     27480 acctcccggc ggccgaaaga ctcagagcgg gaaggtcagg gttacagctt tgtgtcccgt    27540
```

```
ggggagatgg aggctgacgt ccgtgctggg cgctacctgg agcatggcga atacgagggc    27600
aacctgtatg gcacacgtat tgactccatc cggggcgtgg tcgctgctgg aaggtgtgc    27660 gtgctggatg tcaaccccca ggtaccgcca ctctgctcct tcccagcctg cccaatgtcc    27720
tctctgctgc ctcattgctc ccccatatag ttccagacac ctgtcacctg aacacgccca    27780
tgtaccccct ttgccctcaa ctactgctag aaacccagcc cacctggaac ctttctcagc    27840
cttccagggt ccccactcct cctctagtct cctccagtca cccagccac ctgccagctg      27900 tttgtcattt gtcccaggac tcatgtccca gaccccggg cacccttttc tcatccactc       27960
ccaagtgctc accccaaccc cagttaccct cacagccttt ctctggttcc taggacagac    28020
atggggatat actccctacc ttgccttctc cttctgcagg cggtgaaggt gctacgaacg     28080
gccgagtttg tccccttacgt ggtgttcatc gaggccccag acttcgagac cctgcgggcc   28140
atgaacaggg ctgcgctgga gagtggaata tccaccaagc agctcacggt gagggctctg    28200
aggtgtgggg gagggtctg atagctgcct agggtggtgg gggacaggcc tgagctgaca     28260
gagagaagga ggtggtgttg gggagggaca ggggcctgct ccagttatca gtgaggcagg    28320
acgtggtccc ccctgcatag atgtggaagg ggaggtctga gagaggaagt ccaaagtctc    28380
agagtgagcc aggcacacac ctagcctggg atacatgtgc ttctgactca aggcccccgg    28440
ctcagcccac tctgcagaga cagagtgctg gccagagaga gttcccgagg gcaactggga    28500
gaggtgggct ggaggtgggc caggtgagct tgggttgctt acagctgggg gaaagctgaa    28560
gggtaggaga aagccagagg cgggaaggct ggctggaggg ctgagtcagc gtcagggagc    28620
aggcagcgcc tggaggagag gcttcaaggc ctcattgcag aactccagcc ccatcctcct    28680
tcctatgtct tgctgcgcct tcccaggagg tggagggttt gcggcgctct gagcgcaggg    28740
gtccctctgc tggccatgcc tggtgctgca gcattccggc cccaggtcag agcgtgcctg    28800
gggcccagga gaggctgtct aggctggcac ccttctgcca atgaccccct taaggagctc    28860
tggacctttg cctgatcccc attctgggca cctcctcctt ggcaacaggt gtggccaact    28920
ggagctgttg ggatgcagct agcttcagct tatttaagtc agttgtcaag taccccttcct   28980 cacccctgcc catccagctt ccactgggtc gagggtgggg ttgccctggg tacttgtgga    29040
ttgccctggt accagcctgt ctagctgcat aggtaaggca gcctagtcag acttgaggga    29100
gcactggctt gagagtcagg cagaccctgt ttagccactg actggctatg tgacctttt     29160 ataccttcat tttctctgct ataaatggga aagaattaat cctatcttgc agagctgtag    29220
tgaagattat gtggcatgca aagcatttag gggtgtgatt ggcagttatt aaagcttatt    29280
tcctcccttt cactcaccat ctgtggttga tggtgagcca cttt gaggca cgcagagagg    29340 ggccctgcc tccctagcca gggagtccac accaggggtg ggctttgggg agggggagtg     29400 gggcagctg tagctccttc tgacagtggg ggtgagttgt gggcactgac tgtagggagg     29460
tccccttgtg cctgggcagg aggcggacct gagacggaca gtggaggaga gcagccgcat    29520
ccagcggggc tacgggcact actttgacct ctgcctggtc aatagcaacc tggagaggac    29580
cttccgcgag ctccagacag ccatggagaa gctacggaca gagccccagt gggtgcctgt    29640
cagctgggtg tactgagcct gttcacctgg tccttggctc actctgtgtt gaaacccaga    29700
acctgaatcc atcccctcc tgacctgtga ccccctgcca caatccttag cccccatatc     29760
tggctgtcct tgggtaacag ctcccagcag gccctaagtc tggcttcagc acagaggcgt    29820
gcactgccag ggaggtgggc attcatgggg taccttgtgc ccaggtgctg cccactcctg    29880
```

```
atgcccattg gtcaccagat atctctgagg gccaagctat gcccaggaat gtgtcagagt    29940
cacctccata atggtcagta cagagaagag aaaagctgct tgggaccac atggtcagta     30000 ggcacactgc cccctgccac ccctccccag tcaccagttc tcctctggac tggccacacc    30060
caccccattc ctggactcct cccacctctc acccctgtgt cggaggaaca ggccttgggc    30120
tgtttccgtg tgaccagggg aatgtgtggc ccgctggcag ccaggcaggc ccgggtggtg    30180
gtgccagcct ggtgccatct tgaaggctgg aggagtcaga gtgagagcca gtggccacag    30240
ctgcagagca ctgcagctcc cagctccttt ggaaagggac agggtcgcag ggcagatgct    30300
gctcggtcct tccctcatcc acagcttctc actgccgaag tttctccaga tttctccaat    30360
gtgtcctgac aggtcagccc tgctccccac agggccaggc tggcaggggc cagtgggctc    30420
agcccaggta ggggcaggat ggagggctga gccctgtgac aacctgctgc taccaactga    30480
agagccccaa gctctccatg gcccacagca ggcacaggtc tgagctctat gtccttgacc    30540
ttggtccatt tggtttctg tctagccagg tccaggtagc ccacttgcat cagggctgct     30600
gggttggagg ggctaaggag gagtgcagag gggaccttgg gagcctgggc ttgaaggaca    30660
gttgccctcc aggaggttcc tcacacacaa ctccagaggc gccatttaca ctgtagtctg    30720
tacaacctgt ggttccacgt gcatgttcgg cacctgtctg tgcctctggc accaggttgt    30780
gtgtgtgtgc gtgtgcacgt gcgtgtgtgt gtgtgtgtgt caggtttagt ttggggagga    30840
agcaaagggt tttgttttgg aggtcactct ttggggcccc tttctggggg ttccccatca    30900
gccctcattt cttataatac cctgatccca gactccaaag ccctggtcct ttcctgatgt    30960 ctcctcccctt gtcttattgt ccccctaccc taaatgcccc cctgccataa cttggggagg   31020
gcagttttgt aaaataggag actcccttta agaaagaatg ctgtcctaga tgtacttggg    31080
catctcatcc ttcattattc tctgcattcc ttccgggggg agcctgtcct cagaggggac    31140
aacctgtgac accctgagtc caaacccttg tgcctcccag ttcttccaag tgtctaacta    31200
gtcttcgctg cagcgtcagc caaagctggc ccctgaacca ctgtgtgccc atttcctagg    31260
gaaggggaag gagaataaac agaatattta ttacaaatgt tagaatatat ttcttatact    31320
aggaatctca tttgcatttg catagactat acacatgggg tggaaaggcc aggcctgccc    31380
ccatctcgtt ggtgtggctc tgcgtatact acacactcat tctcctgctc ctcttttccc    31440
ttagtcagtg tcctttcatc ctgattcagc tctgccttgc atcaccctca gcctaaggga    31500
gtgggaagga aatggggtgt tttcttgctg acctgaggct ataggtcac ttgccatttc     31560 ctaccttctc tgggggattt gagggtagag gcaggggaag atctgttgtt gcagttgctt    31620
ctgccccctt gatccaaatg accatcatct ctgatggaga tgggttgggt acctggcctt    31680
catggcacct tcactgctag ggatgctcaa ggggcaggcc tggggcccctt cctcctgtc    31740 tcttctcggt cttttcctctc tgagcagcct cctacctccc ctgcctgagc cctcactcca    31800
cagccctccc aggtacctag cagaggctgt cagtccttgg ctcacctgga acagggctgg    31860
ggctgggttg gaacaggtgt gtgccccac cacagctcta tgactctgtt ctccctccct     31920
gccattgtgg actcttgtat ttgagggacc tcaagagagt gaggaccta ccatccactg      31980 tccatattca gtcccagccc cagtgcgctt cctctgttcc ctccctcagc catccaattc    32040
ttgagttttc tcactgattg gttttctttc tttttccttg gattaaatgt gaaagcaaag    32100
gcttctggct ctgcttttct ttggttgggg ttggatggat ggctttggga gagagtgaga   32160 gctgggagc acagcacaga tgactactag aatggaagtc agagcaacat gtcttgtttt     32220
ctgcgatgtc ttccttttcct ctgtcttgcc cctgcacact cccccatccc cagaagatgc    32280
```

-continued

```
tccttctaag tgcttgtacc caaggacatg aacagacatt tctcaaaaga agacatacaa    32340
gtgacaatgt atgaaaaagt gctttacgtc actaatcatc agagaaatgc aaaccaaaac    32400
taccatgagt taccatctca caccagtcag aatggctatt aaaaggtcaa aaaataagag    32460
atgctggtga agttgcagac aagagggagt gcttatacac tattggtggg aacgtacatt    32520
agttcagccc ccgtggaaag ctgtttgggg agttctcata gaactaccat tcattccagc    32580
aatcccatca ctgggcatct acccaaagga gaagaaatcg ttccaccaaa aagatacctg    32640
cacttgtgtg actg                                                      32654
```

<210> SEQ ID NO 4
<211> LENGTH: 576
<212> TYPE: PRT
<213> ORGANISM: Homo sapiens

<400> SEQUENCE: 4

```
Met Pro Val Ala Ala Thr Asn Ser Glu Thr Ala Met Gln Gln Val Leu
 1               5                  10                  15

Asp Asn Leu Gly Ser Leu Pro Ser Ala Thr Gly Ala Ala Glu Leu Asp
            20                  25                  30

Leu Ile Phe Leu Arg Gly Ile Met Glu Ser Pro Ile Val Arg Ser Leu
        35                  40                  45

Ala Lys Val Ile Met Val Leu Trp Phe Met Gln Gln Asn Val Phe Val
    50                  55                  60

Pro Met Lys Tyr Met Leu Lys Tyr Phe Gly Ala His Glu Arg Leu Glu
65                  70                  75                  80

Glu Thr Lys Leu Glu Ala Val Arg Asp Asn Asn Leu Glu Leu Val Gln
                85                  90                  95

Glu Ile Leu Arg Asp Leu Ala Gln Leu Ala Glu Gln Ser Ser Thr Ala
           100                 105                 110

Ala Glu Leu Ala His Ile Leu Gln Glu Pro His Phe Gln Ser Leu Leu
       115                 120                 125

Glu Thr His Asp Ser Val Ala Ser Lys Thr Tyr Glu Thr Pro Pro Pro
   130                 135                 140

Ser Pro Gly Leu Asp Pro Thr Phe Ser Asn Gln Pro Val Pro Pro Asp
145                 150                 155                 160

Ala Val Arg Met Val Gly Ile Arg Lys Thr Ala Gly Glu His Leu Gly
               165                 170                 175

Val Thr Phe Arg Val Glu Gly Gly Glu Leu Val Ile Ala Arg Ile Leu
           180                 185                 190

His Gly Gly Met Val Ala Gln Gln Gly Leu Leu His Val Gly Asp Ile
       195                 200                 205

Ile Lys Glu Val Asn Gly Gln Pro Val Gly Ser Asp Pro Arg Ala Leu
   210                 215                 220

Gln Glu Leu Leu Arg Asn Ala Ser Gly Ser Val Ile Leu Lys Ile Leu
225                 230                 235                 240

Pro Ser Tyr Gln Glu Pro His Leu Pro Arg Gln Val Phe Val Lys Cys
               245                 250                 255

His Phe Asp Tyr Asp Pro Ala Arg Asp Ser Leu Ile Pro Cys Lys Glu
           260                 265                 270

Ala Gly Leu Arg Phe Asn Ala Gly Asp Leu Leu Gln Ile Val Asn Gln
       275                 280                 285

Asp Asp Ala Asn Trp Trp Gln Ala Cys His Val Glu Gly Gly Ser Ala
   290                 295                 300
```

Gly Leu Ile Pro Ser Gln Leu Leu Glu Glu Lys Arg Lys Ala Phe Val
305                 310                 315                 320

Lys Arg Asp Leu Glu Leu Thr Pro Asn Ser Gly Thr Leu Cys Gly Ser
            325                 330                 335

Leu Ser Gly Lys Lys Lys Arg Met Met Tyr Leu Thr Thr Lys Asn
            340                 345                 350

Ala Glu Phe Asp Arg His Glu Leu Leu Ile Tyr Glu Glu Val Ala Arg
            355                 360                 365

Met Pro Pro Phe Arg Arg Lys Thr Leu Val Leu Ile Gly Ala Gln Gly
            370                 375                 380

Val Gly Arg Arg Ser Leu Lys Asn Lys Leu Ile Met Trp Asp Pro Asp
385                 390                 395                 400

Arg Tyr Gly Thr Thr Val Pro Tyr Thr Ser Arg Arg Pro Lys Asp Ser
                405                 410                 415

Glu Arg Glu Gly Gln Gly Tyr Ser Phe Val Ser Arg Gly Glu Met Glu
            420                 425                 430

Ala Asp Val Arg Ala Gly Arg Tyr Leu Glu His Gly Glu Tyr Glu Gly
            435                 440                 445

Asn Leu Tyr Gly Thr Arg Ile Asp Ser Ile Arg Gly Val Val Ala Ala
            450                 455                 460

Gly Lys Val Cys Val Leu Asp Val Asn Pro Gln Ala Val Lys Val Leu
465                 470                 475                 480

Arg Thr Ala Glu Phe Val Pro Tyr Val Val Phe Ile Glu Ala Pro Asp
                485                 490                 495

Phe Glu Thr Leu Arg Ala Met Asn Arg Ala Ala Leu Glu Ser Gly Ile
            500                 505                 510

Ser Thr Lys Gln Leu Thr Glu Ala Asp Leu Arg Arg Thr Val Glu Glu
            515                 520                 525

Ser Ser Arg Ile Gln Arg Gly Tyr Gly His Tyr Phe Asp Leu Cys Leu
            530                 535                 540

Val Asn Ser Asn Leu Glu Arg Thr Phe Arg Glu Leu Gln Thr Ala Met
545                 550                 555                 560

Glu Lys Leu Arg Thr Glu Pro Gln Trp Val Pro Val Ser Trp Val Tyr
                565                 570                 575

<210> SEQ ID NO 5
<211> LENGTH: 576
<212> TYPE: PRT
<213> ORGANISM: Homo sapiens

<400> SEQUENCE: 5

Met Pro Val Ala Ala Thr Asn Ser Glu Thr Ala Met Gln Gln Val Leu
 1               5                  10                  15

Asp Asn Leu Gly Ser Leu Pro Ser Ala Thr Gly Ala Ala Glu Leu Asp
            20                  25                  30

Leu Ile Phe Leu Arg Gly Ile Met Glu Ser Pro Ile Val Arg Ser Leu
            35                  40                  45

Ala Lys Val Ile Met Val Leu Trp Phe Met Gln Gln Asn Val Phe Val
    50                  55                  60

Pro Met Lys Tyr Met Leu Lys Tyr Phe Gly Ala His Glu Arg Leu Glu
65                  70                  75                  80

Glu Thr Lys Leu Glu Ala Val Arg Asp Asn Asn Leu Glu Leu Val Gln
                85                  90                  95

Glu Ile Leu Arg Asp Leu Ala Gln Leu Ala Glu Gln Ser Ser Thr Ala

-continued

```
                100                 105                 110
Ala Glu Leu Ala His Ile Leu Gln Glu Pro His Phe Gln Ser Leu Leu
            115                 120                 125
Glu Thr His Asp Ser Val Ala Ser Lys Thr Tyr Glu Thr Pro Pro Pro
        130                 135                 140
Ser Pro Gly Leu Asp Pro Thr Phe Ser Asn Gln Pro Val Pro Pro Asp
145                 150                 155                 160
Ala Val Arg Met Val Gly Ile Arg Lys Thr Ala Gly Glu His Leu Gly
                165                 170                 175
Val Thr Phe Arg Val Glu Gly Glu Leu Val Ile Ala Arg Ile Leu
            180                 185                 190
His Gly Gly Met Val Ala Gln Gln Gly Leu Leu His Val Gly Asp Ile
        195                 200                 205
Ile Lys Glu Val Asn Gly Gln Pro Val Gly Ser Asp Pro Arg Ala Leu
    210                 215                 220
Gln Glu Leu Leu Arg Asn Ala Ser Gly Ser Val Ile Leu Lys Ile Leu
225                 230                 235                 240
Pro Asn Tyr Gln Glu Pro His Leu Pro Arg Gln Val Phe Val Lys Cys
                245                 250                 255
His Phe Asp Tyr Asp Pro Ala Arg Asp Ser Leu Ile Pro Cys Lys Glu
            260                 265                 270
Ala Gly Leu Arg Phe Asn Ala Gly Asp Leu Leu Gln Ile Val Asn Gln
        275                 280                 285
Asp Asp Ala Asn Trp Trp Gln Ala Cys His Val Glu Gly Gly Ser Ala
    290                 295                 300
Gly Leu Ile Pro Ser Gln Leu Leu Glu Glu Lys Arg Lys Ala Phe Val
305                 310                 315                 320
Lys Arg Asp Leu Glu Leu Thr Pro Asn Ser Gly Thr Leu Cys Gly Ser
                325                 330                 335
Leu Ser Gly Lys Lys Lys Arg Met Met Tyr Leu Thr Thr Lys Asn
            340                 345                 350
Ala Glu Phe Asp Arg His Glu Leu Leu Ile Tyr Glu Glu Val Ala Arg
        355                 360                 365
Met Pro Pro Phe Arg Arg Lys Thr Leu Val Leu Ile Gly Ala Gln Gly
    370                 375                 380
Val Gly Arg Arg Ser Leu Lys Asn Lys Leu Ile Met Trp Asp Pro Asp
385                 390                 395                 400
Arg Tyr Gly Thr Thr Val Pro Tyr Thr Ser Arg Arg Pro Lys Asp Ser
                405                 410                 415
Glu Arg Glu Gly Gln Gly Tyr Ser Phe Val Ser Arg Gly Glu Met Glu
            420                 425                 430
Ala Asp Val Arg Ala Gly Arg Tyr Leu Glu His Gly Glu Tyr Glu Gly
        435                 440                 445
Asn Leu Tyr Gly Thr Arg Ile Asp Ser Ile Arg Gly Val Val Ala Ala
    450                 455                 460
Gly Lys Val Cys Val Leu Asp Val Asn Pro Gln Ala Val Lys Val Leu
465                 470                 475                 480
Arg Thr Ala Glu Phe Val Pro Tyr Val Val Phe Ile Glu Ala Pro Asp
                485                 490                 495
Phe Glu Thr Leu Arg Ala Met Asn Arg Ala Ala Leu Glu Ser Gly Ile
            500                 505                 510
Ser Thr Lys Gln Leu Thr Glu Ala Asp Leu Arg Arg Thr Val Glu Glu
        515                 520                 525
```

-continued

```
Ser Ser Arg Ile Gln Arg Gly Tyr Gly His Tyr Phe Asp Leu Cys Leu
    530                 535                 540

Val Asn Ser Asn Leu Glu Arg Thr Phe Arg Glu Leu Gln Thr Ala Met
545                 550                 555                 560

Glu Lys Leu Arg Thr Glu Pro Gln Trp Val Pro Val Ser Trp Val Tyr
                565                 570                 575
```

<210> SEQ ID NO 6
<211> LENGTH: 552
<212> TYPE: PRT
<213> ORGANISM: Mus Musculus

<400> SEQUENCE: 6

```
Met Pro Val Ala Ala Thr Asn Ser Glu Ser Ala Met Gln Gln Val Leu
  1               5                  10                  15

Asp Asn Leu Gly Ser Leu Pro Asn Ala Thr Gly Ala Ala Glu Leu Asp
                 20                  25                  30

Leu Ile Phe Leu Arg Gly Ile Met Glu Ser Pro Ile Val Arg Ser Leu
             35                  40                  45

Ala Lys Ala His Glu Arg Leu Glu Glu Thr Lys Leu Glu Ala Val Arg
 50                  55                  60

Asp Asn Asn Leu Glu Leu Val Gln Glu Ile Leu Arg Asp Leu Ala Glu
 65                  70                  75                  80

Leu Ala Glu Gln Ser Ser Thr Ala Ala Glu Leu Ala Arg Ile Leu Gln
                 85                  90                  95

Glu Pro His Phe Gln Ser Leu Leu Glu Thr His Asp Ser Val Ala Ser
            100                 105                 110

Lys Thr Tyr Glu Thr Pro Pro Ser Pro Gly Leu Asp Pro Thr Phe
            115                 120                 125

Ser Asn Gln Pro Val Pro Pro Asp Ala Val Arg Met Val Gly Ile Arg
130                 135                 140

Lys Thr Ala Gly Glu His Leu Gly Val Thr Phe Arg Val Glu Gly Gly
145                 150                 155                 160

Glu Leu Val Ile Ala Arg Ile Leu His Gly Gly Met Val Ala Gln Gln
                165                 170                 175

Gly Leu Leu His Val Gly Asp Ile Ile Lys Glu Val Asn Gly Gln Pro
            180                 185                 190

Val Gly Ser Asp Pro Arg Ala Leu Gln Glu Leu Leu Arg Ser Ala Ser
            195                 200                 205

Gly Ser Val Ile Leu Lys Ile Leu Pro Ser Tyr Gln Glu Pro His Leu
    210                 215                 220

Pro Arg Gln Val Phe Val Lys Cys His Phe Asp Tyr Asp Pro Ala Arg
225                 230                 235                 240

Asp Ser Leu Ser Pro Cys Lys Glu Ala Gly Leu Arg Phe Asn Ala Gly
                245                 250                 255

Asp Leu Leu Gln Ile Val Asn Gln Asp Asp Ala Asn Trp Trp Gln Ala
            260                 265                 270

Cys His Val Glu Gly Gly Ser Ala Gly Leu Ile Pro Ser Gln Leu Leu
            275                 280                 285

Glu Glu Lys Arg Lys Ala Phe Val Lys Arg Asp Leu Glu Leu Thr Pro
        290                 295                 300

Thr Ser Gly Thr Leu Cys Gly Ser Leu Ser Gly Lys Lys Lys Lys Arg
305                 310                 315                 320

Met Met Tyr Leu Thr Thr Lys Asn Ala Glu Phe Asp Arg His Glu Leu
```

```
                    325                 330                 335
Leu Ile Tyr Glu Val Ala Arg Met Pro Phe Arg Arg Lys Thr
                340                 345                 350
Leu Val Leu Ile Gly Ala Gln Gly Val Gly Arg Arg Ser Leu Lys Asn
            355                 360                 365
Lys Leu Ile Leu Trp Asp Pro Asp Arg Tyr Gly Thr Thr Val Pro Tyr
        370                 375                 380
Thr Ser Arg Arg Pro Lys Asp Ser Glu Arg Glu Gly Gln Gly Tyr Ser
385                 390                 395                 400
Phe Val Ser Arg Gly Glu Met Glu Ala Asp Ile Arg Ala Gly Arg Tyr
                405                 410                 415
Leu Glu His Gly Glu Tyr Glu Gly Asn Leu Tyr Gly Thr Arg Ile Asp
                420                 425                 430
Ser Ile Arg Gly Val Val Ala Ser Gly Lys Val Cys Val Leu Asp Val
            435                 440                 445
Asn Pro Gln Ala Val Lys Val Leu Arg Thr Ala Glu Phe Val Pro Tyr
        450                 455                 460
Val Val Phe Ile Glu Ala Pro Asp Tyr Glu Thr Leu Arg Ala Met Asn
465                 470                 475                 480
Arg Ala Ala Leu Glu Ser Gly Val Ser Thr Lys Gln Leu Thr Glu Ala
                485                 490                 495
Asp Leu Arg Arg Thr Val Glu Glu Ser Ser Arg Ile Gln Arg Gly Tyr
                500                 505                 510
Gly His Tyr Phe Asp Leu Ser Leu Val Asn Ser Asn Leu Glu Arg Thr
            515                 520                 525
Phe Arg Glu Leu Gln Thr Ala Met Glu Lys Leu Arg Thr Glu Pro Gln
        530                 535                 540
Trp Val Pro Val Ser Trp Val Tyr
545                 550

<210> SEQ ID NO 7
<211> LENGTH: 574
<212> TYPE: PRT
<213> ORGANISM: Homo sapiens

<400> SEQUENCE: 7

Gly Cys Ser Ala Ala Pro Val Ala Glu Gly Glu Gln Arg Arg Arg Gly
  1               5                  10                  15
Ala Thr Gly Ser Gly Gly Ser Gly Gly Ala Glu Ala Ala Glu Val Arg
                 20                  25                  30
Ala Ala Met Gln Gln Val Leu Glu Asn Leu Thr Glu Leu Pro Ser Ser
             35                  40                  45
Thr Gly Ala Glu Glu Ile Asp Leu Ile Phe Leu Lys Gly Ile Met Glu
         50                  55                  60
Asn Pro Ile Val Lys Ser Leu Ala Lys Ala His Glu Arg Leu Glu Asp
 65                  70                  75                  80
Ser Lys Leu Glu Ala Val Ser Asp Asn Leu Glu Leu Val Asn Glu
                 85                  90                  95
Ile Leu Glu Asp Ile Thr Pro Leu Ile Asn Val Asp Glu Asn Val Ala
                100                 105                 110
Glu Leu Val Gly Ile Leu Lys Glu Pro His Phe Gln Ser Leu Leu Glu
            115                 120                 125
Ala His Asp Ile Val Ala Ser Lys Cys Tyr Asp Ser Pro Pro Ser Ser
        130                 135                 140
```

-continued

```
Pro Glu Met Asn Asn Ser Ser Ile Asn Asn Gln Leu Leu Pro Val Asp
145                 150                 155                 160

Ala Ile Arg Ile Leu Gly Ile His Lys Arg Ala Gly Glu Pro Leu Gly
                165                 170                 175

Val Thr Phe Arg Val Glu Asn Asn Asp Leu Val Ile Ala Arg Ile Leu
            180                 185                 190

His Gly Gly Met Ile Asp Arg Gln Gly Leu Leu His Val Gly Asp Ile
        195                 200                 205

Ile Lys Glu Val Asn Gly His Glu Val Gly Asn Asn Pro Lys Glu Leu
    210                 215                 220

Gln Glu Leu Leu Lys Asn Ile Ser Gly Ser Val Thr Leu Lys Ile Leu
225                 230                 235                 240

Pro Ser Tyr Arg Asp Thr Ile Thr Pro Gln Gln Val Phe Val Lys Cys
                245                 250                 255

His Phe Asp Tyr Asn Pro Tyr Asn Asp Asn Leu Ile Pro Cys Lys Glu
            260                 265                 270

Ala Gly Leu Lys Phe Ser Lys Gly Glu Ile Leu Gln Ile Val Asn Arg
        275                 280                 285

Glu Asp Pro Asn Trp Trp Gln Ala Ser His Val Lys Glu Gly Gly Ser
    290                 295                 300

Ala Gly Leu Ile Pro Ser Gln Phe Leu Glu Glu Lys Arg Lys Ala Phe
305                 310                 315                 320

Val Arg Arg Asp Trp Asp Asn Ser Gly Pro Phe Cys Gly Thr Ile Ser
                325                 330                 335

Ser Lys Lys Lys Lys Met Met Tyr Leu Thr Thr Arg Asn Ala Glu
            340                 345                 350

Phe Asp Arg His Glu Ile Gln Ile Tyr Glu Glu Val Ala Lys Met Pro
        355                 360                 365

Pro Phe Gln Arg Lys Thr Leu Val Leu Ile Gly Ala Gln Gly Val Gly
    370                 375                 380

Arg Arg Ser Leu Lys Asn Arg Phe Ile Val Leu Asn Pro Thr Arg Phe
385                 390                 395                 400

Gly Thr Thr Val Pro Phe Thr Ser Arg Lys Pro Arg Glu Asp Glu Lys
                405                 410                 415

Asp Gly Gln Ala Tyr Lys Phe Val Ser Arg Ser Glu Met Glu Ala Asp
            420                 425                 430

Ile Lys Ala Gly Lys Tyr Leu Glu His Gly Glu Tyr Glu Gly Asn Leu
        435                 440                 445

Tyr Gly Thr Lys Ile Asp Ser Ile Leu Glu Val Val Gln Thr Gly Arg
    450                 455                 460

Thr Cys Ile Leu Asp Val Asn Pro Gln Ala Leu Lys Val Leu Arg Thr
465                 470                 475                 480

Ser Glu Phe Met Pro Tyr Val Val Phe Ile Ala Ala Pro Glu Leu Glu
                485                 490                 495

Thr Leu Arg Ala Met His Lys Ala Val Val Asp Ala Gly Ile Thr Thr
            500                 505                 510

Lys Leu Leu Thr Asp Ser Asp Leu Lys Lys Thr Val Asp Glu Ser Ala
        515                 520                 525

Arg Ile Gln Arg Ala Tyr Asn His Tyr Phe Asp Leu Ile Ile Ile Asn
    530                 535                 540

Asp Asn Leu Asp Lys Ala Phe Glu Lys Leu Gln Thr Ala Ile Glu Lys
545                 550                 555                 560

Leu Arg Met Glu Pro Gln Trp Val Pro Ile Ser Trp Val Tyr
```

-continued

<210> SEQ ID NO 8
<211> LENGTH: 539
<212> TYPE: PRT
<213> ORGANISM: Mus Musculus

<400> SEQUENCE: 8

Met Gln Gln Val Leu Glu Asn Leu Thr Glu Leu Pro Ser Ser Thr Gly
 1               5                  10                  15

Ala Glu Glu Ile Asp Leu Ile Phe Leu Lys Gly Ile Met Glu Asn Pro
            20                  25                  30

Ile Val Lys Ser Leu Ala Lys Ala His Glu Arg Leu Glu Asp Ser Lys
        35                  40                  45

Leu Glu Ala Val Ser Asp Asn Asn Leu Glu Leu Val Asn Glu Ile Leu
    50                  55                  60

Glu Asp Ile Thr Pro Leu Ile Ser Val Asp Glu Asn Val Ala Glu Leu
65                  70                  75                  80

Val Gly Ile Leu Lys Glu Pro His Phe Gln Ser Leu Leu Glu Ala His
                85                  90                  95

Asp Ile Val Ala Ser Lys Cys Tyr Asp Ser Pro Ser Ser Pro Glu
            100                 105                 110

Met Asn Ile Pro Ser Leu Asn Asn Gln Leu Pro Val Asp Ala Ile Arg
        115                 120                 125

Ile Leu Gly Ile His Lys Lys Ala Gly Glu Pro Leu Gly Val Thr Phe
    130                 135                 140

Arg Val Glu Asn Asn Asp Leu Val Ile Ala Arg Ile Leu His Gly Gly
145                 150                 155                 160

Met Ile Asp Arg Gln Gly Leu Leu His Val Gly Asp Ile Ile Lys Glu
                165                 170                 175

Val Asn Gly His Glu Val Gly Asn Asn Pro Lys Glu Leu Gln Glu Leu
            180                 185                 190

Leu Lys Asn Ile Ser Gly Ser Val Thr Leu Lys Ile Leu Pro Ser Tyr
        195                 200                 205

Arg Asp Thr Ile Thr Pro Gln Gln Val Phe Val Lys Cys His Phe Asp
    210                 215                 220

Tyr Asn Pro Phe Asn Asp Asn Leu Ile Pro Cys Lys Glu Ala Gly Leu
225                 230                 235                 240

Lys Phe Ser Lys Gly Glu Ile Leu Gln Ile Val Asn Arg Glu Asp Pro
                245                 250                 255

Asn Trp Trp Gln Ala Ser His Val Lys Glu Gly Gly Ser Ala Gly Leu
            260                 265                 270

Ile Pro Ser Gln Phe Leu Glu Glu Lys Arg Lys Ala Phe Val Arg Arg
        275                 280                 285

Asp Trp Asp Asn Ser Gly Pro Phe Cys Gly Thr Ile Ser Asn Lys Lys
    290                 295                 300

Lys Lys Lys Met Met Tyr Leu Thr Thr Arg Asn Ala Glu Phe Asp Arg
305                 310                 315                 320

His Glu Ile Gln Ile Tyr Glu Glu Val Ala Lys Met Pro Pro Phe Gln
                325                 330                 335

Arg Lys Thr Leu Val Leu Ile Gly Ala Gln Gly Val Gly Arg Arg Ser
            340                 345                 350

Leu Lys Asn Arg Phe Ile Val Leu Asn Pro Ala Arg Phe Gly Thr Thr
        355                 360                 365

-continued

```
Val Pro Phe Thr Ser Arg Lys Pro Arg Glu Asp Glu Lys Asp Gly Gln
    370                 375                 380

Ala Tyr Lys Phe Val Ser Arg Ser Glu Met Glu Ala Asp Ile Lys Ala
385                 390                 395                 400

Gly Lys Tyr Leu Glu His Gly Glu Tyr Glu Gly Asn Leu Tyr Gly Thr
                405                 410                 415

Lys Ile Asp Ser Ile Leu Glu Val Val Gln Thr Gly Arg Thr Cys Ile
            420                 425                 430

Leu Asp Val Asn Pro Gln Ala Leu Lys Val Leu Arg Thr Ser Glu Phe
        435                 440                 445

Met Pro Tyr Val Val Phe Ile Ala Ala Pro Glu Leu Glu Thr Leu Arg
    450                 455                 460

Ala Met His Lys Ala Val Val Asp Ala Gly Ile Thr Thr Lys Leu Leu
465                 470                 475                 480

Thr Asp Ser Asp Leu Lys Lys Thr Val Asp Glu Ser Ala Arg Ile Gln
            485                 490                 495

Arg Ala Tyr Asn His Tyr Phe Asp Leu Ile Ile Val Asn Asp Asn Leu
                500                 505                 510

Asp Lys Ala Phe Glu Lys Leu Gln Thr Ala Ile Glu Lys Leu Arg Met
            515                 520                 525

Glu Pro Gln Trp Val Pro Ile Ser Trp Val Tyr
    530                 535
```

ISOLATED HUMAN KINASE PROTEINS, NUCLEIC ACID MOLECULES ENCODING HUMAN KINASE PROTEINS, AND USES THEREOF

This application is a division of Ser. No. 09/801,191 filed Mar. 8, 2001 now U.S. Pat. No. 6,537,788.

FIELD OF THE INVENTION

The present invention is in the field of kinase proteins that are related to the membrane-associated guanylate kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books,* Vol 1:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine,* McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) Nature 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) J. Biol. Chem. 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) Annu. Rev. Cell. Biol. 8:463–93). Regulation of PTK activity may therefore be an important strategy in controlling some types of cancer.

Membrane-associated guanylate kinase (MAGUK) proteins participate in the assembly of multiprotein complexes on the inner surface of the plasma membrane at regions of cell-cell contact. MAGUK proteins share a common modular structure that consists of 1 or 3 PDZ domains, a SRC homology 3 (SH3) domain, and a C-terminal guanylate kinase (GuK) domain. Using the yeast 2-hybrid system to identify proteins that interact with the C terminus of KRasB, Dobrosotskaya et al. (1997) cloned mouse cDNAs encoding a protein which they called Magi1 for membrane-associated guanylate kinase with an inverted arrangement of protein-protein interaction domains. The predicted 1,171-amino acid protein has an N-terminal GuK domain, followed by 2 WW domains and 5 PDZ domains. Alternative splicing generates at least 3 transcripts that encode isoforms with unique C termini. Northern blot analysis revealed multiple Magi1 transcripts in many tissues. By using cell fractionation and Western blot analyses, a 148-kD isoform was discovered. The protein, containing nuclear localization signals in its C terminus, is located predominantly in the nucleus and a 137-kD isoform was found primarily in membrane and cytoplasmic fractions. Dobrosotskaya et al. (1997) stated that the amino acid sequence of mouse Magi1 is 93% identical to that of the partial human WWP3 identified by Pirozzi et al. (1997).

MAGUK involves in cell junction organization, tumor suppression, and signalling. Their structure includes one or three copies of a DHR or PDZ domain (discs-large homologous region or PSD-95/SAP90, discs-large ZO-1 homologous domain), an SH3 domain, and a guanylate kinase domain. MAGUKs were classified into two subfamilies: Dlg-like with three DHR/PDZ domains and p55-like with a single DHR/PDZ domain. There is now a new subfamily whose members have a novel domain structure: a calcium/calmodulin-dependent protein kinase domain in the N-terminus as well as the DHR/PDZ, SH3 and GUK domains in the C-terminus. These new MAGUKs may regulate transmembrane molecules that bind calcium, calmodulin, or nucleotides, camguk (cmg) is a Drosophila member of this novel MAGUK subfamily.

By screening a human brain cDNA library for WW domain-containing proteins, Pirozzi et al. (1997) identified a partial WWP3 cDNA. A longer BAIAPI cDNA with CAG trinucleotide repeats was isolated from a human brain cDNA library by Margolis et al. (1997). For a review of membrane-associated guanylate-kinase, see Dobrosotskaya et al., J. Biol. Chem. 272: 31589–31597, 1997, Margolis et al., Hum. Genet. 100: 114–122, 1997, Pirozzi et al., J. Biol. Chem. 272: 14611–14616, 1997 and Dimitratos et al., Mech Dev. 63(1):127–30, 1997.

Kinase proteins, particularly members of the membrane-associated guanylate kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the membrane-associated guanylate kinase subfamily.

SUMMARY OF THE INVENTION

The present invention is based in part on the identification of amino acid sequences of human kinase peptides and proteins that are related to the membrane-associated guanylate kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in the placenta, thyroid gland, muscle rhabdomyosarcoma, adrenal gland, infant brain, breast, brain glioblastoma, brain glioblastoma, retina and human hippocampus.

DESCRIPTION OF THE FIGURE SHEETS

FIG. 1 provides the nucleotide sequence of a cDNA molecule or transcript sequence that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the placenta, thyroid gland, muscle rhabdomyosarcoma, adrenal gland, infant brain, breast, brain glioblastoma, brain glioblastoma, retina and human hippocampus.

FIG. 2 provides the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. FIG. 3 provides information on SNPs that have been found in the gene encoding the kinase protein of the present invention. SNPs were identified at 65 different nucleotide positions in introns and regions 5' and 3' of the ORF. Such SNPs in introns and outside the ORF may affect control/regulatory elements.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the membrane-associated guanylate kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the membrane-associated guanylate kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the membrane-associated guanylate kinase subfamily and the expression pattern observed. Experimental data as provided in FIG. 1 indicates expression in the placenta, thyroid gland, muscle rhabdomyosarcoma, adrenal gland, infant brain, breast, brain glioblastoma, brain glioblastoma, retina and human hippocampus. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known membrane-associated guanylate kinase family or subfamily of kinase proteins.

Specific Embodiments

Peptide Molecules

The present invention provides nucleic acid sequences that encode protein molecules that have been identified as being members of the kinase family of proteins and are related to the membrane-associated guanylate kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in the placenta, thyroid gland, muscle rhabdomyosarcoma, adrenal gland, infant brain, breast, brain glioblastoma, brain glioblastoma, retina and human hippocampus. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWS-gapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. As indicated by the data presented in FIG. 3, the map position was determined to be on chromosome 17 by ePCR.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. As indicated by the data presented in FIG. 3, the map position was determined to be on chromosome 17 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been identified in a gene encoding the kinase protein of the present invention. 65 SNP variants were found, including 2 indels (indicated by a "–") and 4 SNPs in exons, of which 3 of these cause changes in the amino acid sequence (i.e., nonsynonymous SNPs). The changes in the amino acid sequence that these SNPs cause is indicated in FIG. 3 and can readily be determined using the universal genetic code and the protein sequence provided in FIG. 2 as a reference.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., Science 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., J. Mol. Biol. 224:899–904 (1992); de Vos et al. Science 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties, 2nd Ed., T. E. Creighton, W.H. Freeman and Company, New York (1993). Many detailed reviews are available on this subject, such as by Wold, F., Posttranslational Covalent Modification of Proteins, B. C. Johnson, Ed., Academic Press, New York 1–12 (1983); Seifter et al. (Meth. Enzymol. 182: 626–646 (1990)) and Rattan et al. (Ann. N.Y. Acad. Sci. 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in the placenta, thyroid gland, muscle rhabdomyosarcoma, adrenal gland, infant brain, breast, brain glioblastoma, brain glioblastoma, retina by virtual northern blot. In addition, PCR-based tissue screening panel indicates expression in human hippocampus. A large percentage of pharmaceutical agents are being developed that modulate the activity of kinase proteins, particularly members of the membrane-associated guanylate kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the placenta, thyroid gland, muscle rhabdomyosarcoma, adrenal gland, infant brain, breast, brain glioblastoma, brain glioblastoma, retina and human hippocampus. Such uses can readily be determined using the information provided herein, that which is known in the art, and routine experimentation.

The proteins of the present invention (including variants and fragments that may have been disclosed prior to the present invention) are useful for biological assays related to kinases that are related to members of the membrane-associated guanylate kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in the placenta, thyroid gland, muscle rhabdomyosarcoma, adrenal gland, infant brain, breast, brain glioblastoma, brain glioblastoma, retina by virtual northern blot. In addition, PCR-based tissue screening panel indicates expression in human hippocampus.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in the placenta, thyroid gland, muscle rhabdomyosarcoma, adrenal gland, infant brain, breast, brain glioblastoma, brain glioblastoma, retina and human hippocampus. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in the placenta, thyroid gland, muscle rhabdomyosarcoma, adrenal gland, infant brain, breast, brain glioblastoma, brain glioblastoma, retina by virtual northern blot. In addition, PCR-based tissue screening panel indicates expression in human hippocampus.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in the placenta, thyroid gland, muscle rhabdomyosarcoma, adrenal gland, infant brain, breast, brain glioblastoma, brain glioblastoma, retina and human hippocampus. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the placenta, thyroid gland, muscle rhabdomyosarcoma, adrenal gland, infant brain, breast, brain glioblastoma, brain glioblastoma, retina and human hippocampus. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the placenta, thyroid gland, muscle rhabdomyosarcoma, adrenal gland, infant brain, breast, brain glioblastoma, brain glioblastoma, retina and human hippocampus. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in the placenta, thyroid gland, muscle rhabdomyosarcoma, adrenal gland, infant brain, breast, brain glioblastoma, brain glioblastoma, retina by virtual northern blot. In addition, PCR-based tissue screening panel indicates expression in human hippocampus. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the placenta, thyroid gland, muscle rhabdomyosarcoma, adrenal gland, infant brain, breast, brain glioblastoma, brain glioblastoma, retina and human hippocampus. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the placenta, thyroid gland, muscle rhabdomyosarcoma, adrenal gland, infant brain, breast, brain glioblastoma, brain glioblastoma, retina and human hippocampus. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the placenta, thyroid gland, muscle rhabdomyosarcoma, adrenal gland, infant brain, breast, brain glioblastoma, brain glioblastoma, retina and human hippocampus. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 17 by ePCR.

FIG. 3 provides information on SNPs that have been identified in a gene encoding the kinase protein of the present invention. 65 SNP variants were found, including 2 indels (indicated by a "–") and 4 SNPs in exons, of which 3 of these cause changes in the amino acid sequence (i.e., nonsynonymous SNPs). The changes in the amino acid sequence that these SNPs cause is indicated in FIG. 3 and can readily be determined using the universal genetic code and the protein sequence provided in FIG. 2 as a reference.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6×sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. FIG. 3 provides information on SNPs that have been found in the gene encoding the kinase protein of the present invention. SNPs were identified at 65 different nucleotide positions in introns and regions 5' and 3' of the ORF. Such SNPs in introns and outside the ORF may affect control/regulatory elements.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 17 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in the placenta, thyroid gland, muscle rhabdomyosarcoma, adrenal gland, infant brain, breast, brain glioblastoma, brain glioblastoma, retina by virtual northern blot. In addition, PCR-based tissue screening panel indicates expression in human hippocampus. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in the placenta, thyroid gland, muscle rhabdomyosarcoma, adrenal gland, infant brain, breast, brain glioblastoma, brain glioblastoma, retina by virtual northern blot. In addition, PCR-based tissue screening panel indicates expression in human hippocampus.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in the placenta, thyroid gland, muscle rhabdomyosarcoma, adrenal gland, infant brain, breast, brain glioblastoma, brain glioblastoma, retina and human hippocampus. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in the placenta, thyroid gland, muscle rhabdomyosarcoma, adrenal gland, infant brain, breast, brain glioblastoma, brain glioblastoma, retina by virtual northern blot. In addition, PCR-based tissue screening panel indicates expression in human hippocampus. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in the placenta, thyroid gland, muscle rhabdomyosarcoma, adrenal gland, infant brain, breast, brain glioblastoma, brain glioblastoma, retina and human hippocampus.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been identified in a gene encoding the kinase protein of the present invention. 65 SNP variants were found, including 2 indels (indicated by a "−") and 4 SNPs in exons, of which 3 of these cause changes in the amino acid sequence (i.e., nonsynonymous SNPs). The changes in the amino acid sequence that these SNPs cause is indicated in FIG. 3 and can readily be determined using the universal genetic code and the protein sequence provided in FIG. 2 as a reference. As indicated by the data presented in FIG. 3, the map position was determined to be on chromosome 17 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., Science 241:1077–1080 (1988); and Nakazawa et al., PNAS 91:360–364 (1994)), the latter of which can be particularly useful for detecting point mutations in the gene (see Abravaya et al., Nucleic Acids Res. 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) Biotechniques 19:448), including sequencing by mass spectrometry (see, e.g., PCT International Publication No. WO 94/16101; Cohen et al., Adv. Chromatogr. 36:127–162 (1996); and Griffin et al., Appl. Biochem. Biotechnol. 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286–295 (1992)), electrophoretic mobility of mutant and wild type nucleic acid is compared (Orita et al., PNAS 86:2766 (1989); Cotton et al., Mutat. Res. 285:125–144 (1993); and Hayashi et al., Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been identified in a gene encoding the kinase protein of the present invention. 65 SNP variants were found, including 2 indels (indicated by a "−") and 4 SNPs in exons, of which 3 of these cause changes in the amino acid sequence (i.e., nonsynonymous SNPs). The changes in the amino acid sequence that these SNPs cause is indicated in FIG. 3 and can readily be determined using the universal genetic code and the protein sequence provided in FIG. 2 as a reference.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in the placenta, thyroid gland, muscle rhabdomyosarcoma, adrenal gland, infant brain, breast, brain glioblastoma, brain glioblastoma, retina by virtual northern blot. In addition, PCR-based tissue screening panel indicates expression in human hippocampus. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been identified in a gene encoding the kinase protein of the present invention. 65 SNP variants were found, including 2 indels (indicated by a "–") and 4 SNPs in exons, of which 3 of these cause changes in the amino acid sequence (i.e., nonsynonymous SNPs). The changes in the amino acid sequence that these SNPs cause is indicated in FIG. 3 and can readily be determined using the universal genetic code and the protein sequence provided in FIG. 2 as a reference.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and*

*Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli,* the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.,* Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide, wherein the amino acid sequence of said polypeptide consists of SEQ ID NO:2.
2. An isolated polypeptide, wherein the amino acid sequence of said polypeptide comprises SEQ ID NO:2.
3. An isolated polypeptide, wherein the amino acid sequence of said polypeptide consists of SEQ ID NO:2, except that residue 80 of SEQ ID NO:2 is histidine.
4. An isolated polypeptide, wherein the amino acid sequence of said polypeptide comprises SEQ ID NO:2, except that residue 80 of SEQ ID NO:2 is histidine.
5. An isolated polypeptide, wherein the amino acid sequence of said polypeptide consists of SEQ ID NO:2, except that residue 81 of SEQ ID NO:2 is valine.
6. An isolated polypeptide, wherein the amino acid sequence of said polypeptide comprises SEQ ID NO:2, except that residue 81 of SEQ ID NO:2 is valine.
7. The polypeptide of claim 1, further comprising a heterologous amino acid sequence.
8. The polypeptide of claim 2, further comprising a heterologous amino acid sequence.
9. The polypeptide of claim 3, further comprising a heterologous amino acid sequence.
10. The polypeptide of claim 4, further comprising a heterologous amino acid sequence.
11. The polypeptide of claim 5, further comprising a heterologous amino acid sequence.
12. The polypeptide of claim 6, further comprising a heterologous amino acid sequence.
13. A composition comprising the polypeptide of claim 1 and a carrier.
14. A composition comprising the polypeptide of claim 2 and a carrier.
15. A composition comprising the polypeptide of claim 3 and a carrier.
16. A composition comprising the polypeptide of claim 4 and a carrier.
17. A composition comprising the polypeptide of claim 5 and a carrier.
18. A composition comprising the polypeptide of claim 6 and a carrier.
19. A composition comprising the polypeptide of claim 7 and a carrier.
20. A composition comprising the polypeptide of claim 8 and a carrier.
21. A composition comprising the polypeptide of claim 9 and a carrier.
22. A composition comprising the polypeptide of claim 10 and a carrier.
23. A composition comprising the polypeptide of claim 11 and a carrier.
24. A composition comprising the polypeptide of claim 12 and a carrier.

* * * * *